(12) United States Patent
Yamaguchi et al.

(10) Patent No.: US 8,148,044 B2
(45) Date of Patent: Apr. 3, 2012

(54) POSITIVE PHOTOSENSITIVE COMPOSITION

(75) Inventors: Shuhei Yamaguchi, Haibara-gun (JP); Tomotaka Tsuchimura, Haibara-gun (JP); Yuko Tada, Haibara-gun (JP)

(73) Assignee: Fujifilm Corporation, Tokyo (JP)

( * ) Notice: Subject to any disclaimer, the term of this patent is extended or adjusted under 35 U.S.C. 154(b) by 331 days.

(21) Appl. No.: 12/608,567

(22) Filed: Oct. 29, 2009

(65) Prior Publication Data

US 2010/0136479 A1 Jun. 3, 2010

(30) Foreign Application Priority Data

Oct. 31, 2008 (JP) ................................ 2008-282610
Nov. 26, 2008 (JP) ................................ 2008-301006

(51) Int. Cl.
*G03F 7/039* (2006.01)
*G03F 7/20* (2006.01)
*G03F 7/30* (2006.01)
*C07C 309/15* (2006.01)

(52) U.S. Cl. ..................... 430/270.1; 430/919; 430/920; 430/921; 430/923; 430/925; 430/905; 430/910; 430/326; 562/105; 562/100; 562/113; 562/115

(58) Field of Classification Search .................. None
See application file for complete search history.

(56) References Cited

U.S. PATENT DOCUMENTS

| | | |
|---|---|---|
| 2002/0102491 A1 | 8/2002 | Kodama et al. |
| 2005/0130060 A1 | 6/2005 | Kodama et al. |
| 2007/0003871 A1 | 1/2007 | Kodama et al. |
| 2008/0166660 A1 | 7/2008 | Takata et al. |
| 2009/0148791 A1 | 6/2009 | Kodama et al. |
| 2010/0304303 A1* | 12/2010 | Maeda et al. ............ 430/286.1 |

FOREIGN PATENT DOCUMENTS

| | | |
|---|---|---|
| JP | 2002-214774 A | 7/2002 |
| JP | 2008-170983 A | 7/2008 |

* cited by examiner

*Primary Examiner* — Sin J. Lee
(74) *Attorney, Agent, or Firm* — Sughrue Mion, PLLC

(57) ABSTRACT

A positive photosensitive composition includes at least one compound that when exposed to actinic rays or radiation, generates any of the sulfonic acids of general formula (I) and a resin whose solubility in an alkali developer is increased by the action of an acid,

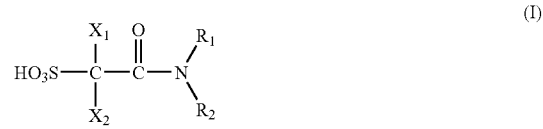

(I)

wherein each of $X_1$ and $X_2$ independently represents a fluorine atom or a fluoroalkyl group, $R_1$ represents a group with a polycyclic structure, provided that the polycyclic structure may have a substituent, and $R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent, and provided that $R_1$ and $R_2$ may be bonded to each other to thereby form a polycyclic structure.

17 Claims, 1 Drawing Sheet

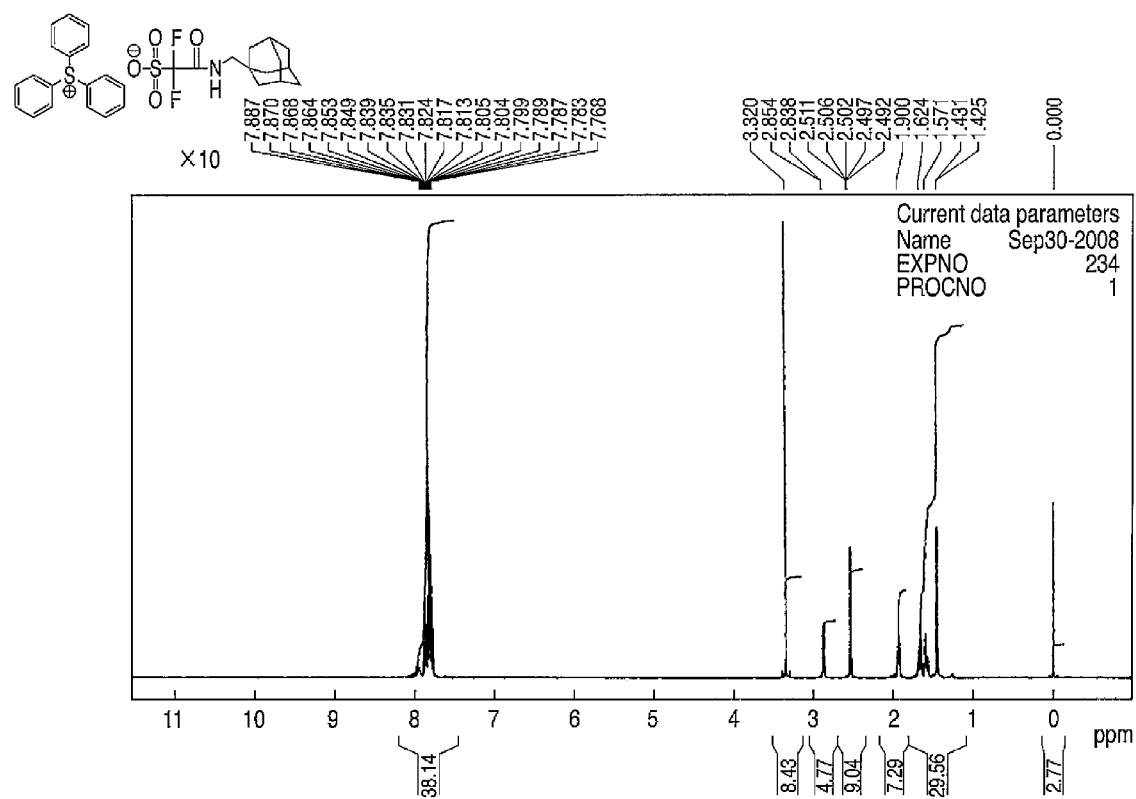

POSITIVE PHOTOSENSITIVE COMPOSITION

CROSS-REFERENCE TO RELATED APPLICATIONS

This application is based upon and claims the benefit of priority from prior Japanese Patent Applications No. 2008-282610, filed Oct. 31, 2008; and No. 2008-301006, filed Nov. 26, 2008, the entire contents of both of which are incorporated herein by reference.

BACKGROUND OF THE INVENTION

1. Field of the Invention

The present invention relates to a photoacid generator added to a positive photosensitive composition for use in a process for producing a semiconductor such as an IC, a process for producing a circuit board for e.g., a thermal head or a liquid crystal, and other photofabrication processes, and relates to a positive photosensitive composition containing the photoacid generator and a method of forming a pattern by use thereof. More particularly, the present invention relates to a photoacid generator that finds appropriate application when an exposure light source emits far ultraviolet, electron beams or the like of wavelength 250 nm or shorter, preferably 220 nm or shorter, and also relates to a positive photosensitive composition containing the photoacid generator and a method of forming a pattern by use thereof.

2. Description of the Related Art

When the conventional resist comprised of a novolak and a naphthoquinone diazide compound is used in the lithographic patternization employing far ultraviolet or excimer laser beams, the light transmission to the bottom portion of the resist is hampered by the high absorption in the far-ultraviolet region of the novolak and naphthoquinone diazide with the result that only a tapered pattern can be obtained with low sensitivity.

One of the means for solving this problem can be provided by a chemical-amplification resist composition. A chemical-amplification positive resist composition is a pattern forming material that is capable of, upon exposure to far ultraviolet or other radiation, generating an acid at the exposed area and, by a reaction catalyzed by the acid, changing the solubility in a developer between the area having been exposed to actinic radiation and the nonexposed area to thereby attain pattern formation on a substrate.

As examples of such resist compositions, there can be mentioned combinations of a compound capable of generating an acid by photodecomposition with any of an acetal or O,N-acetal compound, an orthoester or amide acetal compound, a polymer having an acetal or ketal group in its principal chain, an enol ether compound, an N-acyliminocarbonic acid compound, a polymer having an orthoester group in its principal chain, a tertiary alkyl ester compound, a silyl ester compound and a silyl ether compound. These exhibit a quantum yield of, in principle, over 1, thereby ensuring a high photosensitivity.

Further, as a system that is decomposed by heating in the presence of an acid to thereby become soluble in an alkali, there can be mentioned, for example, systems each consisting of a combination of a compound capable of generating an acid upon exposure to radiation with any of an ester of tertiary or secondary carbon (for example, t-butyl or 2-cyclohexenyl) or carbonic acid ester compound, an acetal compound and a t-butyl ether compound, as described in non-patent references 1 to 5.

In these systems, a resin whose fundamental skeleton consists of a poly(hydroxystyrene) exhibiting a low absorption mainly in the region of 248 nm is employed as a major component thereof. Accordingly, when a KrF excimer laser is used as a exposure light source, there can be attained a high sensitivity, high resolving power and favorable pattern formation. Thus, a system superior to the conventional naphthoquinone diazide/novolak resin system can be realized.

However, in using a light source of a further shorter wavelength, for example, an exposure light source of an ArF excimer laser (193 nm), as the compounds having aromatic groups inherently exhibit a sharp absorption in the region of 193 nm, the above-mentioned chemical amplification system has not been satisfactory. Moreover, the use of a poly(meth)acrylate as a polymer exhibiting a low absorption in the wavelength region of 193 nm is described in non-patent reference 6. However, there is the problem that this polymer is poor in the resistance to dry etching as generally carried out in semiconductor producing processes as compared with that of the conventional phenolic resin having an aromatic group.

In this connection, non-patent reference 7 reports that polymers having an alicyclic hydrocarbon group not only exhibit a resistance to dry etching comparable to that realized by an aromatic group but also have a low absorption in the region of 193 nm. Hence, in recent years, intensive studies have been conducted on the use of such polymers.

The photoacid generators that can be used along with the above-mentioned polymers include a compound capable of generating a trifluoromethanesulfonic acid, such as triphenylsulfonium trifluoromethanesulfonate, and a compound capable of generating a fluoroalkylsulfonic acid with a prolonged chain.

Further, the well-known acid generators include those capable of generating a perfluoroalkanesulfonic acid, such as triphenylsulfonium triflate or bis(t-butylphenyl)iodonium perfluorobutanesulfonate. Generally, perfluoroalkyl compounds have such a high hydrophobicity that appropriate use can be made in, for example, the water repellent finishing of clothes. Accordingly, the resists containing an acid generator that when exposed to actinic rays, generates a perfluoroalkylsulfonic acid exhibit poor affinity to aqueous developers, thereby causing the problem that a sensitivity decrease or occurrence of development residue (scum) would be invited by a deterioration of developability. As measures for coping with this problem, it has been reported to use a fluoroalkanesulfonic acid having an amido structure in its molecules (see, for example, patent reference 1) or a fluoroalkanesulfonic acid having an ester structure in its molecules (see, for example, patent reference 2).

Patent reference 1: Jpn. Pat. Appln. KOKAI Publication No. (hereinafter referred to as JP-A-) 2002-214774,
Patent reference 2: JP-A-2008-170983,
Non-patent reference 1: Polym. Eng. Sce., Vol. 23, page 1012 (1983),
Non-patent reference 2: ACS. Sym. Vol. 242, page 11 (1984),
Non-patent reference 3: Semiconductor World, 1987, November Issue, page 91,
Non-patent reference 4: Macromolecules, Vol. 21, page 1475 (1988),
Non-patent reference 5: SPIE, Vol. 920, page 42 (1988),
Non-patent reference 6: J. Vac. Sci. Technol., B9, 3357 (1991), and
Non-patent reference 7: Proc. of SPIE, 1672, 66 (1992).

BRIEF SUMMARY OF THE INVENTION

It is an object of the present invention to solve the problem of the technology of enhancing the performance inherent to microphotofabrication in which use is made of far ultraviolet, EUV, electron beams, etc., especially ArF excimer laser beams. It is a particular object of the present invention to provide a positive photosensitive composition excelling in sensitivity, resolving power and exposure margin.

The inventors have found that the above objects can be attained by using a compound capable of generating a sulfonic acid having a specified amido structure in its molecules as a photoacid generator in a positive photosensitive composition, thereby arriving at the completion of the present invention. It is presumed that the effect of the present invention, although not elucidated, is brought about by the enhancement of the affinity to developers of the sulfonic acid realized by the introduction of a specified amido structure in the molecules thereof.

(1) A positive photosensitive composition comprising at least one compound that when exposed to actinic rays or radiation, generates any of the sulfonic acids of general formula (I) and a resin whose solubility in an alkali developer is increased by the action of an acid,

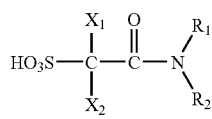
(I)

wherein each of $X_1$ and $X_2$ independently represents a fluorine atom or a fluoroalkyl group; $R_1$ represents a group with a polycyclic structure, provided that the polycyclic structure may have a substituent; and $R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent, and provided that $R_1$ and $R_2$ may be bonded to each other to thereby form a polycyclic structure.

(2) The positive photosensitive composition according to item (1), wherein the compound that when exposed to actinic rays or radiation, generates any of the sulfonic acids of general formula (I) is any of the compounds of general formula (II):

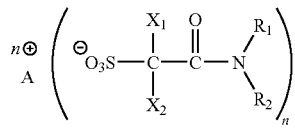
(II)

wherein $A^+$ represents an organic counter ion; n is 1 or 2; and $X_1$, $X_2$, $R_1$ and $R_2$ are as defined above with respect to general formula (I).

(3) The positive photosensitive composition according to item (1) or (2), wherein in general formula (I) or (II), both of $X_1$ and $X_2$ represent a fluorine atom.

(4) The positive photosensitive composition according to item (2) or (3), wherein in general formula (II), $A^+$ is any of the cations of any of formulae (IIIa), (IIIb), (IIIc) and (IIId):

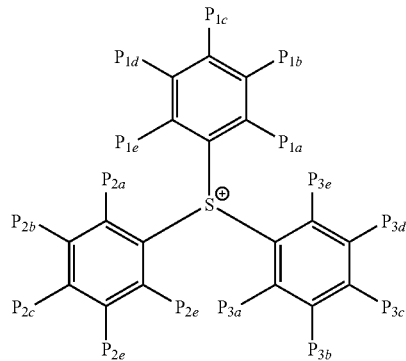
(IIIa)

wherein each of $P_{1a}$ to $P_{1e}$, each of $P_{2a}$ to $P_{2e}$, and each of $P_{3a}$ to $P_{3e}$ independently represents a hydrogen atom, a hydroxyl group, an alkyl group having 1 to 12 carbon atoms, a cycloalkyl group having 3 to 12 carbon atoms or a chain or alicyclic alkoxy group having 1 to 12 carbon atoms, provided that each of the alkyl group, cycloalkyl group and alkoxy group may have a substituent, and provided that $P_{1a}$ and $P_{3e}$, $P_{1e}$ and $P_{2a}$, and $P_{2e}$ and $P_{3a}$ may be bonded to each other through a single bond, methylene group, an ether bond or a sulfide bond,

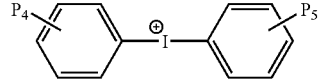
(IIIb)

wherein each of $P_4$ and $P_5$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent,

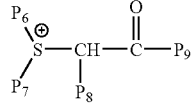
(IIIc)

wherein each of $P_6$ and $P_7$ independently represents an alkyl group having 1 to 12 carbon atoms or a cycloalkyl group having 3 to 12 carbon atoms, provided that each of the alkyl group and cycloalkyl group may have a substituent, and provided that $P_6$ and $P_7$ may be bonded to each other so as to represent a bivalent hydrocarbon group having 3 to 12 carbon atoms, and wherein $P_8$ represents a hydrogen atom, and $P_9$ represents an alkyl group having 1 to 12 carbon atoms, a cycloalkyl group having 3 to 12 carbon atoms or an aromatic ring group, provided that each of the alkyl group, cycloalkyl group and aromatic ring group may have a substituent, and provided that $P_8$ and $P_9$ may be bonded to each other so as to represent a bivalent hydrocarbon group having 3 to 12 carbon atoms, and wherein any of the carbon atoms contained in the bivalent hydrocarbon group may be substituted by a carbonyl group, an oxygen atom or a sulfur atom, and

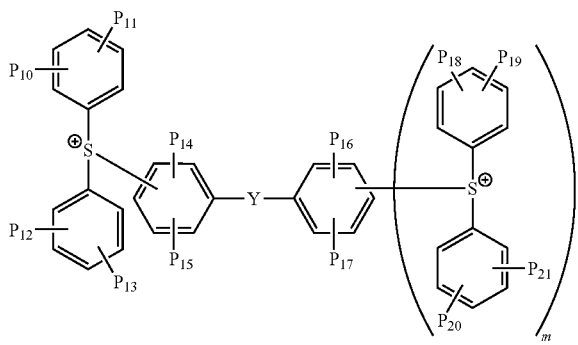

wherein each of $P_{10}$ to $P_{21}$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent, and wherein Y represents a sulfur atom or an oxygen atom, and m is 0 or 1.

(5) The positive photosensitive composition according to item (2) or (3), wherein in general formula (II), $A^+$ any of the cations of formula (IIIe):

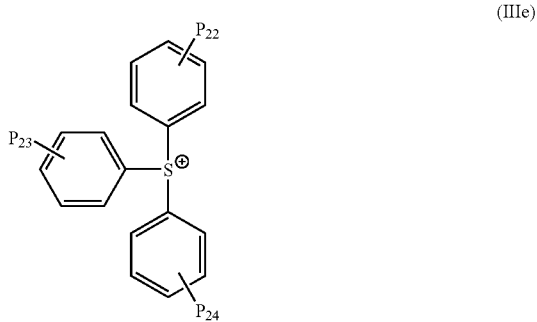

wherein each of $P_{22}$ to $P_{24}$ independently represents a hydrogen atom or an alkyl group having 1 to 4 carbon atoms, provided that the alkyl group may have a substituent.

(6) The positive photosensitive composition according to any of items (1) to (5), wherein the resin has a lactone structure.

(7) A method of forming a pattern, comprising forming the positive photosensitive composition according to any of items (1) to (6) into a coating film, exposing the coating film to actinic rays or radiation and developing the exposed coating film by use of an alkali developer.

(8) A compound capable of, when exposed to actinic rays or radiation, generating any of the sulfonic acids of general formula (I),

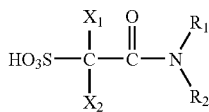

wherein each of $X_1$ and $X_2$ independently represents a fluorine atom or a fluoroalkyl group; $R_1$ represents a group with a polycyclic structure, provided that the polycyclic structure may have a substituent; and $R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent, and provided that $R_1$ and $R_2$ may be bonded to each other to thereby form a polycyclic structure.

(9) The compound capable of, when exposed to actinic rays or radiation, generating any of the sulfonic acids of general formula (I) according to item (8), which compound is any of the compounds of general formula (II):

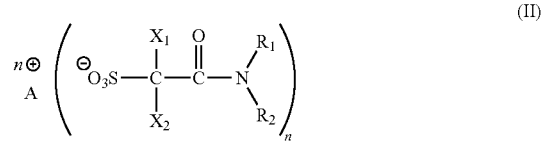

wherein $A^+$ represents an organic counter ion; n is 1 or 2; and $X_1$, $X_2$, $R_1$ and $R_2$ are as defined above with respect to general formula (I).

(10) The compound according to item (8) or (9), wherein in general formula (I) or (II), both of $X_1$ and $X_2$ represent a fluorine atom.

(11) The compound according to item (9) or (10), wherein in general formula (II), $A^+$ is any of the cations of any of formulae (IIIc), (IIIb), (IIIc) and (IIId):

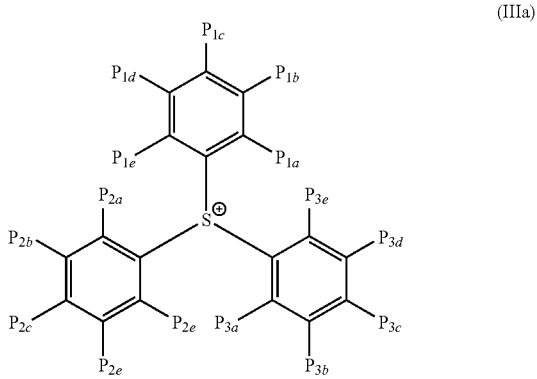

wherein each of $P_{1a}$ to $P_{1e}$, each of $P_{2a}$ to $P_{2e}$, and each of $P_{3a}$ to $P_{3e}$ independently represents a hydrogen atom, a hydroxyl group, an alkyl group having 1 to 12 carbon atoms, a cycloalkyl group having 3 to 12 carbon atoms or a chain or alicyclic alkoxy group having 1 to 12 carbon atoms, provided that each of the alkyl group, cycloalkyl group and alkoxy group may have a substituent, and provided that $P_{1a}$ and $P_{3e}$, $P_{1e}$ and $P_{2a}$, and $P_{2e}$ and $P_{3a}$ may be bonded to each other through a single bond, methylene, an ether bond or a sulfide bond,

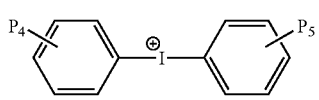
(IIIb)

wherein each of $P_4$ and $P_5$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent,

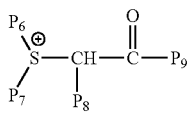
(IIIc)

wherein each of $P_6$ and $P_7$ independently represents an alkyl group having 1 to 12 carbon atoms or a cycloalkyl group having 3 to 12 carbon atoms, provided that each of the alkyl group and cycloalkyl group may have a substituent, and provided that $P_6$ and $P_7$ may be bonded to each other so as to represent a bivalent hydrocarbon group having 3 to 12 carbon atoms, and wherein $P_8$ represents a hydrogen atom, and $P_9$ represents an alkyl group having 1 to 12 carbon atoms, a cycloalkyl group having 3 to 12 carbon atoms or an aromatic ring group, provided that each of the alkyl group, cycloalkyl group and aromatic ring group may have a substituent, and provided that $P_8$ and $P_9$ may be bonded to each other so as to represent a bivalent hydrocarbon group having 3 to 12 carbon atoms, and wherein any of the carbon atoms contained in the bivalent hydrocarbon group may be substituted by a carbonyl group, an oxygen atom or a sulfur atom, and

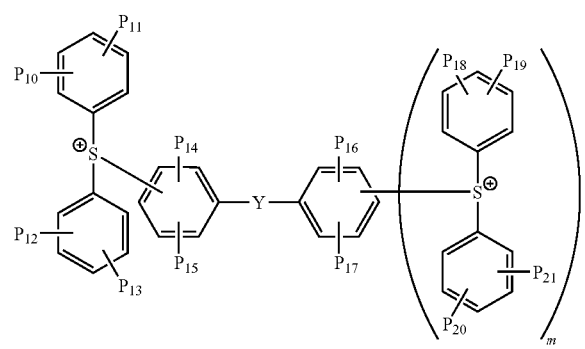
(IIId)

wherein each of $P_{10}$ to $P_{21}$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent, and wherein Y represents a sulfur atom or an oxygen atom, and m is 0 or 1.

(12) The compound according to item (9) or (10), wherein in general formula (II), $A^+$ is any of the cations of formula (IIIe):

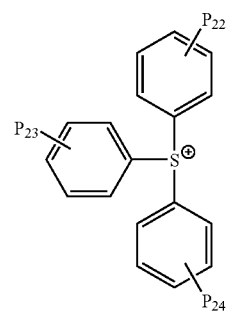
(IIIe)

wherein each of $P_{22}$ to $P_{24}$ independently represents a hydrogen atom or an alkyl group having 1 to 4 carbon atoms, provided that the alkyl group may have a substituent.

(13) A compound of general formula (IV),

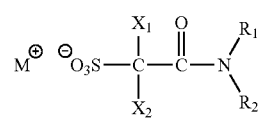
(IV)

wherein $M^+$ represents a metal ion; each of $X_1$ and $X_2$ independently represents a fluorine atom or a fluoroalkyl group; $R_1$ represents a group with a polycyclic structure; and $R_2$ represents a hydrogen atom, a chain alkyl group, a monocyclic alkyl group, a group with a polycyclic structure or a monocyclic aryl group, provided that each of the chain alkyl group, monocyclic alkyl group and monocyclic aryl group may have a substituent, and provided that $R_1$ and $R_2$ may be bonded to each other to thereby form a polycyclic structure.

(14) The compound according to item (13), wherein in general formula (IV), both of $X_1$ and $X_2$ represent a fluorine atom.

(15) A process for producing the compound of general formula (IV) according to item (13) or (14), comprising reacting any of the amines of general formula (V) with any of the ester compounds of general formula (VI),

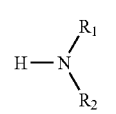
(V)

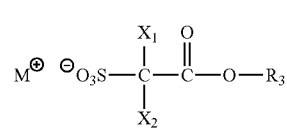
(VI)

wherein in general formula (V), $R_1$ and $R_2$ are as defined above with respect to general formula (IV), and wherein in general formula (VI), $M^+$, $X_1$ and $X_2$ are as defined above with respect to general formula (IV), and $R_3$ represents a chain alkyl group, a cycloalkyl group or a group with a polycyclic structure, provided that each of the chain alkyl group and cycloalkyl group may have a substituent.

(16) A process for producing the compound of general formula (II) according to any of items (9) to (12), comprising reacting any of the amines of general formula (V) with any of the ester compounds of general formula (VII),

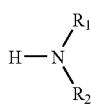

(V)

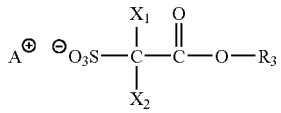

(VII)

wherein in general formula (V), $R_1$ and $R_2$ are as defined above with respect to general formula (II), and wherein in general formula (VII), $A^+$, $X_1$ and $X_2$ are as defined above with respect to general formula (II), and $R_3$ represents a chain alkyl group, a cycloalkyl group or a group with a polycyclic structure, provided that each of the chain alkyl group and cycloalkyl group may have a substituent.

(17) A photoacid generator comprised of any of the compounds of items (8) to (12).

The present invention has made it feasible to provide a positive photosensitive composition excelling in sensitivity, resolving power and exposure margin.

BRIEF DESCRIPTION OF THE SEVERAL VIEWS OF THE DRAWING

The single FIGURE shows the $^1$HNMR chart of compound X10 according to the present invention synthesized in an Example.

DETAILED DESCRIPTION OF THE INVENTION

The present invention will be described in detail below.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

[(A) Photoacid Generator]

The compounds provided by the present invention are those that when exposed to actinic rays or radiation, generate any of the sulfonic acids of general formula (I) (hereinafter also referred to as "compounds according to the present invention," "salts according to the present invention" or the like), and can be used as photoacid generators in positive photosensitive compositions.

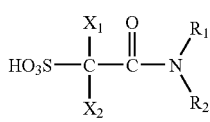

(I)

In general formula (I), each of $X_1$ and $X_2$ independently represents a fluorine atom or a fluoroalkyl group. Preferably, each of $X_1$ and $X_2$ is a fluorine atom or a fluoroalkyl group having 1 to 6 carbon atoms. A fluorine atom is especially preferred.

$R_1$ represents a group with a polycyclic structure. In the present invention, the group with a polycyclic structure refers to a polycyclic hydrocarbon group or an alkyl group containing two or more monocyclic hydrocarbon groups or one or more polycyclic hydrocarbon groups. The polycyclic hydrocarbon groups and monocyclic hydrocarbon groups may be aliphatic or aromatic. Alicyclic hydrocarbon groups are especially preferred.

As the polycyclic hydrocarbon groups, there can be mentioned, for example, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicycl[4.1.0]heptanyl and the like. Norbornyl, adamantyl and noradamantyl are especially preferred.

As the monocyclic hydrocarbon groups, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl and the like. Cyclopropyl, cyclopentyl, cyclohexyl and cyclooctyl are especially preferred.

The above polycyclic structure may have a substituent. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group or the like.

$R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent.

The chain alkyl group may consist of a linear or branched chain. As the chain alkyl group, there can be mentioned methyl, ethyl, propyl, butyl, pentyl, hexyl, heptyl, octyl, dodecyl, 2-ethylhexyl, isopropyl, sec-butyl, t-butyl, isoamyl or the like.

The alkyl group may have a substituent. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group or the like.

As the monocyclic alkyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl or the like. Cyclopropyl, cyclopentyl, cyclohexyl and cyclooctyl are especially preferred.

The monocyclic alkyl group may have a substituent. As the substituent, there can be mentioned a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group or the like.

The group with a polycyclic structure has the same meaning as that represented by $R_1$. The particular examples and substituents thereof are also the same as mentioned above with respect to the group with a polycyclic structure represented by $R_1$.

The monocyclic aryl group refers to a substituted or unsubstituted phenyl group. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group or the like.

$R_1$ and $R_2$ may be bonded to each other to thereby form a polycyclic structure. A decahydroquinoline or decahydroisoquinoline skeleton or the like can be mentioned as the polycyclic structure formed by $R_1$ and $R_2$, which may have a substituent.

Specific examples of the sulfonic acids of general formula (I) according to the present invention will be shown below.

In the formulae, each of $X_1$ and $X_2$ independently represents a fluorine atom or a perfluoroalkyl group having 1 to 6 carbon atoms.

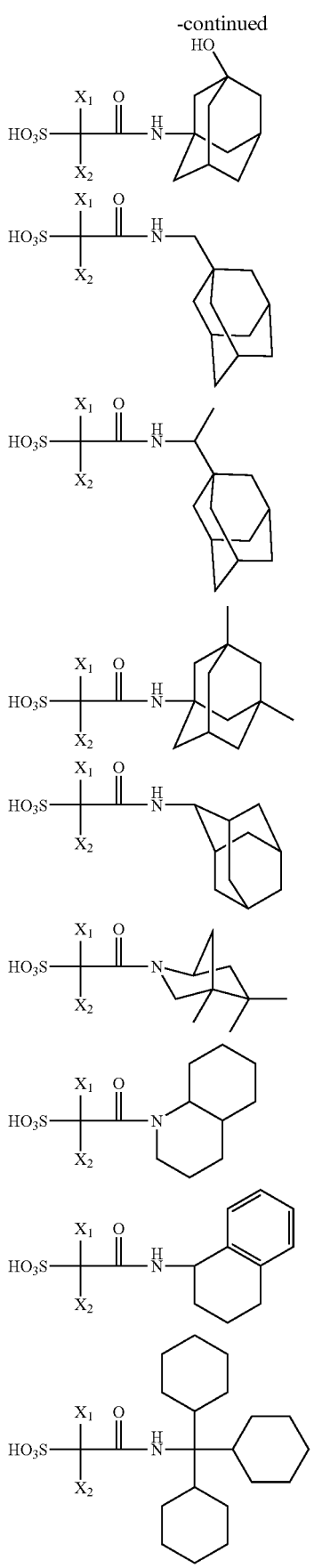

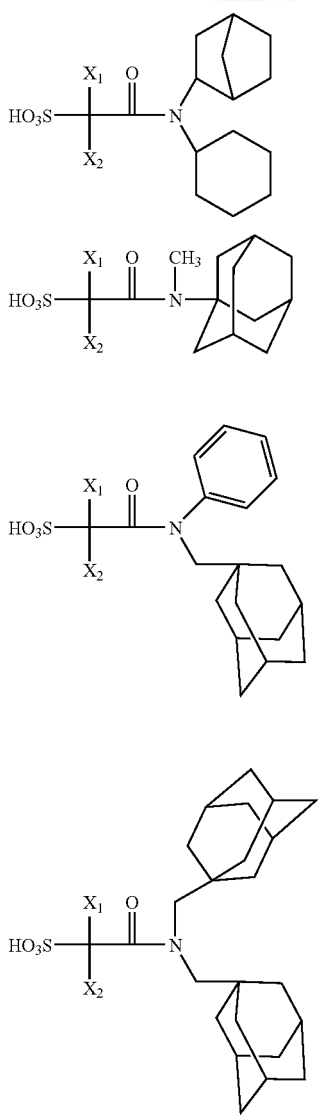

It is preferred for the compounds of the present invention capable of generating the sulfonic acids of general formula (I) to be the salts of general formula (II) shown below.

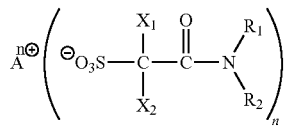

In formula (II), $A^+$ represents an organic counter ion and n is 1 or 2. $X_1$, $X_2$, $R_1$ and $R_2$ are as defined above with respect to general formula (I).

Preferably, the organic counter ion represented by $A^+$ is an iodonium or sulfonium ion. A sulfonium ion is especially preferred.

As the organic counter ion represented by $A^+$, there can be mentioned the sulfonium ions of general formula (VIII) shown below.

(VIII)

In formula (VIII), each of $R^{1b}$ to $R^{3b}$ independently represents a linear or branched alkyl group having 1 to 30 carbon atoms or a cyclic hydrocarbon group having 3 to 30 carbon atoms. When any one of $R^{1b}$ to $R^{3b}$ is a linear or branched alkyl group, the same may contain as a substituent at least one member selected from among a hydroxyl group, a chain or alicyclic alkoxy group having 1 to 12 carbon atoms and a cyclic hydrocarbon group having 3 to 12 carbon atoms. When any one of $R^{1b}$ to $R^{3b}$ is a cyclic hydrocarbon group, the same may contain as a substituent at least one member selected from among a hydroxyl group, a linear or branched alkyl group having 1 to 12 carbon atoms, a cycloalkyl group and a chain or alicyclic alkoxy group having 1 to 12 carbon atoms.

As the alkyl group, there can be mentioned a methyl group, an ethyl group, an n-propyl group, an isopropyl group, an n-butyl group, a sec-butyl group, a tert-butyl group, a pentyl group, a hexyl group, an octyl group, a 2-ethylhexyl group or the like.

As the alkoxy group, there can be mentioned a methoxy group, an ethoxy group, a propoxy group, a butoxy group, a hexyloxy group, an octyloxy group, a 2-ethylhexyloxy group or the like.

As the cyclic hydrocarbon group, there can be mentioned a cyclopentyl group, a cyclohexyl group, an adamantyl group, a bicyclohexyl group, a phenyl group, a naphthyl group, a fluorenyl group, a biphenyl group or the like.

The sulfonium ions of general formula (IIIa) shown below provide a preferred form of the sulfonium ions of general formula (VIII).

It is preferred for the $A^+$ of general formula (II) to be any of the ions of general formulae (IIIa) to (IIId) shown below.

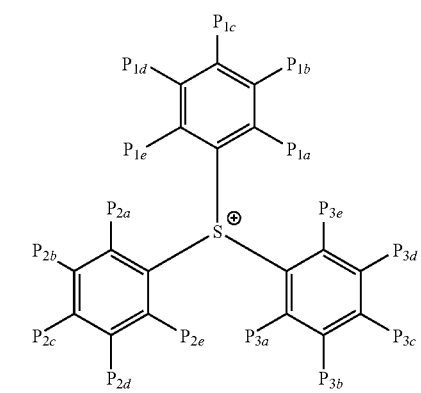

In general formula (IIIa), each of $P_{1a}$ to $P_{1e}$, each of $P_{2a}$ to $P_{2e}$, and each of $P_{3a}$ to $P_{3e}$ independently represents a hydrogen atom, a hydroxyl group, an alkyl group having 1 to 12 carbon atoms, a cycloalkyl group having 3 to 12 carbon atoms or an alkoxy group having 1 to 12 carbon atoms. $P_{1a}$ and $P_{3e}$, $P_{1e}$ and $P_{2a}$, and $P_{2e}$ and $P_{3a}$ may be bonded to each other through a single bond, methylene, an ether bond or a sulfide bond.

The alkyl group may consist of a linear or branched chain. As the alkyl group, there can be mentioned, for example, methyl, ethyl, propyl, butyl, pentyl, hexyl, heptyl, octyl, dodecyl, 2-ethylhexyl, isopropyl, sec-butyl, t-butyl, isoamyl or the like. The alkyl group may have a substituent. As the substituent, there can be mentioned the same groups as can be introduced in the chain alkyl group represented by $R_2$ of general formula (I).

As the cycloalkyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl or the like. Cyclopropyl, cyclopentyl, cyclohexyl, cyclooctyl, norbornyl, adamantyl and noradamantyl are especially preferred. The cycloalkyl group may have a substituent. As the substituent, there can be mentioned the same groups as can be introduced in the chain alkyl group represented by $R_2$ of general formula (I).

The alkoxy group may consist of a linear or branched chain, and further may have an alicyclic skeleton. As the chain alkoxy, there can be mentioned methoxy, ethoxy, propoxy, butoxy, pentyloxy, hexyloxy, heptyloxy, octyloxy, dodecyloxy, 2-ethylhexyloxy, isopropyloxy, sec-butyloxy, t-butyloxy, isoamyloxy or the like. As the cyclic alkoxy, there can be mentioned cyclopropoxy, cyclobutoxy, cyclopentyloxy, cyclohexyloxy, cycloheptyloxy, cyclooctyloxy, cyclododecanyloxy, cyclopentenyloxy, cyclohexenyloxy, cyclooctadienyloxy or the like. Cyclopropoxy, cyclopentyloxy, cyclohexyloxy and cyclooctyloxy are especially preferred. The alkoxy group may have a substituent. As the substituent, there can be mentioned the same groups as can be introduced in the chain alkyl group represented by $R_2$ of general formula (I).

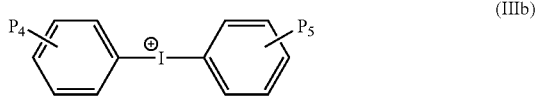

(IIIb)

In formula (IIIb), each of $P_4$ and $P_5$ independently represents a hydrogen atom, a hydroxyl group, an alkyl group having 1 to 12 carbon atoms, a cycloalkyl group having 3 to 12 carbon atoms, an alkoxy group having 1 to 12 carbon atoms or a halogen atom (fluorine, chlorine, bromine or iodine).

The alkyl group may consist of a linear or branched chain. As the alkyl group, there can be mentioned methyl, ethyl, propyl, butyl, pentyl, hexyl, heptyl, octyl, dodecyl, 2-ethylhexyl, isopropyl, sec-butyl, t-butyl, isoamyl or the like. The alkyl group may have a substituent. As the substituent, there can be mentioned the same groups as can be introduced in the chain alkyl group represented by $R_2$ of general formula (I).

As the cycloalkyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl or the like. Cyclopropyl, cyclopentyl, cyclohexyl, cyclooctyl, norbornyl, adamantyl and noradamantyl are especially preferred. The cycloalkyl group may have a substituent. As the substituent, there can be mentioned the same groups as can be introduced in the chain alkyl group represented by $R_2$ of general formula (I).

The alkoxy group may consist of a linear or branched chain, and further may have an alicyclic skeleton. As the chain alkoxy, there can be mentioned methoxy, ethoxy, propoxy, butoxy, pentyloxy, hexyloxy, heptyloxy, octyloxy, dodecyloxy, 2-ethylhexyloxy, isopropyloxy, sec-butyloxy, t-butyloxy, isoamyloxy or the like. As the cyclic alkoxy, there can be mentioned cyclopropoxy, cyclobutoxy, cyclopentyloxy, cyclohexyloxy, cycloheptyloxy, cyclooctyloxy, cyclododecanyloxy, cyclopentenyloxy, cyclohexenyloxy, cyclooctadienyloxy or the like. Cyclopropoxy, cyclopentyloxy, cyclohexyloxy and cyclooctyloxy are especially preferred. The alkoxy group may have a substituent. As the substituent, there can be mentioned the same groups as can be introduced in the chain alkyl group represented by $R_2$ of general formula (I).

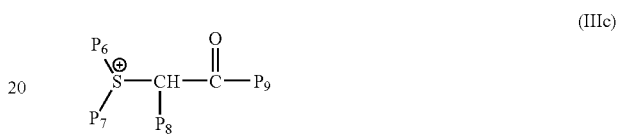

(IIIc)

In formula (IIIc), each of $P_6$ and $P_7$ independently represents an alkyl group having 1 to 12 carbon atoms or a cycloalkyl group having 3 to 12 carbon atoms. $P_6$ and $P_7$ may be bonded to each other so as to form a bivalent hydrocarbon group having 3 to 12 carbon atoms.

$P_8$ represents a hydrogen atom, and $P_9$ represents an alkyl group having 1 to 12 carbon atoms, a cycloalkyl group having 3 to 12 carbon atoms or an aromatic ring group. $P_8$ and $P_9$ may be bonded to each other so as to form a bivalent hydrocarbon group having 3 to 12 carbon atoms.

Any of the carbon atoms contained in the bivalent hydrocarbon group may be substituted with a carbonyl group, an oxygen atom or a sulfur atom.

Each of the alkyl groups represented by $P_6$, $P_7$ and $P_9$ may consist of a linear or branched chain. As the alkyl groups, there can be mentioned methyl, ethyl, propyl, butyl, pentyl, hexyl, heptyl, octyl, dodecyl, 2-ethylhexyl, isopropyl, sec-butyl, t-butyl, isoamyl and the like. Each of the alkyl groups may have a substituent. As the substituent, there can be mentioned the same groups as can be introduced in the chain alkyl group represented by $R_2$ of general formula (I).

As the cycloalkyl groups represented by $P_6$, $P_7$ and $P_9$, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl and the like. Cyclopropyl, cyclopentyl, cyclohexyl, cyclooctyl, norbornyl, adamantyl and noradamantyl are especially preferred. Each of the cycloalkyl groups may have a substituent. As the substituent, there can be mentioned the same groups as can be introduced in the chain alkyl group represented by $R_2$ of general formula (I).

As the aromatic ring group represented by $P_9$, there can be mentioned phenyl, naphthyl, anthracenyl, tetracenyl, biphenyl, phenanthrenyl, furanyl or the like. Phenyl, naphthyl, anthracenyl and the like are preferred. The aromatic ring group may have a substituent. As the substituent, there can be mentioned the same groups as can be introduced in the chain alkyl group represented by $R_2$ of general formula (I).

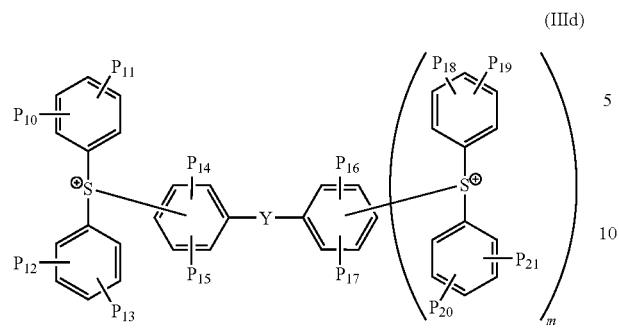

(IIId)

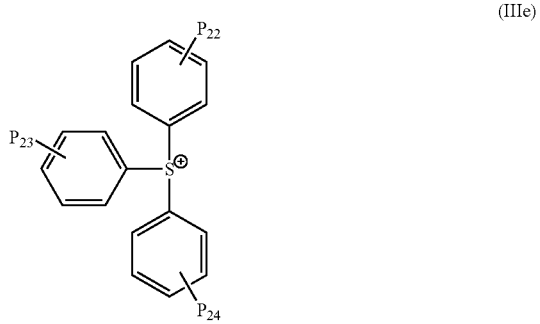

(IIIe)

In the formula, each of $P_{22}$ to $P_{24}$ independently represents a hydrogen atom or an alkyl group having 1 to 4 carbon atoms. The alkyl group may have a substituent.

In formula (IIId), each of $P_{10}$ to $P_{21}$ independently represents a hydrogen atom, a hydroxyl group, an alkyl group having 1 to 12 carbon atoms, a cycloalkyl group having 3 to 12 carbon atoms, an alkoxy group having 1 to 12 carbon atoms or a halogen atom (fluorine, chlorine, bromine or iodine). Y represents a sulfur atom or an oxygen atom, and m is 0 or 1.

The alkyl group may consist of a linear or branched chain. As the alkyl group, there can be mentioned methyl, ethyl, propyl, butyl, pentyl, hexyl, heptyl, octyl, dodecyl, 2-ethylhexyl, isopropyl, sec-butyl, t-butyl, isoamyl or the like. The alkyl group may have a substituent. As the substituent, there can be mentioned the same groups as can be introduced in the chain alkyl group represented by $R_2$ of general formula (I).

As the cycloalkyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl or the like. Cyclopropyl, cyclopentyl, cyclohexyl, cyclooctyl, norbornyl, adamantyl and noradamantyl are especially preferred. The cycloalkyl group may have a substituent. As the substituent, there can be mentioned the same groups as can be introduced in the chain alkyl group represented by $R_2$ of general formula (I).

The alkoxy group may consist of a linear or branched chain, and further may have an alicyclic skeleton. As the chain alkoxy, there can be mentioned methoxy, ethoxy, propoxy, butoxy, pentyloxy, hexyloxy, heptyloxy, octyloxy, dodecyloxy, 2-ethylhexyloxy, isopropyloxy, sec-butyloxy, t-butyloxy, isoamyloxy or the like. As the cyclic alkoxy, there can be mentioned cyclopropoxy, cyclobutoxy, cyclopentyloxy, cyclohexyloxy, cycloheptyloxy, cyclooctyloxy, cyclododecanyloxy, cyclopentenyloxy, cyclohexenyloxy, cyclooctadienyloxy or the like. Cyclopropoxy, cyclopentyloxy, cyclohexyloxy and cyclooctyloxy are especially preferred. The alkoxy group may have a substituent. As the substituent, there can be mentioned the same groups as can be introduced in the chain alkyl group represented by $R_2$ of general formula (I).

The sulfonium ions of general formula (IIIe) shown below provide a preferred form of the sulfonium ions of general formula (IIIa).

The alkyl group may consist of a linear or branched chain. As the alkyl group, there can be mentioned methyl, ethyl, propyl, butyl, pentyl, hexyl, heptyl, octyl, dodecyl, 2-ethylhexyl, isopropyl, sec-butyl, t-butyl, isoamyl or the like. The alkyl group may further have a substituent. As the substituent, there can be mentioned the same groups as can be introduced in the chain alkyl group represented by $R_2$ of general formula (I).

As specific examples of the cations of general formulae (VIII) and (IIIc) to (IIIe), there can be mentioned those of the following formulae.

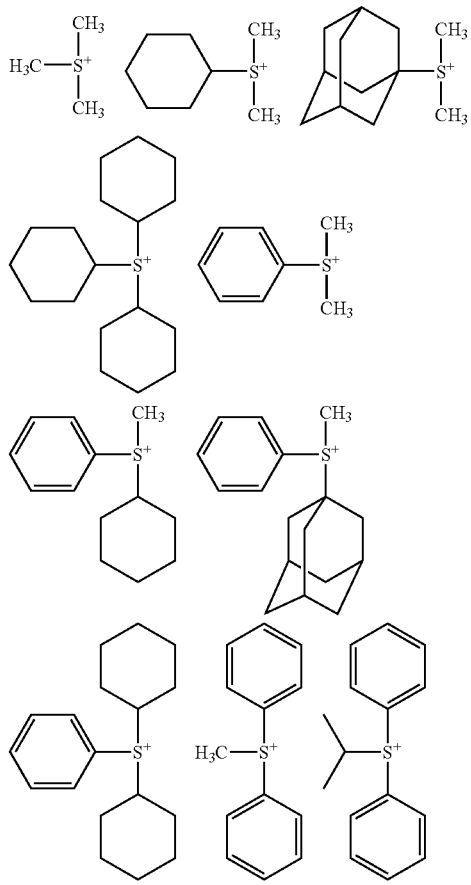

-continued
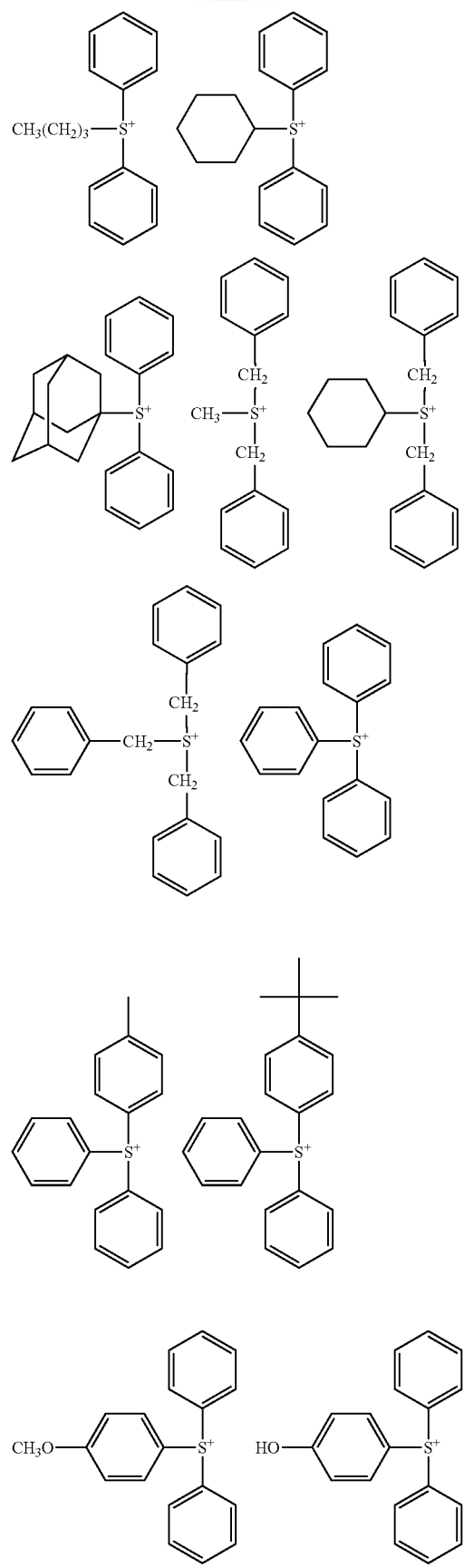
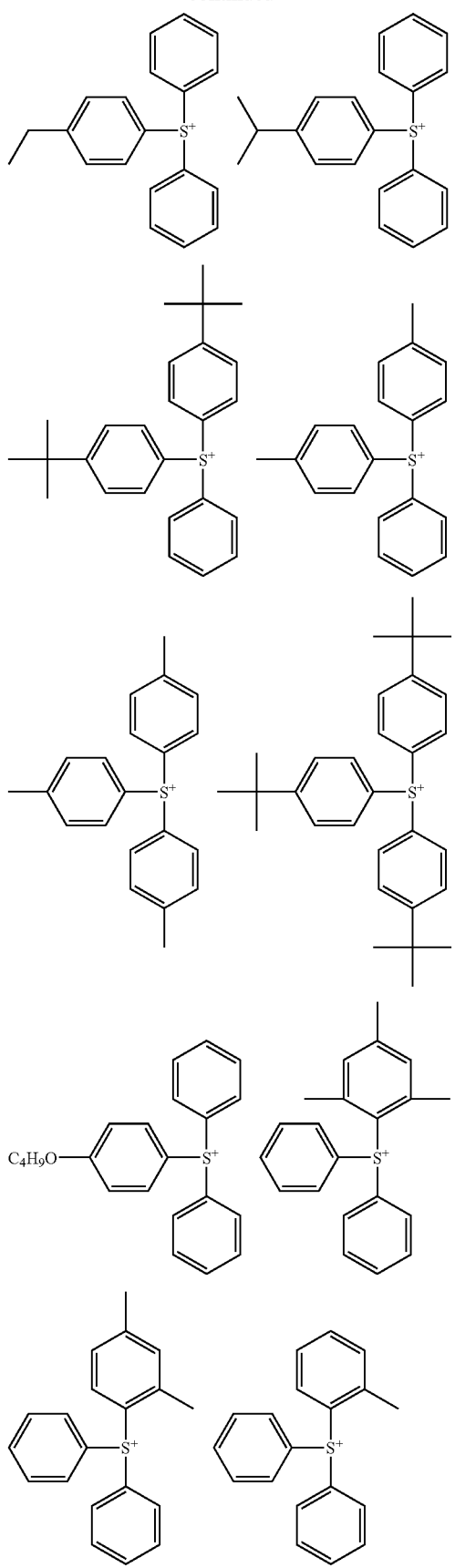

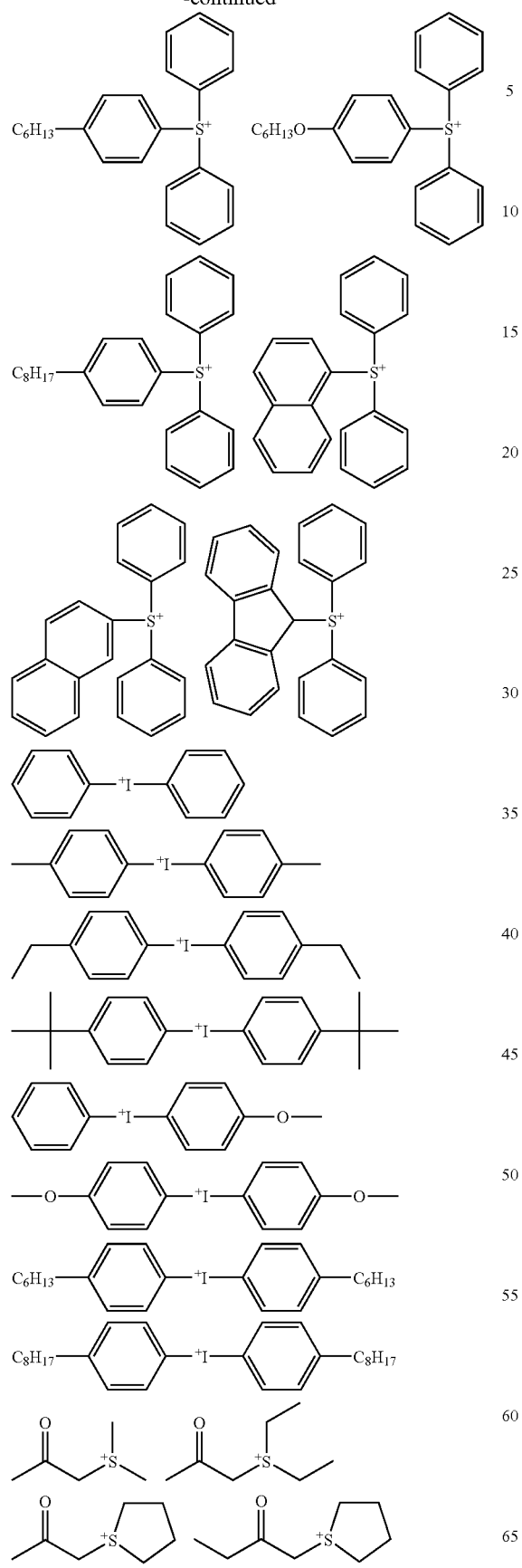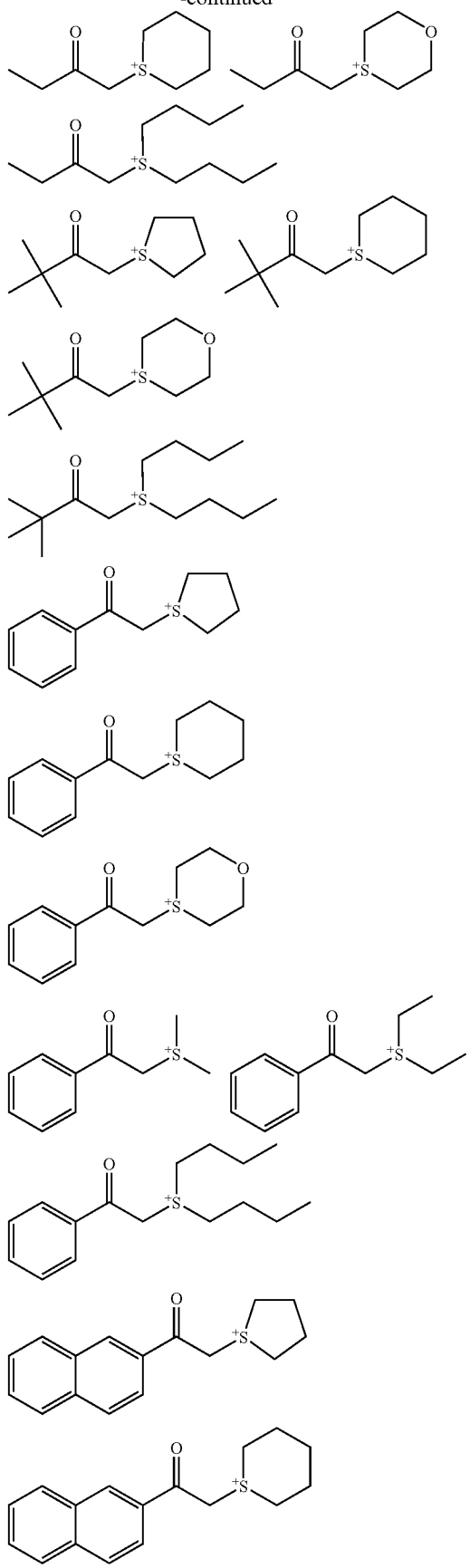

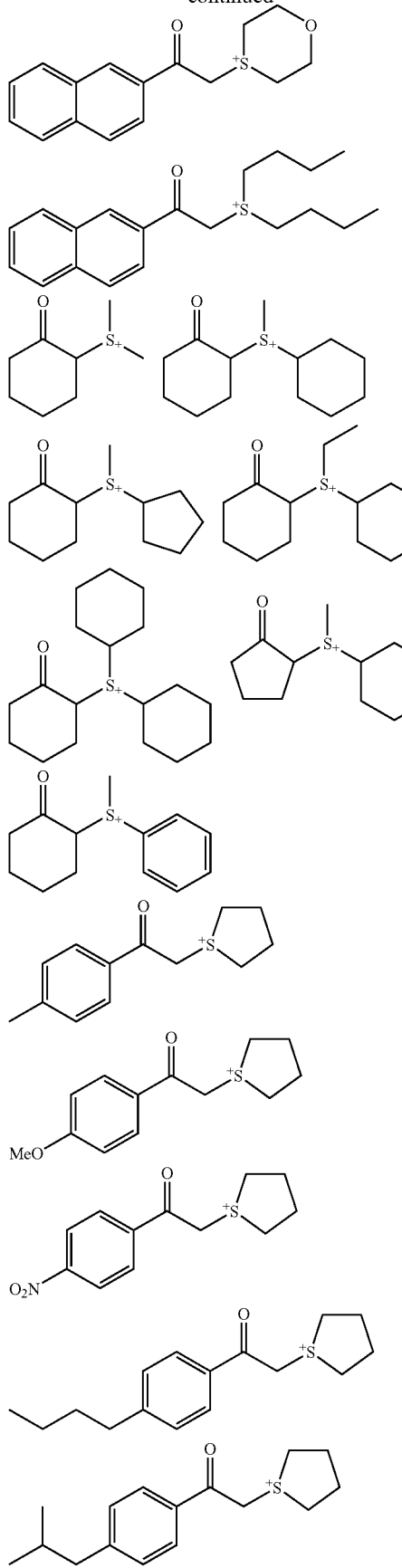
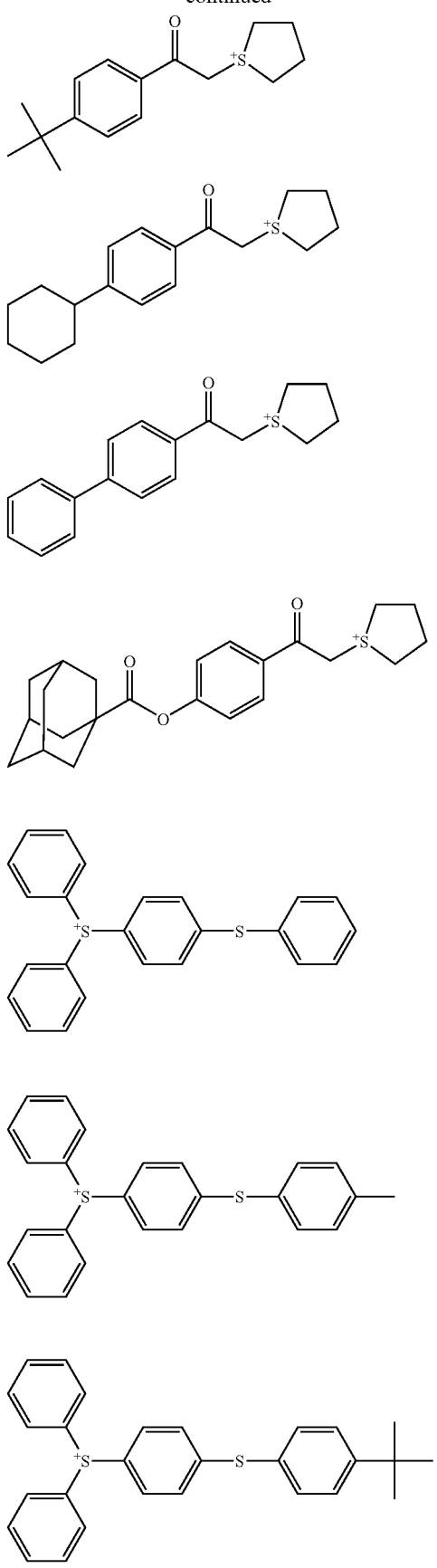

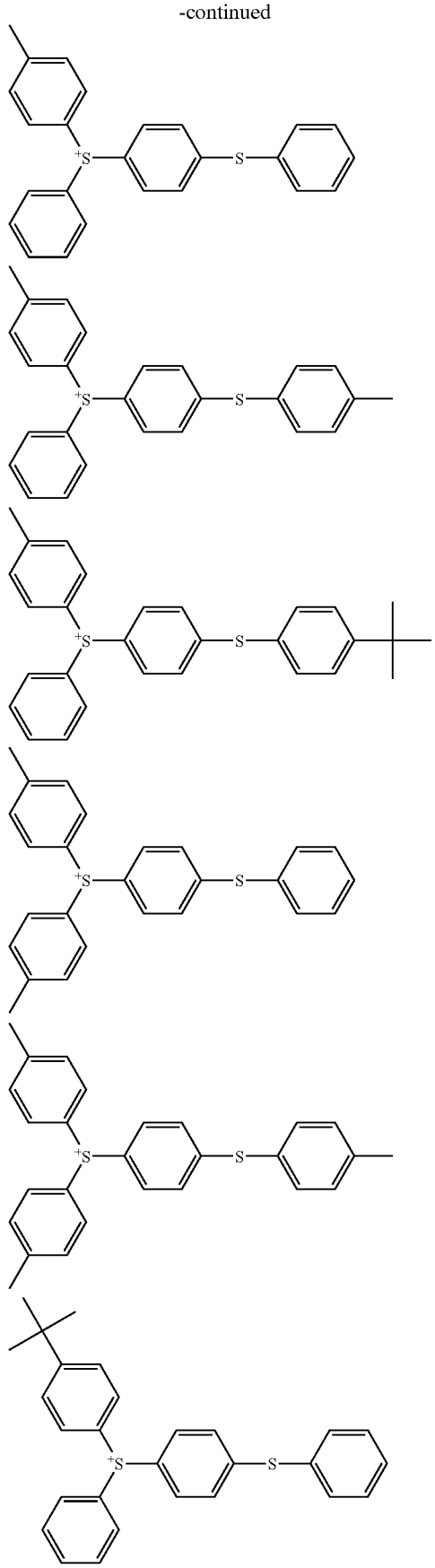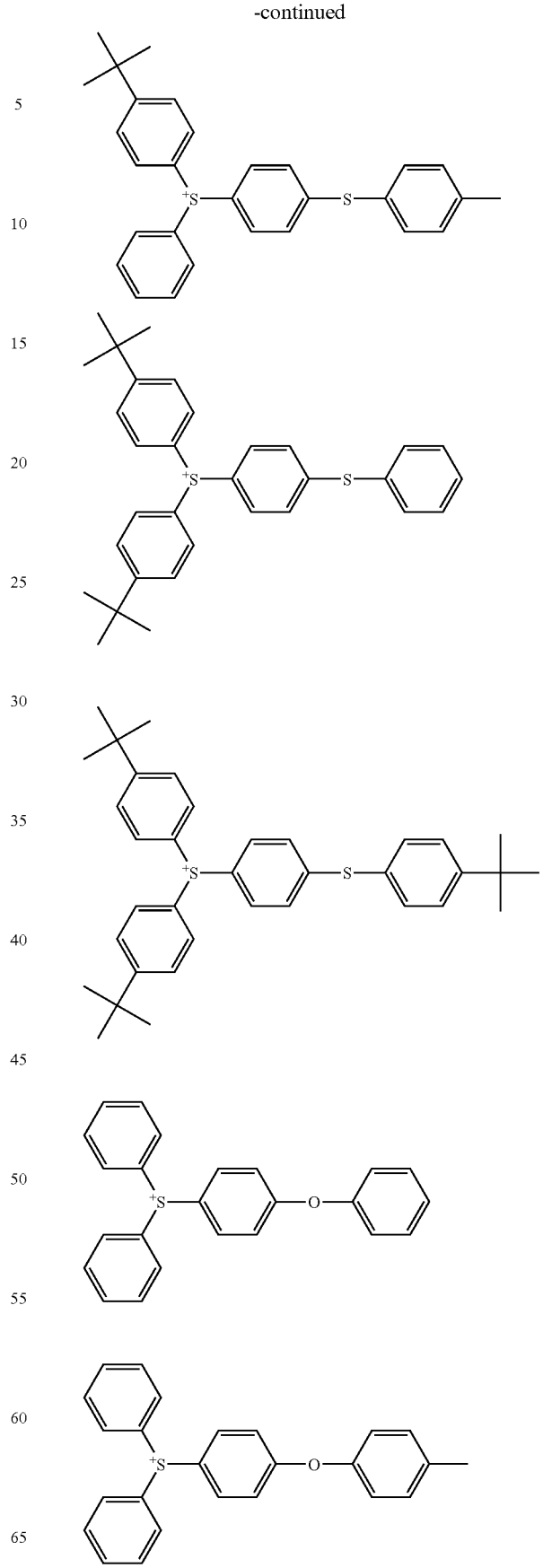

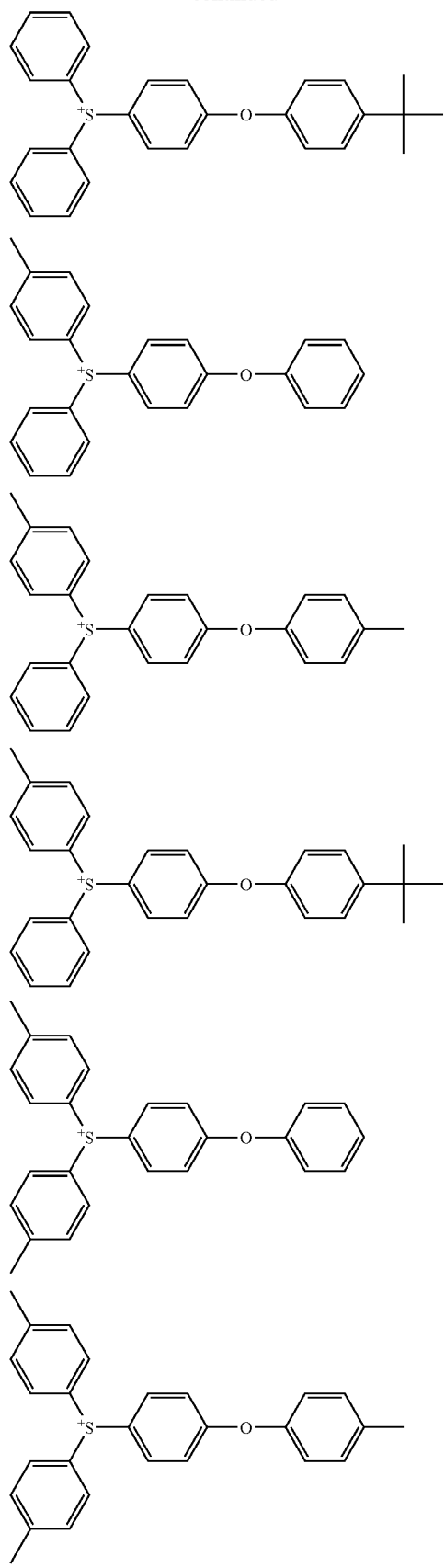
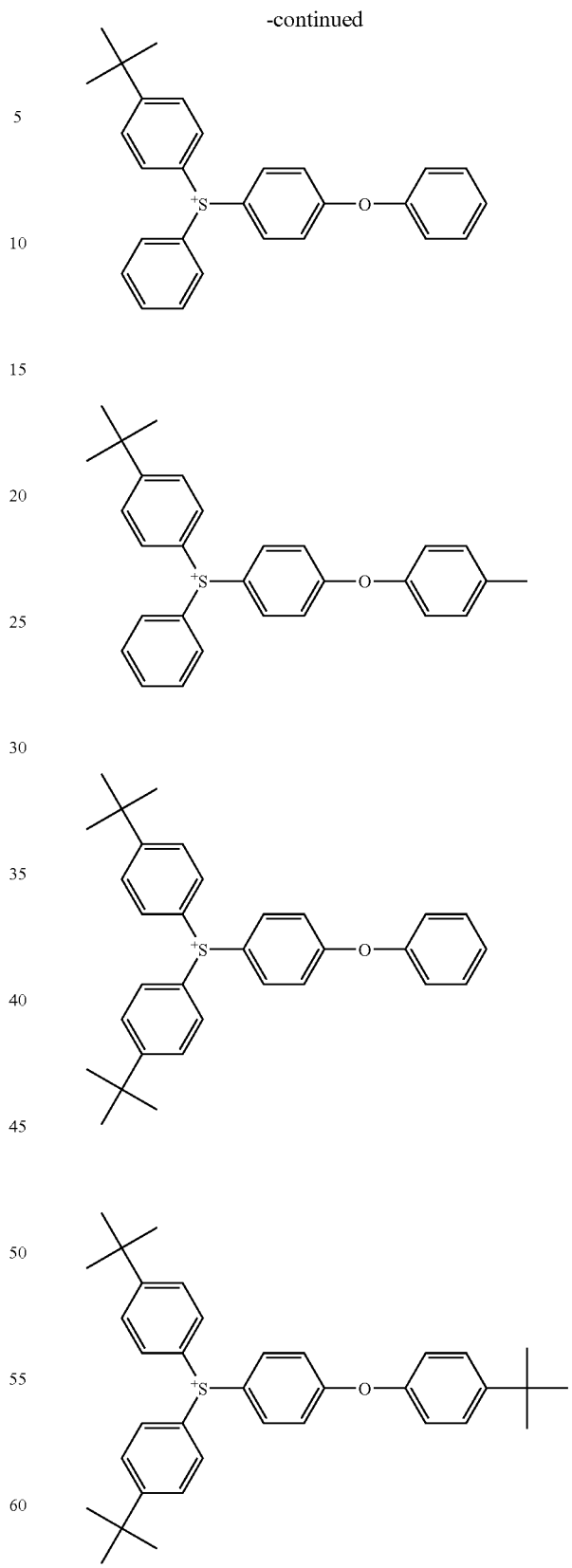
Examples of the compounds capable of generating a sulfonic acid of general formula (I) will be shown below, which however in no way limit the scope of the present invention.

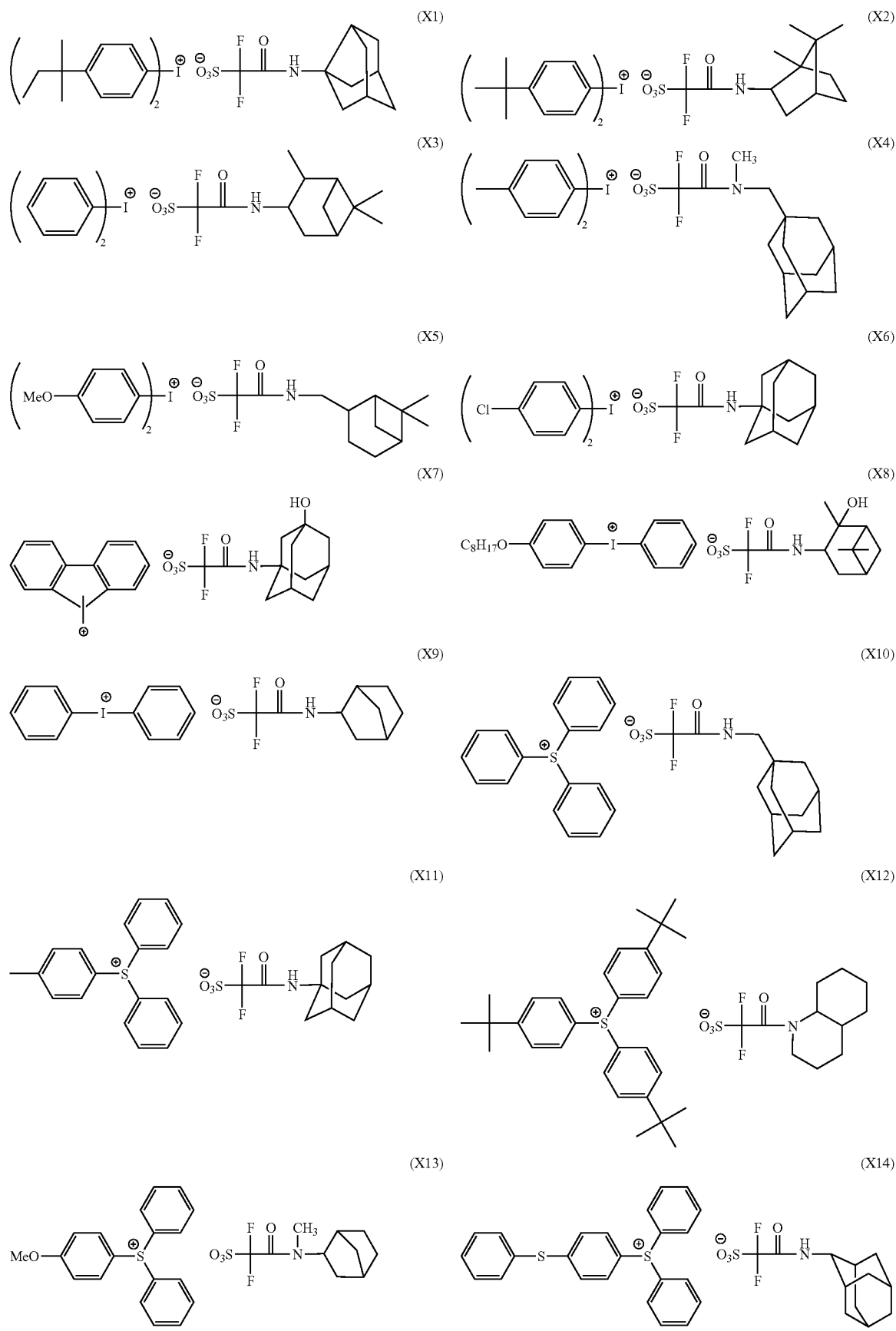

-continued
(X15) 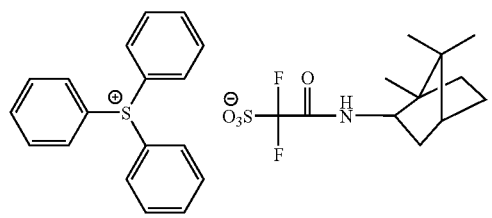
(X16) 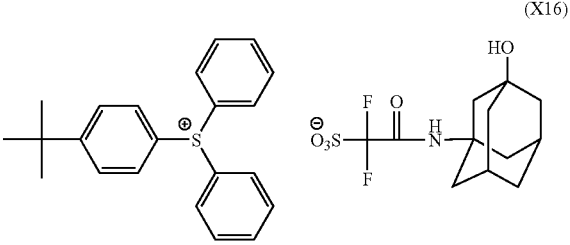
(X17) 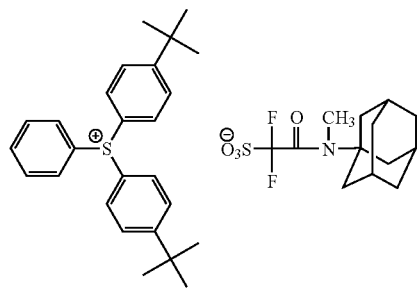
(X18) 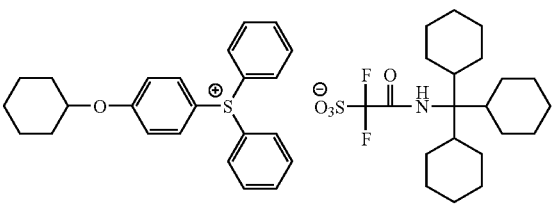
(X19) 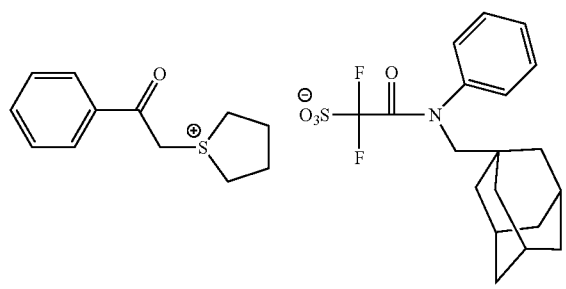
(X20) 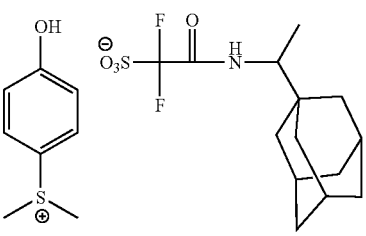
(X21) 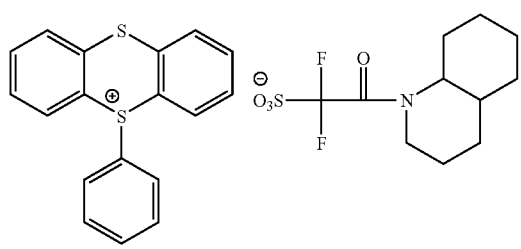
(X22) 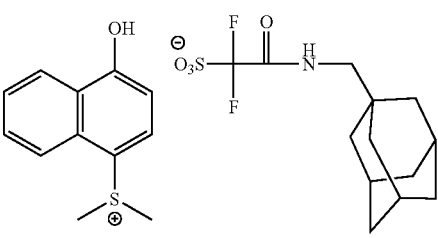
(X23) 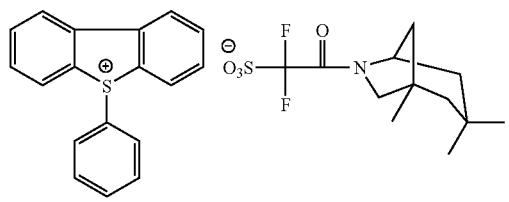
(X24) 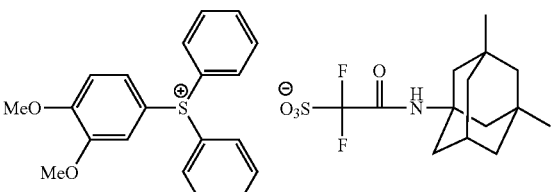
(X25) 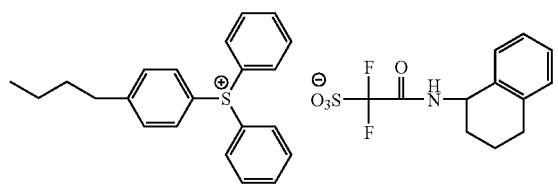
(X26) 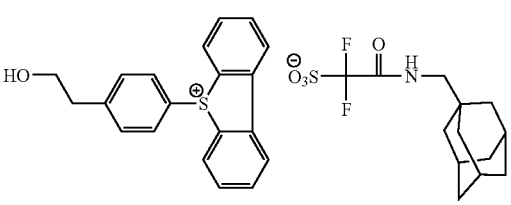

-continued
(X27)
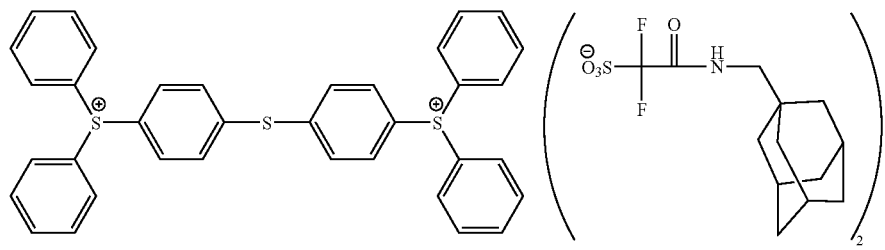
(X28)
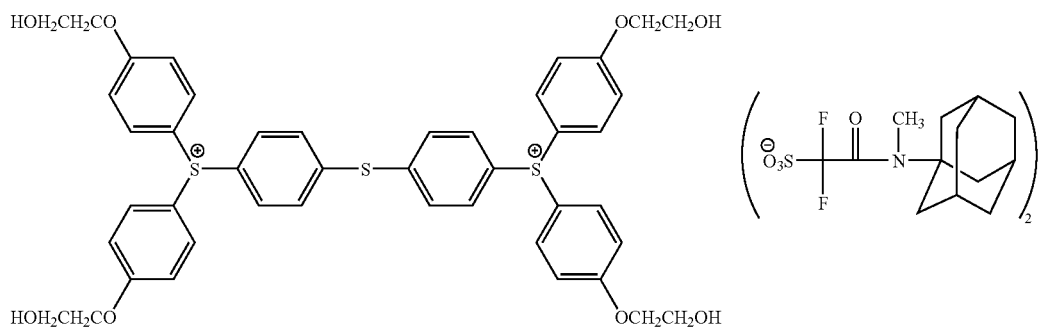
(X29)
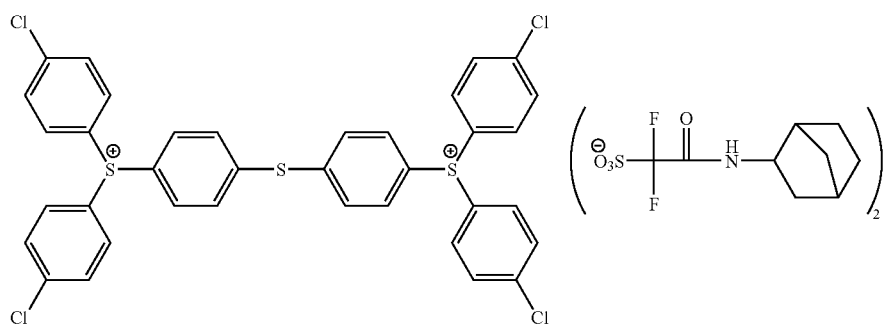
(X30)
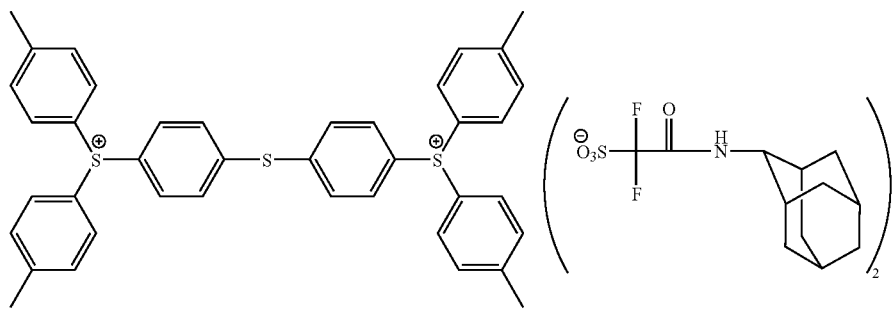
(X31) (X32)
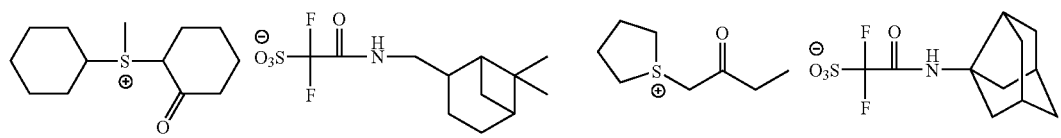
(X33) (X34)
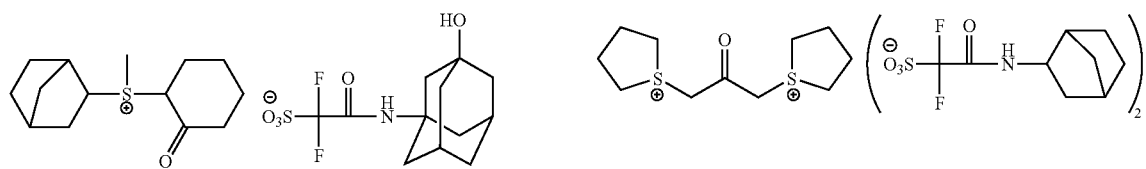

-continued
(X35)
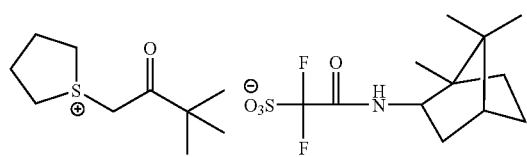
(X36)
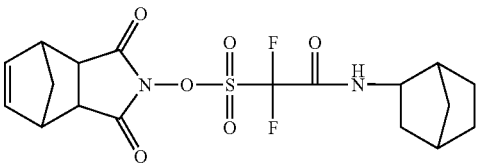
(X37)
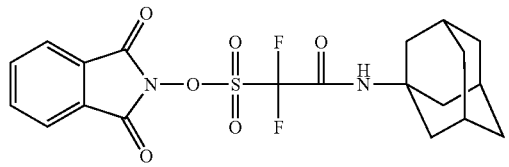
(X38)
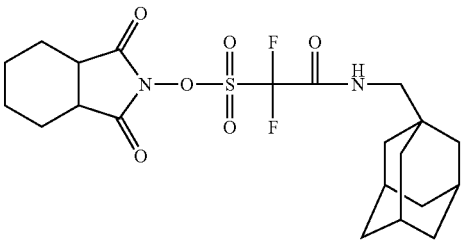
(X39)
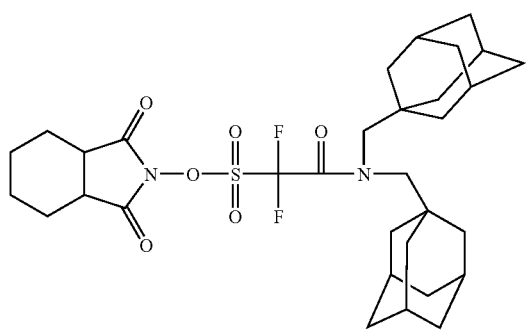
(X40)
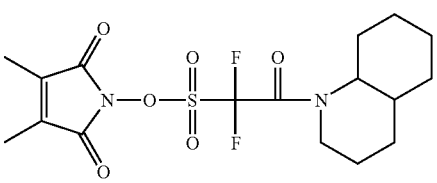
(X41)
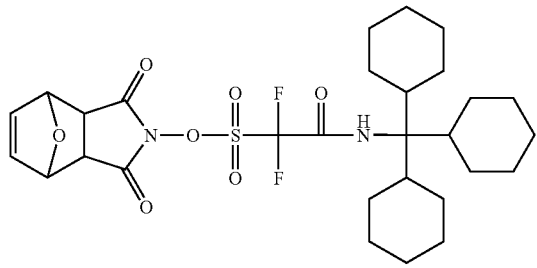
(X42)
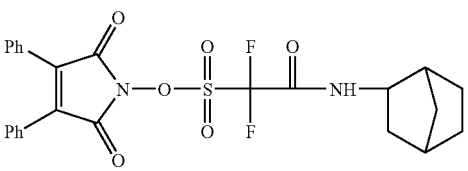
(X43)
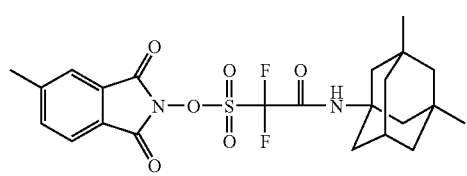
(X44)
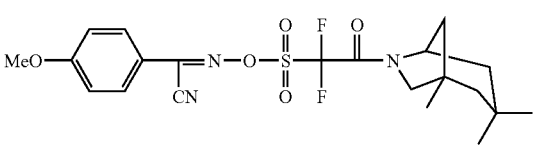
(X45)
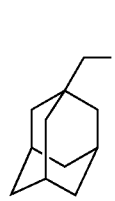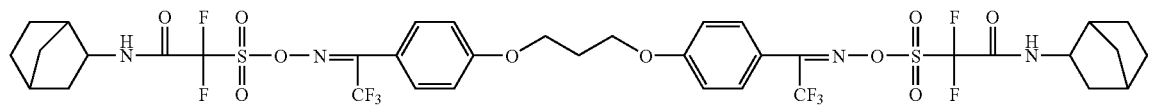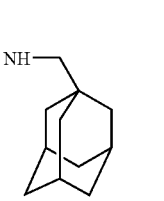
(X46)

-continued

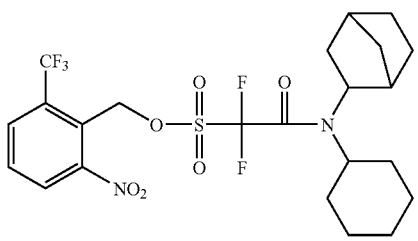
(X47)

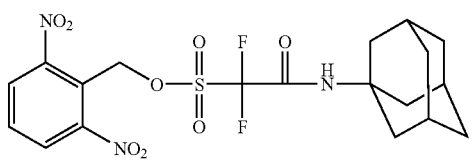
(X48)

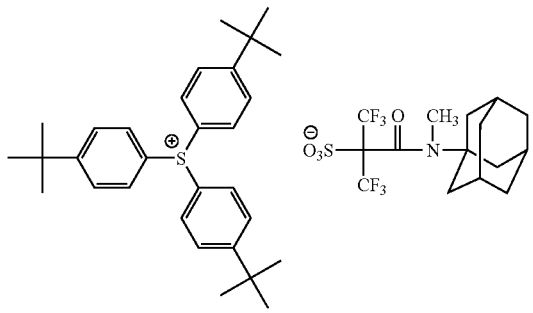
(X49)

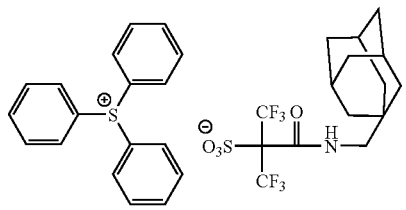
(X50)

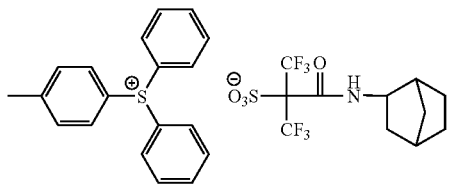
(X51)

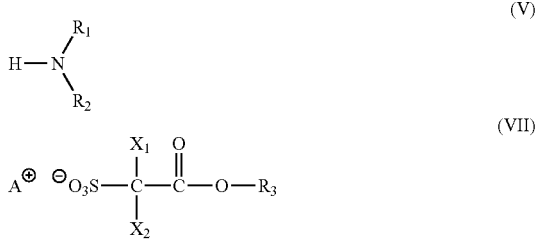
(X52)

The salts of general formula (II) according to the present invention can be obtained by reacting any of the amines of general formula (V) with any of the ester compounds of general formula (VII).

$$H-N\begin{matrix}R_1\\R_2\end{matrix} \quad (V)$$

$$A^{\oplus} \ ^{\ominus}O_3S-\underset{X_2}{\overset{X_1}{C}}-\overset{O}{\overset{\|}{C}}-O-R_3 \quad (VII)$$

In general formula (V), $R_1$ and $R_2$ are as defined above with respect to general formula (II). In general formula (VII), $A^+$, $X_1$ and $X_2$ are as defined above with respect to general formula (II). $R_3$ represents a chain alkyl group, a cycloalkyl group or a group with a polycyclic structure. Each of the chain alkyl group and cycloalkyl group may have a substituent.

The alkyl group represented by $R_3$ may consist of a linear or branched chain. As the alkyl group, there can be mentioned methyl, ethyl, propyl, butyl, pentyl, hexyl, heptyl, octyl, dodecyl, 2-ethylhexyl, isopropyl, sec-butyl, t-butyl, isoamyl or the like. The alkyl group may have a substituent. As the substituent, there can be mentioned the same groups as can be introduced in the chain alkyl group represented by $R_2$ of general formula (I).

As the cycloalkyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl or the like. Cyclopropyl, cyclopentyl, cyclohexyl, cyclooctyl, norbornyl, adamantyl and noradamantyl are especially preferred. The cycloalkyl group may have a substituent. As the substituent, there can be mentioned the same groups as can be introduced in the chain alkyl group represented by $R_2$ of general formula (I).

The group with a polycyclic structure has the same meaning as that represented by $R_1$ in general formula (II). The particular examples and substituents thereof are also the same as mentioned in connection with the same.

The amidation can be achieved by, for example, mixing any of the compounds of general formula (V) with any of the compounds of general formula (VII) and effecting a reaction of the mixture at 0 to 200° C., preferably 0 to 100° C. under agitation. The amidation reaction may be carried out in the absence of any solvent or in the presence of a solvent, such as THF, acetonitrile, acetone, ethyl acetate, dimethylformamide, dimethylacetamide, N-methylpyrrolidone or dimethyl sulfoxide. The mixing ratio of compounds of general formulae (V) and (VII) is not particularly limited. However, it is preferred to use any of the compounds of general formula (V) in an amount of 0.1 to 50 molar equivalents, especially 0.5 to 30 molar equivalents, per molar equivalent of any of the compounds of general formula (VII).

Furthermore, the salts of general formula (II) according to the present invention can be obtained by amidating any of the compounds of general formula (VI) shown below into any of the compounds of general formula (IV) shown below by use of any of the amines of general formula (V) in the same manner as mentioned above and reacting the amidated compound with any of the compounds of general formula (IX).

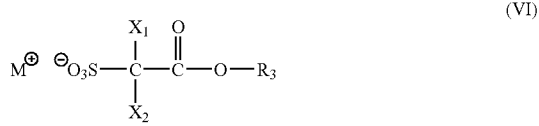
(VI)

In general formula (VI), $M^+$, $X_1$, $X_2$ and $R_3$ are as defined above with respect to general formula (VII).

$M^+$ represents a metal ion. As such, there can be mentioned, for example, a lithium, sodium, potassium or silver ion or the like.

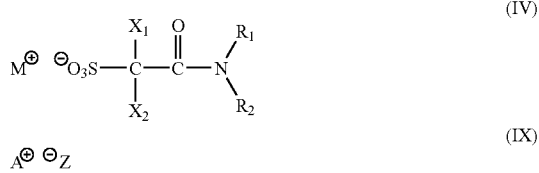
(IV)

(IX)

In general formula (IV), $M^+$ is as defined above with respect to general formula (VI). $X_1$, $X_2$, $R_1$ and $R_2$ are as defined above with respect to general formula (II).

In general formula (IX), $A^+$ is as defined above with respect to general formula (II).

Z represents OH, F, Cl, Br, I, $BF_4$, $AsF_6$, $SbF_6$, $PF_6$ or $ClO_4$.

The compounds of general formula (II) can be obtained by reacting any of the compounds of general formula (IV) with any of the compounds of general formula (IX) in, for example, an inert solvent, such as acetonitrile, water, methanol, chloroform or methylene chloride, at 0 to 150° C. under agitation.

The addition amount of any of the compounds of general formula (IX) relative to that of any of the compounds of general formula (IV) is not particularly limited. However, it is preferred to add any of the compounds of general formula (IX) in an amount of 0.1 to 5 molar equivalents, especially 0.5 to 3 molar equivalents, per molar equivalent of any of the compounds of general formula (IV).

In the positive photosensitive composition of the present invention, use may be made of only one type of photoacid generator (A) or two or more types of photoacid generators (A) in combination. The content thereof based on the total solids of the resist composition is preferably in the range of 0.01 to 40 mass %, more preferably 0.3 to 30 mass %.

Photoacid generator (A) may be used in combination with other photoacid generators. Photoacid generators other than photoacid generator (A) will be described below.

[Other Photoacid Generator]

In the present invention, photoacid generator (A) according to the present invention may be used in combination with other compounds that are decomposed upon exposure to actinic rays or radiation to thereby generate acids. The amount of photoacid generator used in combination with photoacid generator (A) according to the present invention in terms of molar ratio (photoacid generator (A) according to the present invention/other photoacid generator) is generally in the range of 100/0 t0 20/80, preferably 100/0 to 40/60 and more preferably 100/0 t0 50/50. As such a photoacid generator employed in combination, use can be made of a member appropriately selected from among a photoinitiator for photocationic polymerization, a photoinitiator for photoradical polymerization, a photo-achromatic agent and photo-discoloring agent of dyes, any of publicly known compounds that when exposed to actinic rays or radiation, generate an acid, are employed in microresists, etc., and mixtures thereof.

For example, as the photoacid generator, there can be mentioned a diazonium salt, a phosphonium salt, a sulfonium salt, an iodonium salt, an imide sulfonate, an oxime sulfonate, diazosulfone, disulfone or o-nitrobenzyl sulfonate.

Further, use can be made of compounds obtained by introducing any of the above groups or compounds that when exposed to actinic rays or radiation, generate an acid in a polymer principal chain or side chain, for example, compounds described in U.S. Pat. No. 3,849,137, DE 3914407, JP-A's-63-26653, 55-164824, 62-69263, 63-146038, 63-163452, 62-153853, 63-146029, etc.

Furthermore, use can be made of compounds that when exposed to light, generate an acid described in U.S. Pat. No. 3,779,778 and EP 126,712.

As preferred compounds among the acid generators, there can be mentioned those of the following general formulae (ZI), (ZII) and (ZIII).

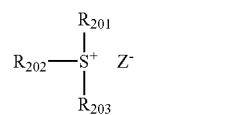
ZI

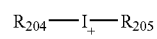
ZII

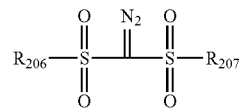
ZIII

In the above general formula (ZI), each of R201, R202 and R203 independently represents an organic group.

The number of carbon atoms of the organic group represented by R201, R202 and R203 is generally in the range of 1 to 30, preferably 1 to 20.

Two of R201 to R203 may be bonded with each other to thereby form a ring structure, and the ring within the same may contain an oxygen atom, a sulfur atom, an ester bond, an amido bond or a carbonyl group. As the group formed by bonding of two of R201 to R203, there can be mentioned an alkylene group (for example, a butylene group or a pentylene group).

Z— represents a nonnucleophilic anion.

As the nonnucleophilic anion represented by Z—, there can be mentioned, for example, a sulfonate anion, a carboxylate anion, a sulfonylimido anion, a bis(alkylsulfonyl)imido anion, a tris(alkylsulfonyl)methyl anion or the like.

The nonnucleophilic anion means an anion whose capability of inducing a nucleophilic reaction is extremely low and is an anion capable of inhibiting any temporal decomposition by intramolecular nucleophilic reaction. This would realize an enhancement of the temporal stability of the resist.

As the sulfonate anion, there can be mentioned, for example, an aliphatic sulfonate anion, an aromatic sulfonate anion, a camphor sulfonate anion or the like.

As the carboxylate anion, there can be mentioned, for example, an aliphatic carboxylate anion, an aromatic carboxylate anion, an aralkyl carboxylate anion or the like.

The aliphatic moiety of the aliphatic sulfonate anion may be an alkyl group or a cycloalkyl group, being preferably an alkyl group having 1 to 30 carbon atoms or a cycloalkyl group having 3 to 30 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a boronyl group or the like.

As a preferred aromatic group of the aromatic sulfonate anion, there can be mentioned an aryl group having 6 to 14 carbon atoms, for example, a phenyl group, a tolyl group, a naphthyl group or the like. The alkyl group, cycloalkyl group and aryl group of the aliphatic sulfonate anion and aromatic sulfonate anion may have a substituent. As the substituent of the alkyl group, cycloalkyl group and aryl group of the aliphatic sulfonate anion and aromatic sulfonate anion, there can be mentioned, for example, a nitro group, a halogen atom (fluorine atom, chlorine atom, bromine atom or iodine atom), a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) or the like. The aryl group or ring structure of these groups may further have an alkyl group (preferably having 1 to 15 carbon atoms) as its substituent.

As the aliphatic moiety of the aliphatic carboxylate anion, there can be mentioned the same alkyl groups and cycloalkyl groups as mentioned with respect to the aliphatic sulfonate anion.

As the aromatic group of the aromatic carboxylate anion, there can be mentioned the same aryl groups as mentioned with respect to the aromatic sulfonate anion.

As a preferred aralkyl group of the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

The alkyl group, cycloalkyl group, aryl group and aralkyl group of the aliphatic carboxylate anion, aromatic carboxylate anion and aralkyl carboxylate anion may have a substituent. As the substituent of the alkyl group, cycloalkyl group, aryl group and aralkyl group of the aliphatic carboxylate anion, aromatic carboxylate anion and aralkyl carboxylate anion, there can be mentioned, for example, the same halogen atom, alkyl group, cycloalkyl group, alkoxy group, alkylthio group, etc. as mentioned with respect to the aromatic sulfonate anion.

As the sulfonylimido anion, there can be mentioned, for example, a saccharin anion.

The alkyl group of the bis(alkylsulfonyl)imido anion and tris(alkylsulfonyl)methyl anion is preferably an alkyl group having 1 to 5 carbon atoms. As such, there can be mentioned, for example, a methyl group, an ethyl group, a propyl group, an isopropyl group, an n-butyl group, an isobutyl group, a sec-butyl group, a pentyl group, a neopentyl group or the like. As a substituent of these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group or the like. An alkyl group substituted with a fluorine atom is preferred.

As the other nonnucleophilic anions, there can be mentioned, for example, phosphorus fluoride, boron fluoride, antimony fluoride and the like.

The nonnucleophilic anion represented by Z— is preferably selected from among an aliphatic sulfonate anion substituted at its α-position of sulfonic acid with a fluorine atom, an aromatic sulfonate anion substituted with a fluorine atom or a group having a fluorine atom, a bis(alkylsulfonyl)imido anion whose alkyl group is substituted with a fluorine atom and a tris(alkylsulfonyl)methide anion whose alkyl group is substituted with a fluorine atom. More preferably, the nonnucleophilic anion is a perfluorinated aliphatic sulfonate anion having 4 to 8 carbon atoms or a benzene sulfonate anion having a fluorine atom. Still more preferably, the nonnucleophilic anion is a nonafluorobutane sulfonate anion, a perfluorooctane sulfonate anion, a pentafluorobenzene sulfonate anion or a 3,5-bis(trifluoromethyl)benzene sulfonate anion.

The nonnucleophilic anion represented by $Z^-$ may have any of the structures of general formulae Xa and Xb shown below.

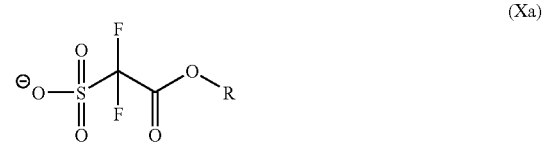

(Xa)

In general formula (Xa), R represents a hydrogen atom or an organic group. The organic group preferably has 1 to 40 carbon atoms, more preferably 3 to 20 carbon atoms and most preferably any of the groups of formula (XI) shown below.

The organic group represented by R essentially has 1 or more carbon atoms. Preferably, the atom bonded to the oxygen atom of the ester bond appearing in general formula (Xa) is a carbon atom. As the organic group, there can be mentioned, for example, an alkyl group, a cycloalkyl group, an aryl group, an aralkyl group or a group with a lactone structure. The organic group in its chain may have a heteroatom, such as an oxygen atom or a sulfur atom. The heteroatom may be introduced as a substituent, and the organic group may have a substituent, such as a hydroxyl group, an acyl group, an acyloxy group, an oxy group (=O) or a halogen atom.

(XI)

In formula (XI), Rc represents a cyclic organic group of a single ring or multiple rings having 3 to 30 carbon atoms that may contain a cyclic ether, cyclic thioether, cyclic ketone, cyclic carbonic ester, lactone or lactam structure. Y represents a hydroxyl group, a halogen atom, a cyano group, a carboxyl group, a hydrocarbon group having 1 to 10 carbon atoms, a hydroxyalkyl group having 1 to 10 carbon atoms, an alkoxy group having 1 to 10 carbon atoms, an acyl group having 1 to 10 carbon atoms, an alkoxycarbonyl group having 2 to 10 carbon atoms, an acyloxy group having 2 to 10 carbon atoms, an alkoxyalkyl group having 2 to 10 carbon atoms or a halogenated alkyl group having 1 to 8 carbon atoms. In the formula, m is 0 to 6. In the event of multiple Ys, they may be identical to or different from each other. Further, n is 0 to 10.

The sum of carbon atoms constructing each of the groups R of formula (XI) is preferably 40 or less.

It is preferred for the organic group to be a monocyclic or polycyclic organic group of n 0 to 3 and Rc 7 to 16.

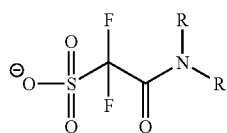

(Xb)

In general formula (Xb), each of Rs represents a hydrogen atom or an organic group without any polycyclic skeleton. Preferably, each of Rs represents a hydrogen atom or an organic group without any polycyclic skeleton having 1 to 40 carbon atoms. More preferably, each of Rs represents a hydrogen atom or an organic group without any polycyclic skeleton having 3 to 20 carbon atoms. Rs may be different from each other, and may be bonded to each other to thereby form a ring. The organic group represented by Rs essentially has 1 or more carbon atoms. Preferably, the atom bonded to the nitrogen atom of the amido bond appearing in general formula (Xb) is a carbon atom. As the organic group, there can be mentioned, for example, an alkyl group, cycloalkyl group, aryl group, aralkyl group or group with a lactone structure each having no polycyclic skeleton. The organic group in its chain may have a heteroatom, such as an oxygen atom or a sulfur atom. The heteroatom may be introduced as a substituent, and the organic group may have a substituent, such as a hydroxyl group, an acyl group, an acyloxy group, an oxy group (=O) or a halogen atom.

The molecular weight of each of the nonnucleophilic anion moieties of general formulae (Xa) and (Xb) is generally in the range of 300 to 1000, preferably 400 to 800 and more preferably 500 to 700.

As the organic groups represented by R201, R202 and R203, there can be mentioned, for example, groups corresponding to the following compounds (ZI-1), (ZI-2) and (ZI-3).

Appropriate use may be made of compounds with two or more of the structures of the general formula (ZI). For example, use may be made of compounds having a structure wherein at least one of R201 to R203 of a compound of the general formula (ZI) is bonded with at least one of R201 to R203 of another compound of the general formula (ZI).

As preferred (ZI) components, there can be mentioned the following compounds (ZI-1), (ZI-2) and (ZI-3).

The compounds (ZI-1) are arylsulfonium compounds of the general formula (ZI) wherein at least one of R201 to R203 is an aryl group, namely, compounds containing an arylsulfonium as a cation.

In the arylsulfonium compounds, all of the R201 to R203 may be aryl groups. It is also appropriate that the R201 to R203 are partially an aryl group and the remainder is an alkyl group or a cycloalkyl group.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by R201 to R203 may have as its substituent an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three R201 to R203, or alternatively may be contained in all three of 8201 to R203. When R201 to R203 represent an aryl group, the substituent preferably lies at the p-position of the aryl group.

Now, the compounds (ZI-2) will be described.

The compounds (ZI-2) are compounds of the formula (ZI) wherein each of R201 to R203 independently represents an organic group having no aromatic ring. The aromatic rings include an aromatic ring having a heteroatom.

The organic group having no aromatic ring represented by R201 to R203 generally has 1 to 30 carbon atoms, preferably 1 to 20 carbon atoms.

Preferably, each of R201 to R203 independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by R201 to R203, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (for example, a cyclopentyl group, a cyclohexyl group or a norbornyl group). As more preferred alkyl groups, there can be mentioned a 2-oxoalkyl group and an alkoxycarbonylmethyl group. As more preferred cycloalkyl group, there can be mentioned a 2-oxocycloalkyl group.

The 2-oxoalkyl group may be linear or branched. A group having >C=O at the 2-position of the alkyl group is preferred.

The 2-oxocycloalkyl group is preferably a group having >C=O at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The R201 to R203 may be further substituted with a halogen atom, an alkoxy group (for example, 1 to 5 carbon atoms), a hydroxyl group, a cyano group or a nitro group.

The compounds (ZI-3) are those represented by the following general formula (ZI-3) which have a phenacylsulfonium salt structure.

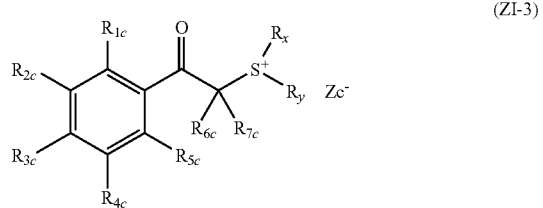

(ZI-3)

In the general formula (ZI-3), each of R1c to R5c independently represents a hydrogen atom, an alkyl group, a cycloalkyl group, an alkoxy group or a halogen atom.

Each of R6c and R7c independently represents a hydrogen atom, an alkyl group or a cycloalkyl group.

Each of Rx and Ry independently represents an alkyl group, a cycloalkyl group, an allyl group or a vinyl group.

Any two or more of R1c to R5c, and R6c and R7c, and Rx and Ry may be bonded with each other to thereby form a ring structure. This ring structure may contain an oxygen atom, a sulfur atom, an ester bond or an amido bond. As the group formed by bonding of any two or more of R1c to R5c, and R6c and R7c, and Rx and Ry, there can be mentioned a butylene group, a pentylene group or the like.

Zc- represents a nonnucleophilic anion. There can be mentioned the same nonnucleophilic anions as mentioned with respect to the Z— of the general formula (ZI).

The alkyl group represented by R1c to R7c may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by R1c to R5c may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

Preferably, any one of R1c to R5c is a linear or branched alkyl group, a cycloalkyl group or a linear, branched or cyclic alkoxy group. More preferably, the sum of carbon atoms of R1c to R5c is in the range of 2 to 15. Accordingly, there can be attained an enhancement of solvent solubility and inhibition of particle generation during storage.

As the alkyl groups and cycloalkyl groups represented by Rx and Ry, there can be mentioned the same alkyl groups and cycloalkyl groups as mentioned with respect to R1c to R7c. Among them, a 2-oxoalkyl group, a 2-oxocycloalkyl group and an alkoxycarbonylmethyl group are preferred.

As the 2-oxoalkyl group and 2-oxocycloalkyl group, there can be mentioned groups having >C=O at the 2-position of the alkyl group and cycloalkyl group represented by R1c to R7c.

Regarding the alkoxy group of the alkoxycarbonylmethyl group, there can be mentioned the same alkoxy groups as mentioned with respect to R1c to R5c.

Each of Rx and Ry is preferably an alkyl group or cycloalkyl group having preferably 4 or more carbon atoms. The alkyl group or cycloalkyl group has more preferably 6 or more carbon atoms and still more preferably 8 or more carbon atoms.

In the general formulae (ZII) and (ZIII), each of R204 to R207 independently represents an aryl group, an alkyl group or a cycloalkyl group.

The aryl group represented by R204 to R207 is preferably a phenyl group or a naphthyl group, more preferably a phenyl group. The aryl group represented by R204 to R207 may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

As preferred alkyl groups and cycloalkyl groups represented by R204 to R207, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The aryl group, alkyl group and cycloalkyl group represented by R204 to R207 may have a substituent. As a possible substituent on the aryl group, alkyl group and cycloalkyl group represented by R204 to R207, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group or the like.

Z— represents a nonnucleophilic anion. As such, there can be mentioned the same nonnucleophilic anions as mentioned with respect to the Z— of the general formula (ZI).

As the acid generators, there can be further mentioned the compounds of the following general formulae (ZIV), (ZV) and (ZVI).

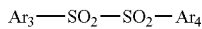   ZIV

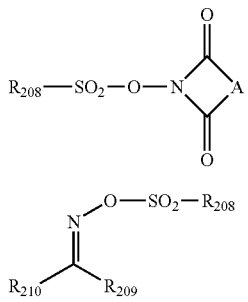

ZV

ZVI

In the general formulae (ZIV) to (ZVI), each of Ar3 and Ar4 independently represents an aryl group.

Each of R208, R209 and R210 independently represents an alkyl group, a cycloalkyl group or an aryl group.

A represents an alkylene group, an alkenylene group or an arylene group.

Among the acid generators, the compounds of the general formulae (ZI) to (ZIII) are more preferred.

As a preferred acid generator, there can be mentioned a compound that generates an acid having one sulfonate group or imido group. As a more preferred acid generator, there can be mentioned a compound that generates a monovalent perfluoroalkanesulfonic acid, a compound that generates a monovalent aromatic sulfonic acid substituted with a fluorine atom or fluorine-atom-containing group, or a compound that generates a monovalent imidic acid substituted with a fluorine atom or fluorine-atom-containing group. As a still more preferred acid generator, there can be mentioned any of sulfonium salts of fluorinated alkanesulfonic acid, fluorinated benzenesulfonic acid, fluorinated imidic acid and fluorinated methide acid. With respect to practicable acid generators, it is especially preferred for the generated acid to be a fluorinated alkanesulfonic acid, fluorinated benzenesulfonic acid or fluorinated imidic acid of -1 or below pKa. By the use thereof, an enhancement of sensitivity can be attained.

Especially preferred examples of the acid generators are as follows.

(z1)

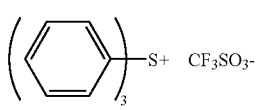

(z2)

(z3)

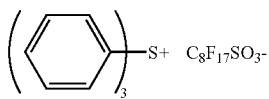

(z4)

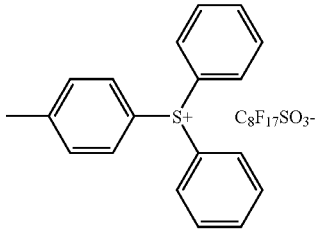

(z5)

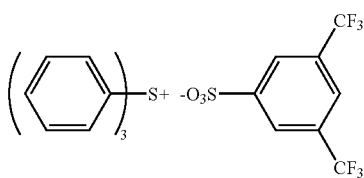

(z6)

(z7)

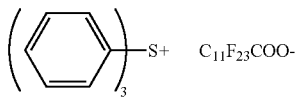

(z8)

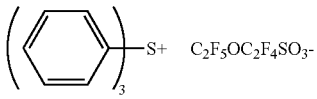

(z9)

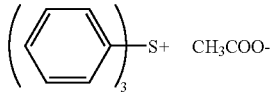

(z10)

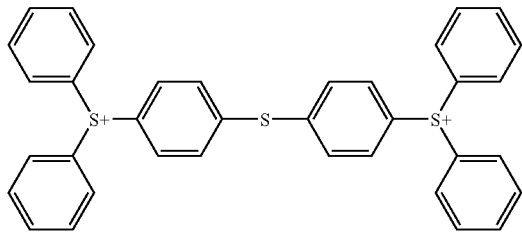

-continued
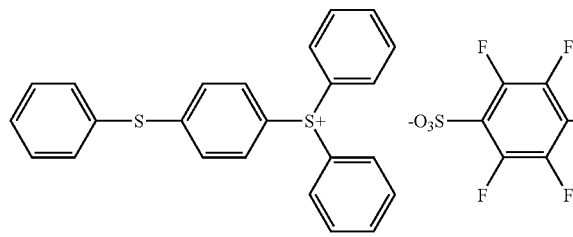 (z11)
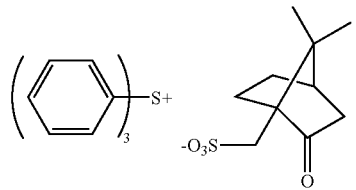 (z12)
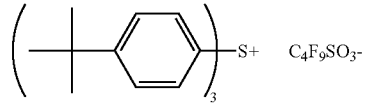 (z13)
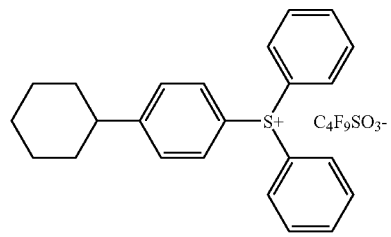 (z14)
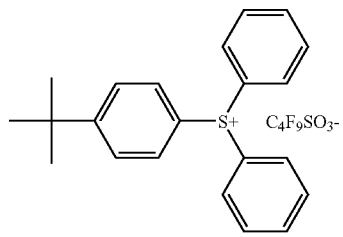 (z15)
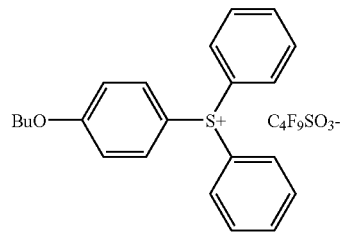 (z16)
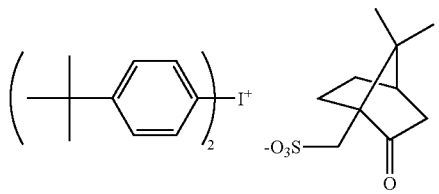 (z17)
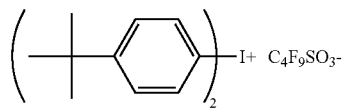 (z18)
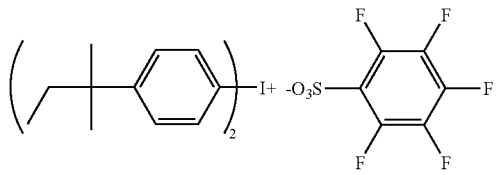 (z19)
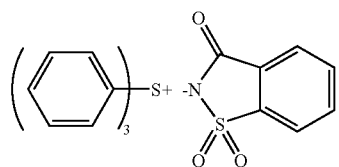 (z20)
 (z21)
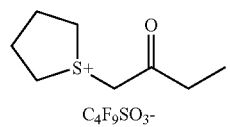 (z22)
 (z23)
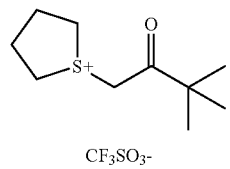 (z24)
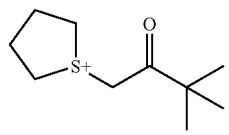 (z25)

-continued
| (z26) | (z27) |
|---|---|
| 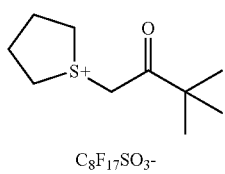<br>C$_8$F$_{17}$SO$_3^-$ | 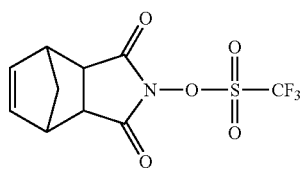 |
| (z28) | (z29) |
| 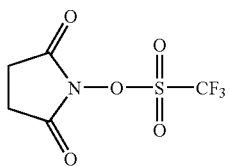 | 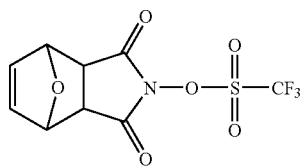 |
| (z30) | (z31) |
| 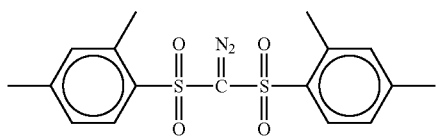 | 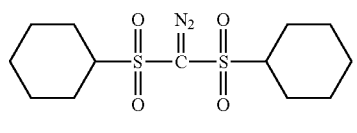 |
| (z32) | (z33) |
| 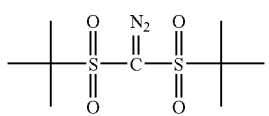 | 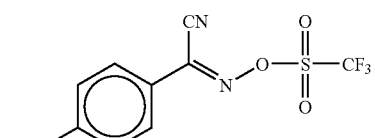 |
(z34)
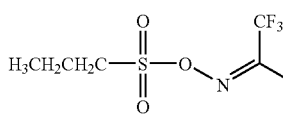
| (z35) | (z36) |
|---|---|
| 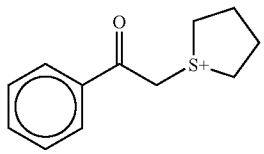<br>CF$_3$SO$_3^-$ | 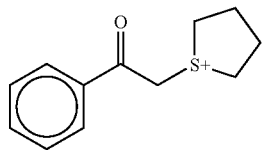<br>C$_4$F$_9$SO$_3^-$ |
| (z37) | (z38) |
| 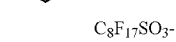<br>C$_8$F$_{17}$SO$_3^-$ | 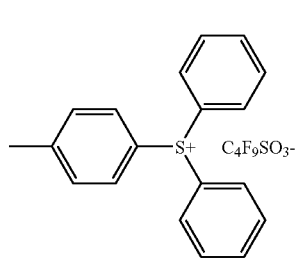 C$_4$F$_9$SO$_3^-$ |
| (z39) | (z40) |
| 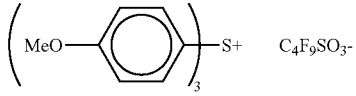 C$_4$F$_9$SO$_3^-$ | 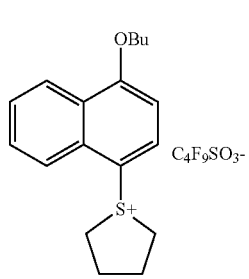 |

-continued
(z41) 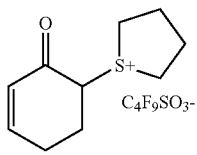
(z42) 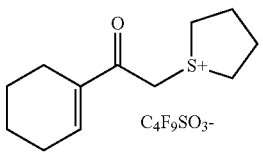
(z43) 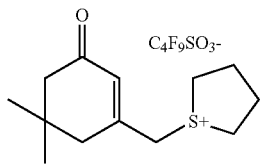
(z44) 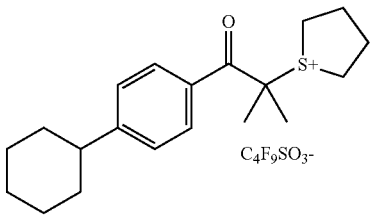
(z45) 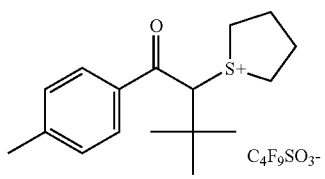
(z46) 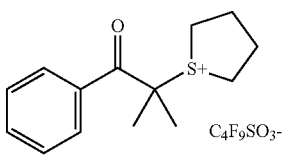
(z47) 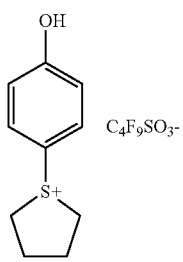
(z48) 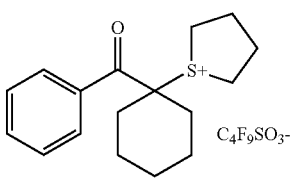
(z49) 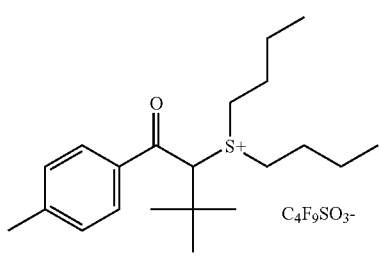
(z50) 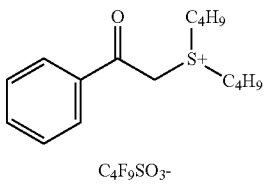
(z51) 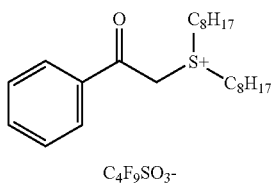
(z52) 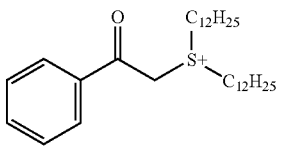
(z53) 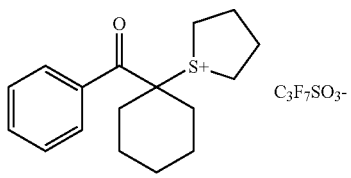
(z54) 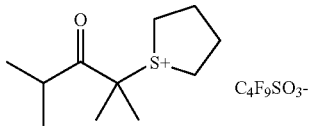

-continued
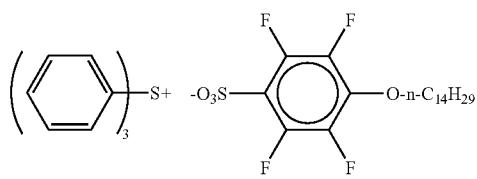
(z55)
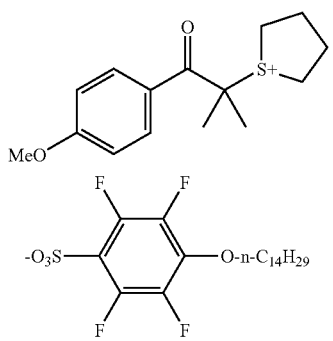
(z56)
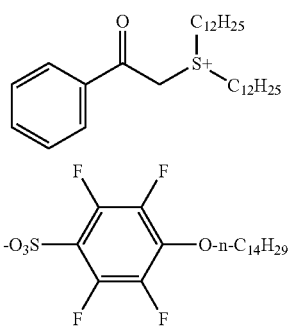
(z57)
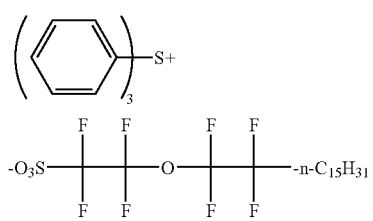
(z58)
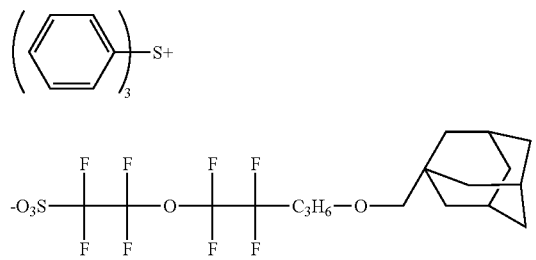
(z59)
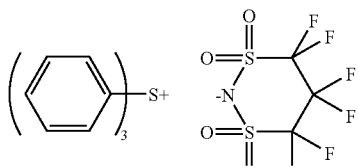
(z60)
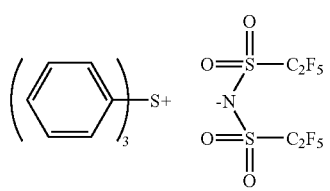
(z61)
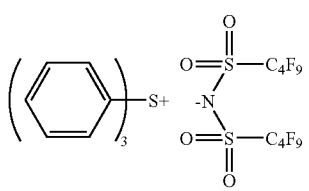
(z62)
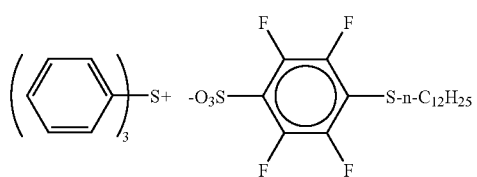
(z63)
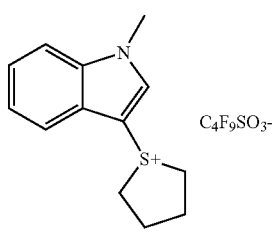
(z64)
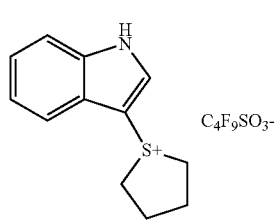
(z65)
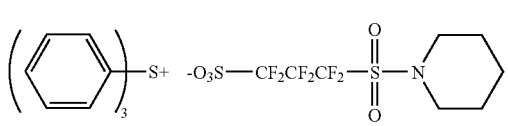
(z66)

-continued
(z67) 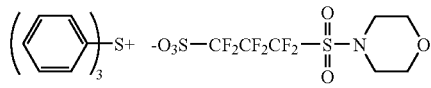
(z68) 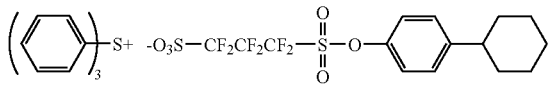
(z69) 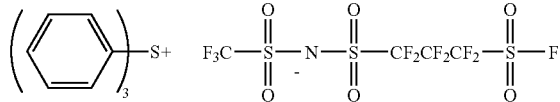
(z70) 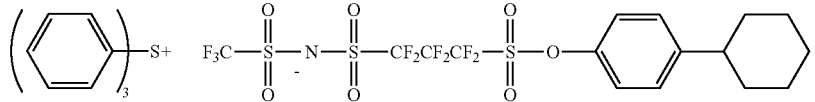
(z71) 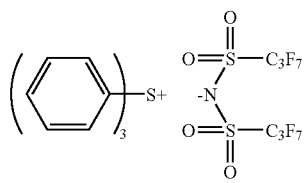
(z72) 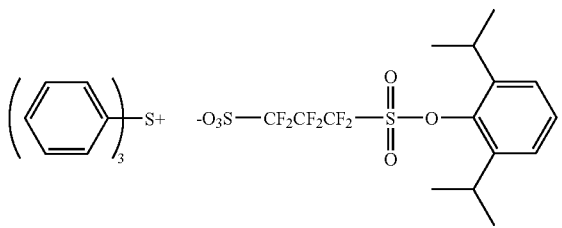
(z73) 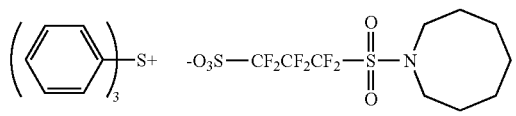
(z74) 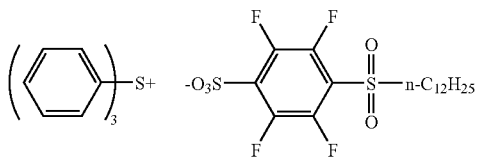
(z75) 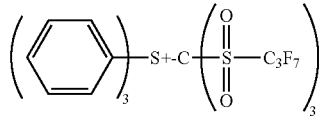
(z76) 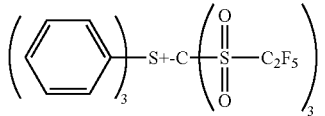
(z77) 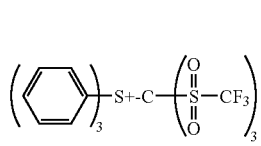
(z78) 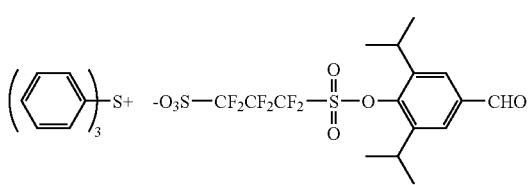
(z79) 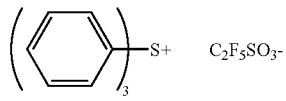
(z80) 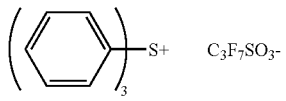
(z81) 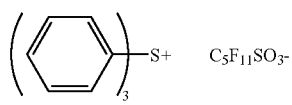
(z82) 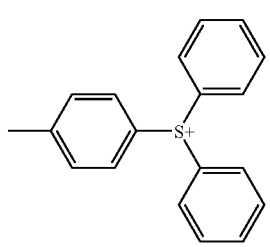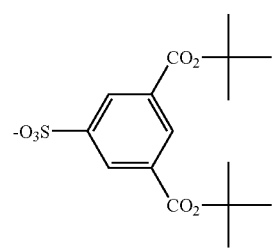

-continued
(z83) 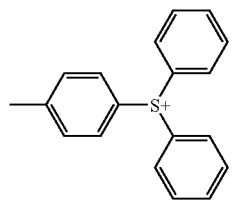 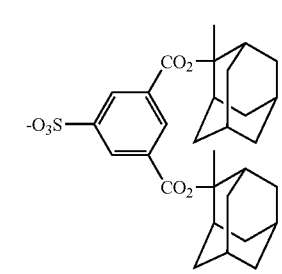
(z84) 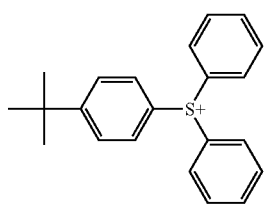 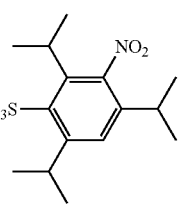
(z85) 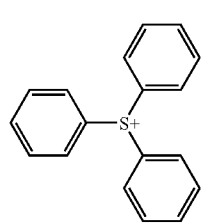 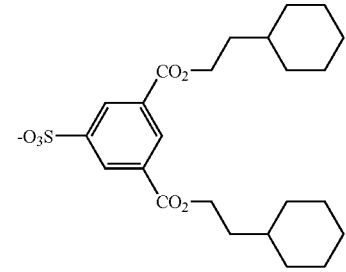
(z86) 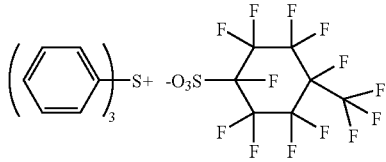
(z87) 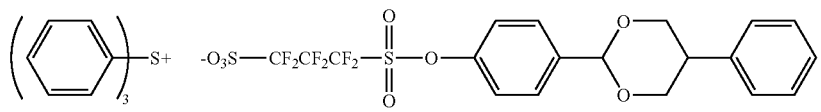
(z88) 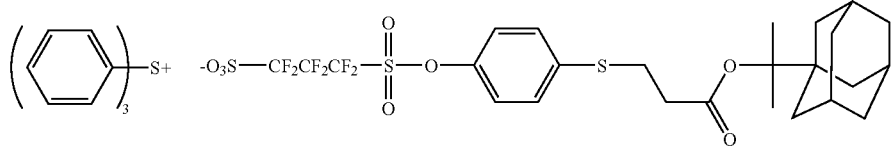
(z89) 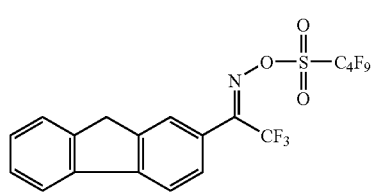
(z90) 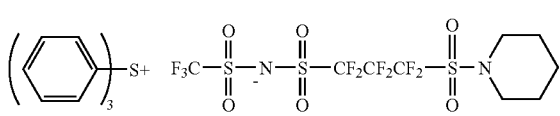
(z91) 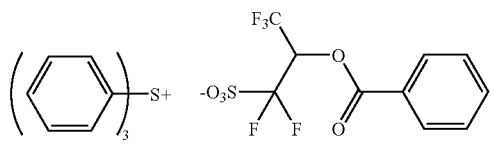
(Y-1) 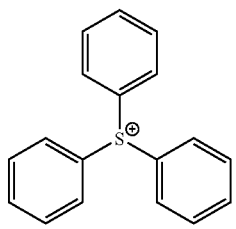
(Y-2) 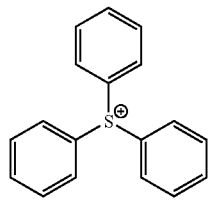
(Y-3) 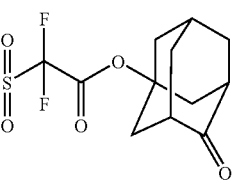
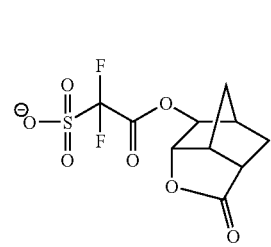
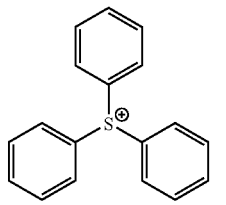
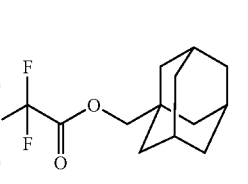

-continued
(Y-4)
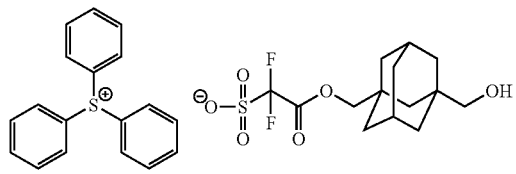
(Y-5)
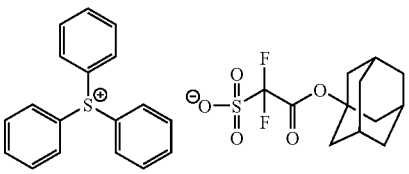
(Y-6)
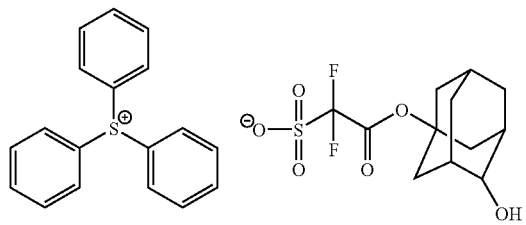
(Y-7)
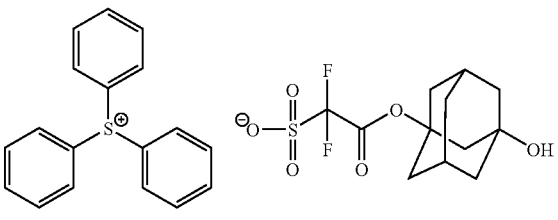
(Y-8)
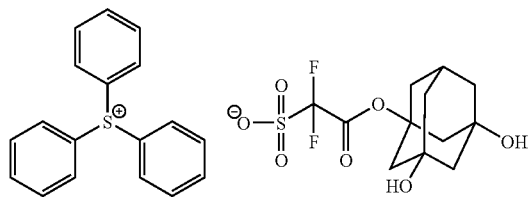
(Y-9)
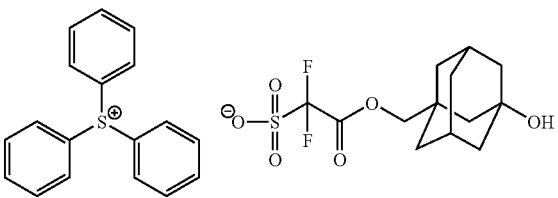
(Y-10)
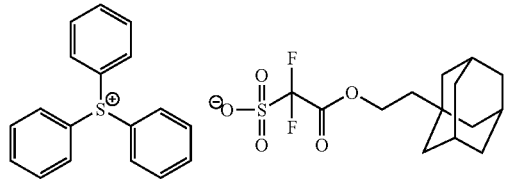
(Y-11)
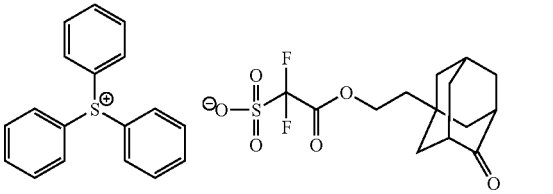
(Y-12)
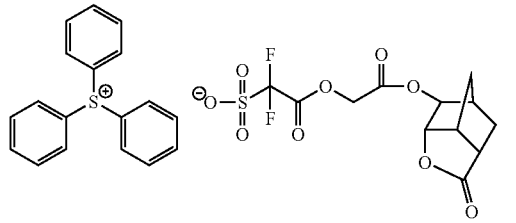
(Y-13)
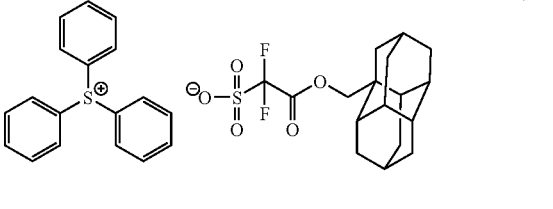
(Y-14)
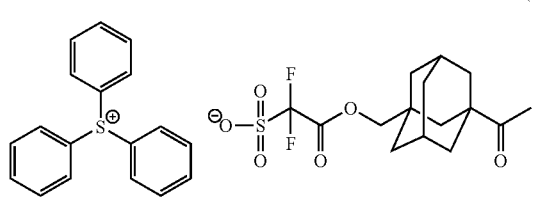
(Y-15)
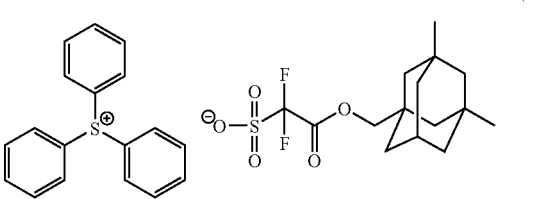
(Y-16)
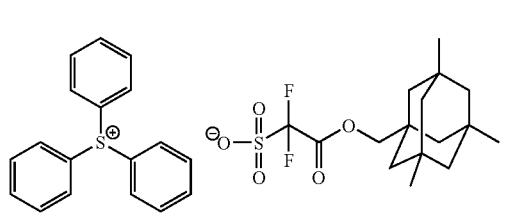
(Y-17)
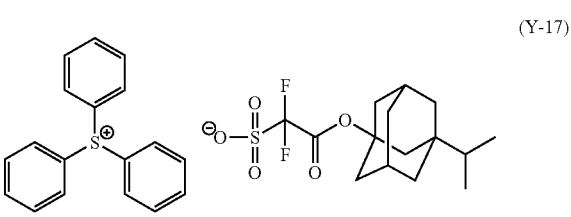

-continued
(Y-18) 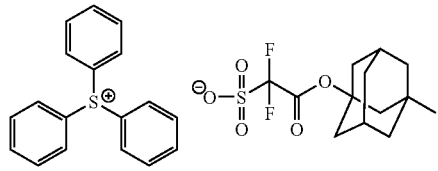
(Y-19) 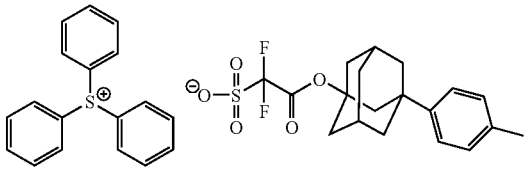
(Y-20) 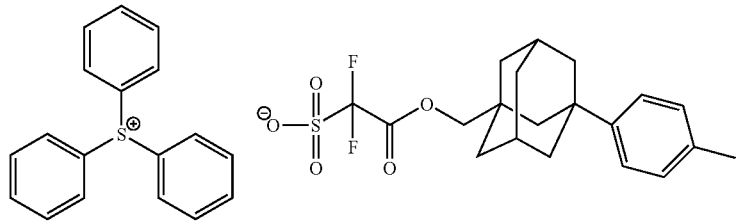
(Y-21) 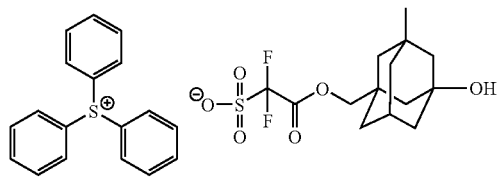
(Y-21) 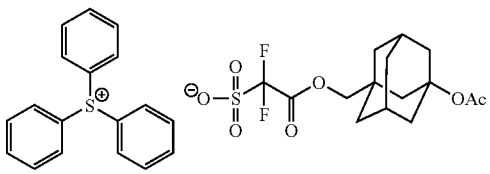
(Y-22) 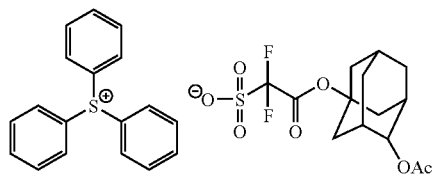
(Y-23) 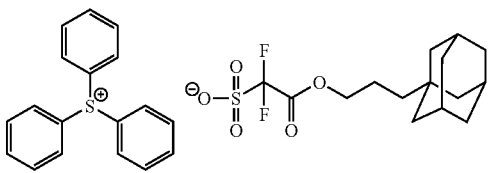
(Y-24) 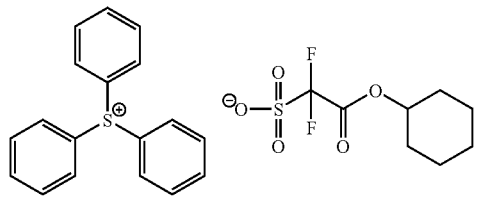
(Y-25) 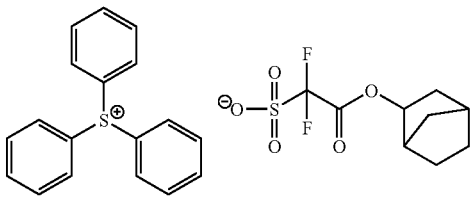
(Y-26) 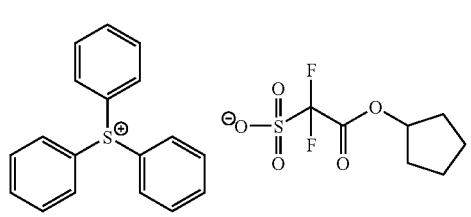
(Y-27) 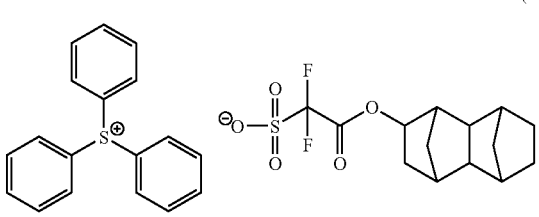
(Y-28) 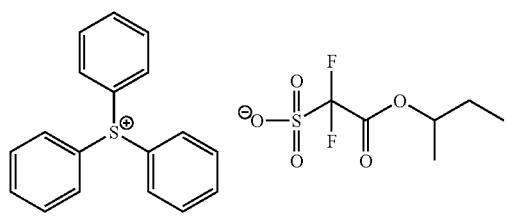
(Y-29) 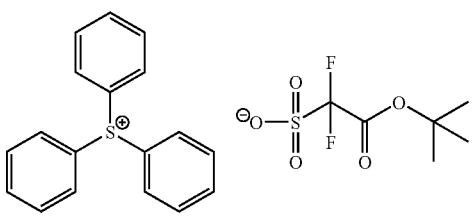

-continued
(Y-30) 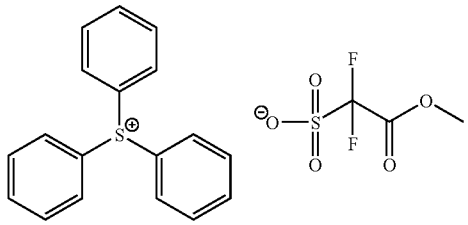
(Y-31) 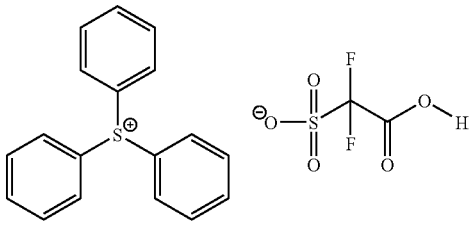
(Y-32) 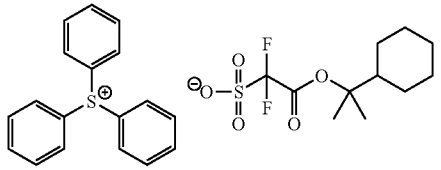
(Y-33) 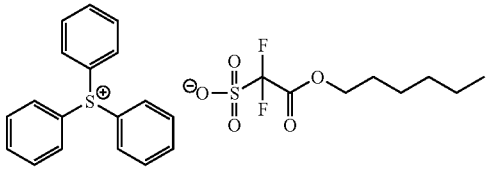
(Y-34) 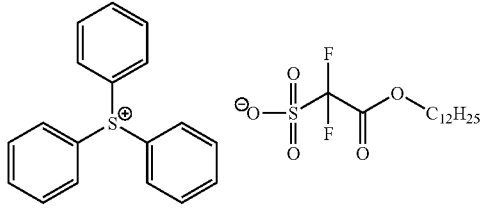
(Y-35) 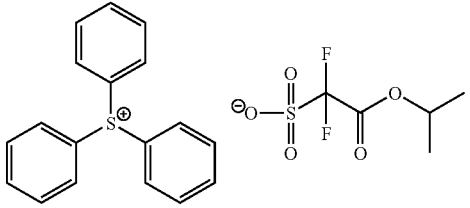
(Y-36) 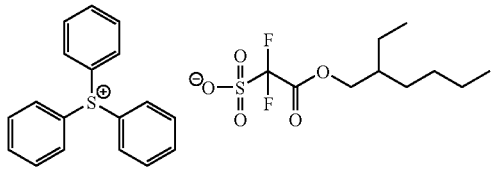
(Y-37) 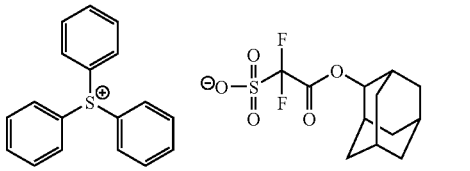
(Y-38) 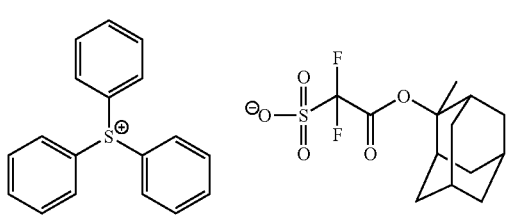
(Y-39) 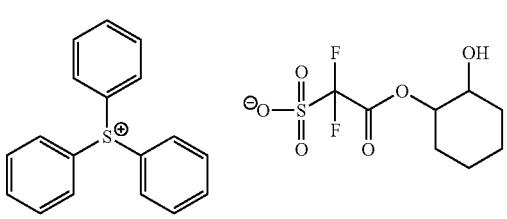
(Y-40) 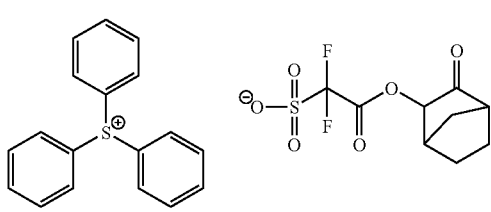
(Y-41) 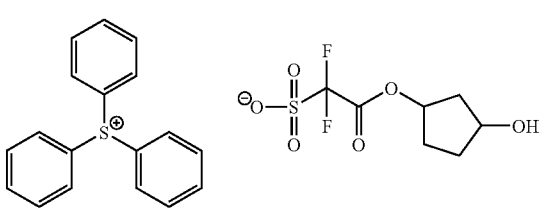
(Y-42) 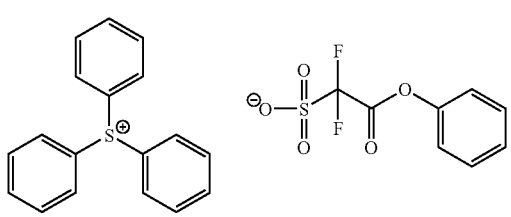
(Y-43) 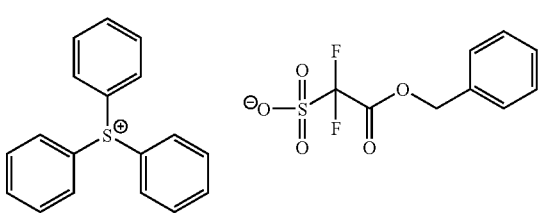

-continued
(Y-44) 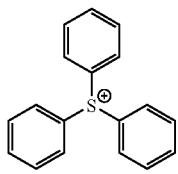 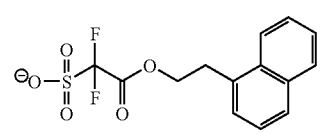
(Y-45) 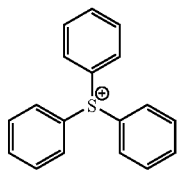 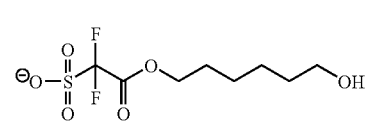
(Y-46) 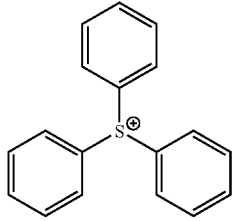 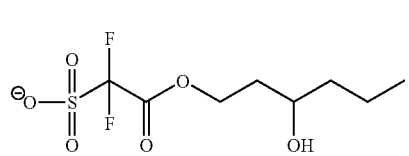
(Y-47) 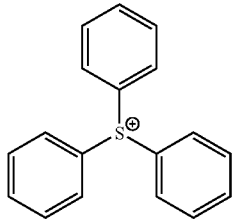 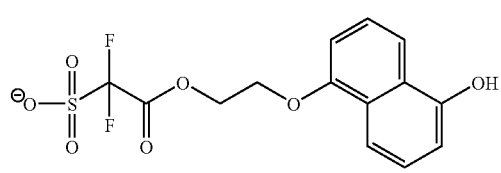
(Y-48) 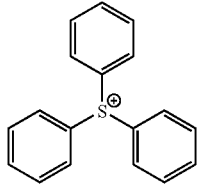 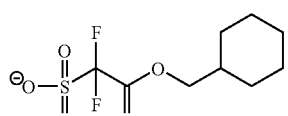
(Y-49) 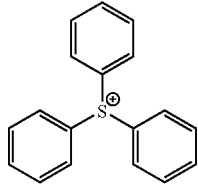 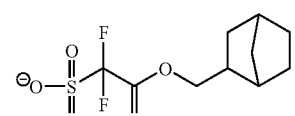
(Y-50) 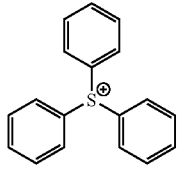 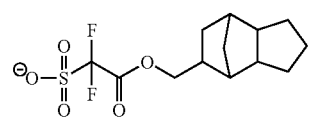
(Y-51) 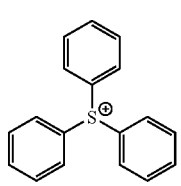 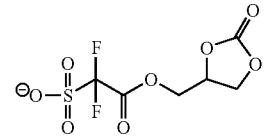
(Y-52) 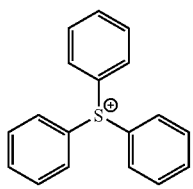 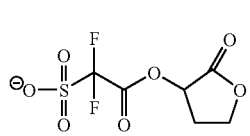
(Y-53) 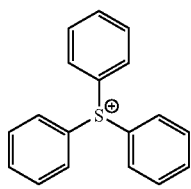 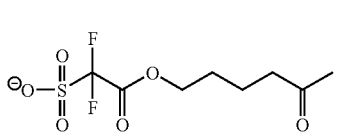
(Y-54) 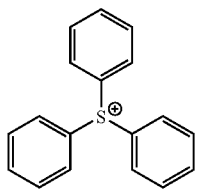 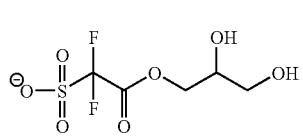
(Y-55) 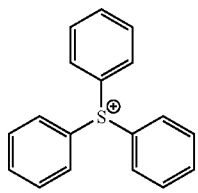 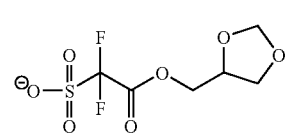

-continued
(Y-56) 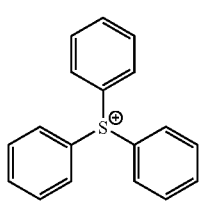 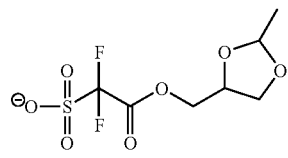
(Y-57) 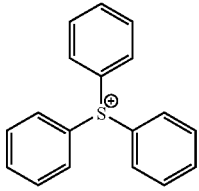 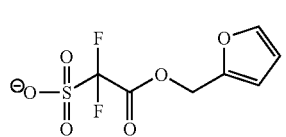
(Y-58) 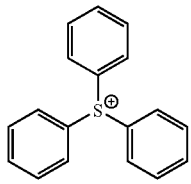 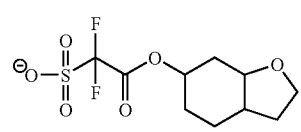
(Y-59) 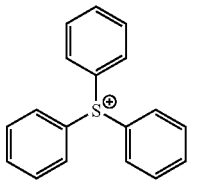 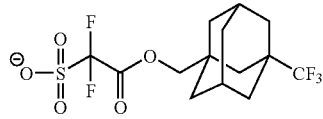
(Y-60) 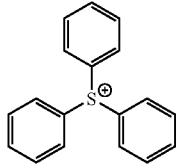 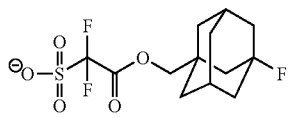
(Y-61) 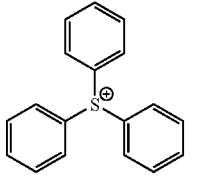 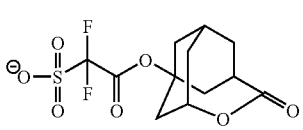
(Y-62) 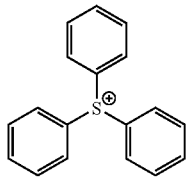 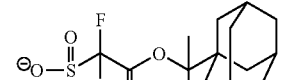
(Y-63) 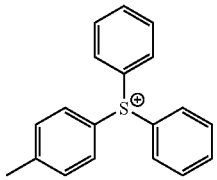 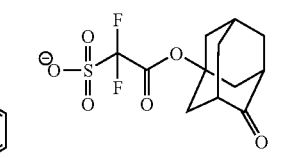
(Y-64) 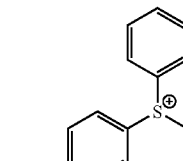 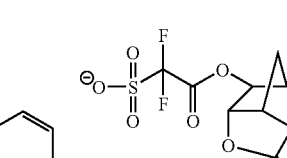
(Y-65) 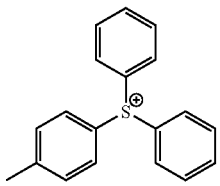 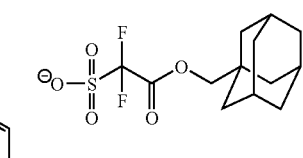
 
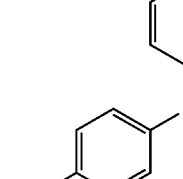 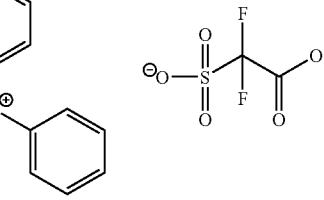 (Y-66)
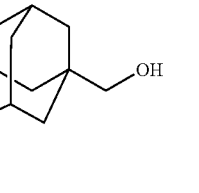  (Y-67)

-continued
(Y-68)
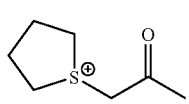 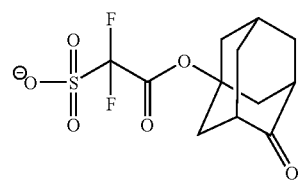
(Y-69)
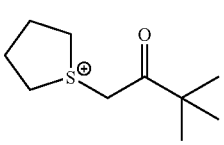 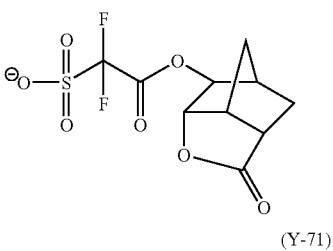
(Y-70)
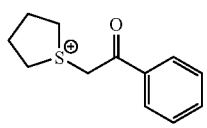 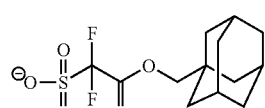
(Y-71)
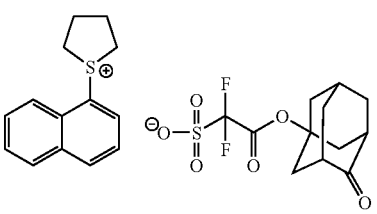
(Y-72)
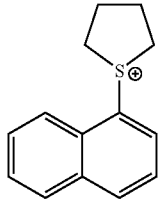 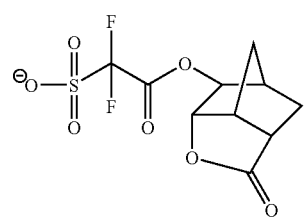
(Y-73)
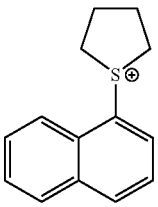
(Y-74)
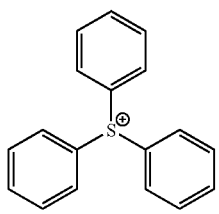 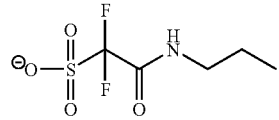
(Y-75)
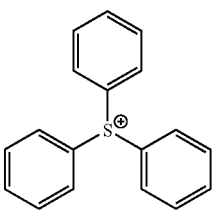 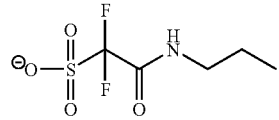
(Y-76)
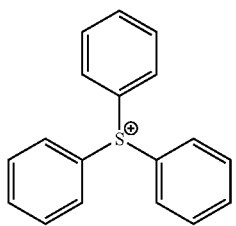 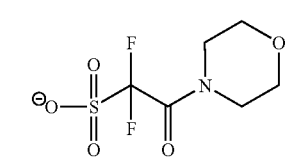
(Y-77)
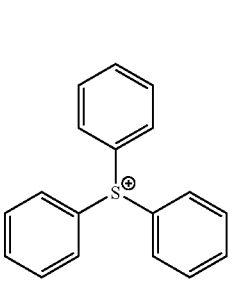 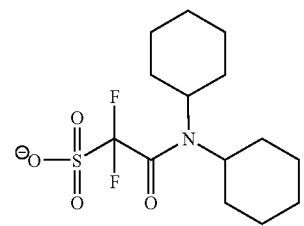
(Y-78)
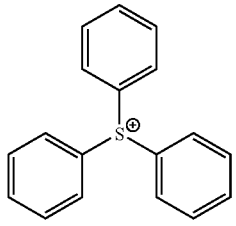 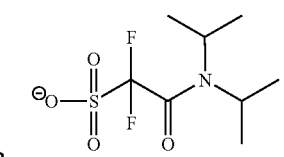
(Y-79)
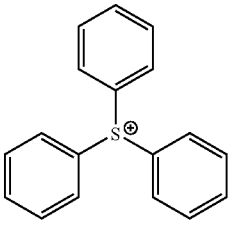 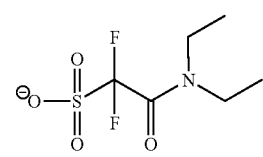

(B) resin whose solubility in an alkali developer is increased by the action of an acid The resin (B) is a resin whose solubility in an alkali developer is increased by the action of an acid;

in particular, a resin having, in its principal chain or side chain, or both of its principal chain and side chain, a group (hereinafter also referred to as "an acid-decomposable group") that is decomposed by the action of an acid to thereby generate an alkali soluble group.

As the alkali soluble group, there can be mentioned a phenolic hydroxyl group, a carboxyl group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a carboxyl group, a fluoroalcohol group (preferably hexafluoroisopropanol) and a sulfonate group.

The acid-decomposable group is preferably a group as obtained by substituting the hydrogen atom of any of these alkali soluble groups with an acid eliminable group.

As the acid eliminable group, there can be mentioned, for example, —C($R_{36}$)($R_{37}$)($R_{38}$), —C($R_{36}$) ($R_{37}$) (O$R_{39}$), —C($R_{01}$) ($R_{02}$) (O$R_{39}$) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ to $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

It is preferred for the resin (B) to contain a repeating unit with an acid-decomposable group. The repeating unit with an acid-decomposable group is preferably any of those of the following general formula (AI).

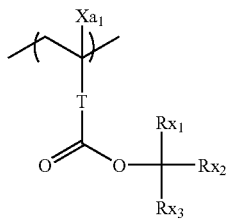

(AI)

In the general formula (AI),

Xa1 represents a hydrogen atom, a methyl group, a trifluoromethyl group or a hydroxymethyl group.

T represents a single bond or a bivalent connecting group.

Each of Rx1 to Rx3 independently represents an alkyl group (linear or branched) or a cycloalkyl group (monocyclic or polycyclic).

At least two of Rx1 to Rx3 may be bonded with each other to thereby form a cycloalkyl group (monocyclic or polycyclic).

As the bivalent connecting group represented by T, there can be mentioned an alkylene group, a group of the formula —COO-Rt-, a group of the formula —O-Rt- or the like. In the formulae, Rt represents an alkylene group or a cycloalkylene group.

T is preferably a single bond or a group of the formula —COO-Rt-. Rt is preferably an alkylene group having 1 to 5 carbon atoms, more preferably a —CH2— group or —(CH2)3- group.

The alkyl group represented by each of Rx1 to Rx3 is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of Rx1 to Rx3 is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

The cycloalkyl group formed by bonding of at least two of Rx1 to Rx3 is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

In a preferred mode, Rx1 is a methyl group or an ethyl group, and Rx2 and Rx3 are bonded with each other to thereby form any of the above-mentioned cycloalkyl groups.

The content of the repeating unit with acid-decomposable groups is preferably in the range of 20 to 50 mol %, more preferably 25 to 45 mol %, based on all the repeating units of the resin (B).

Specific examples of the preferred repeating units with acid-decomposable groups will be shown below, which however in no way limit the scope of the present invention.

In the following formulae, each of Rx and Xa1 represents a hydrogen atom, $CH_3$, $CF_3$ or $CH_2OH$. Each of Rxa and Rxb represents an alkyl group having 1 to 4 carbon atoms.

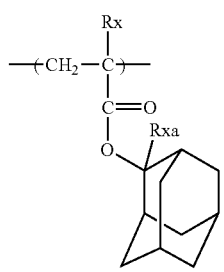

1

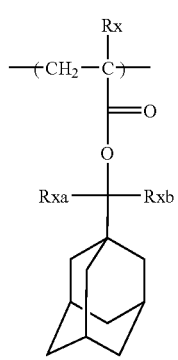

2

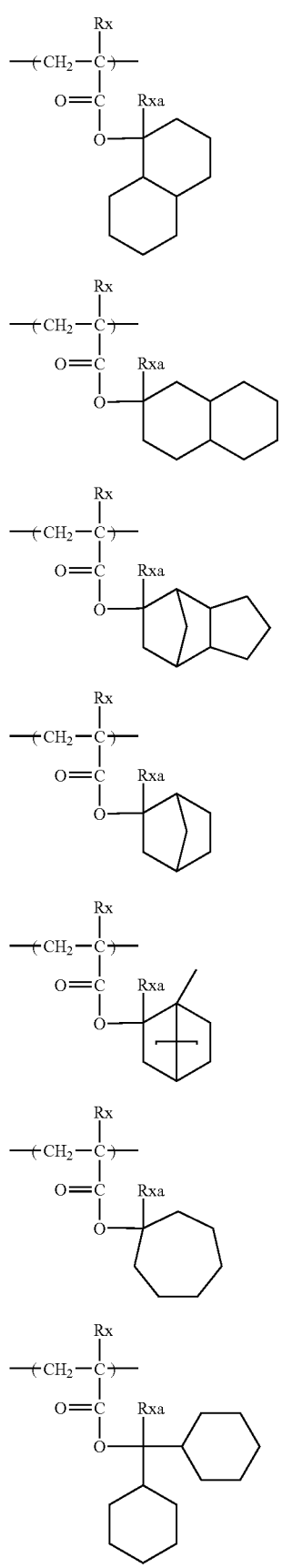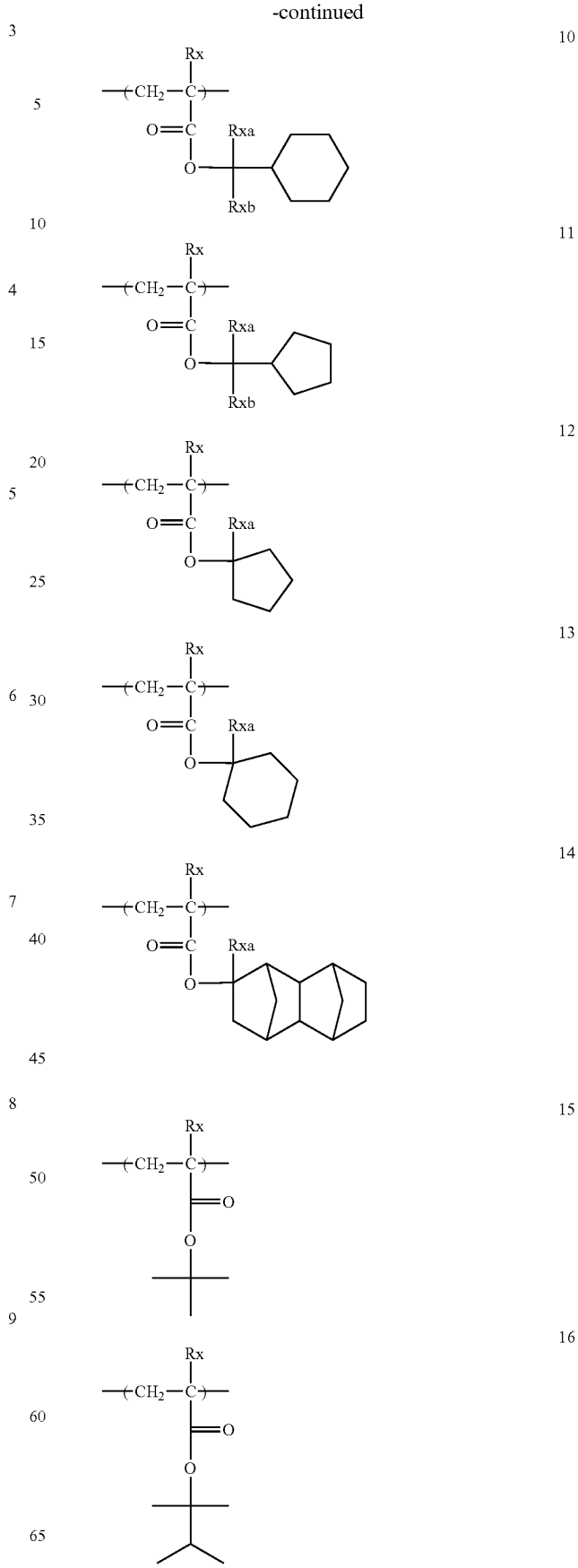

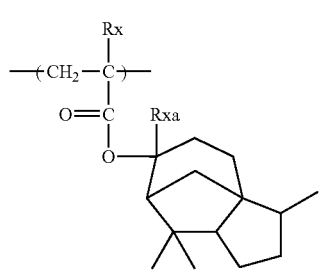
17
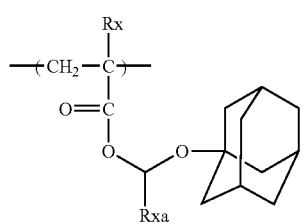
18
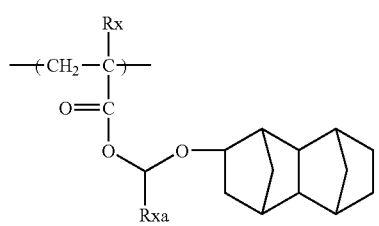
19
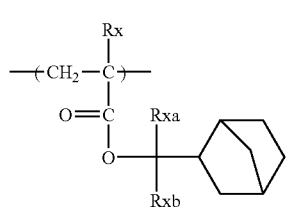
20
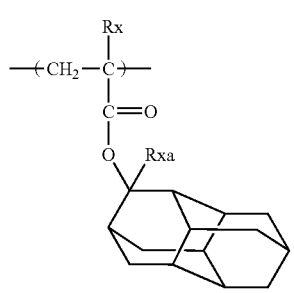
21
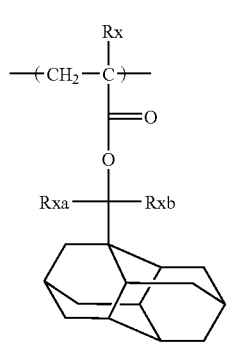
22
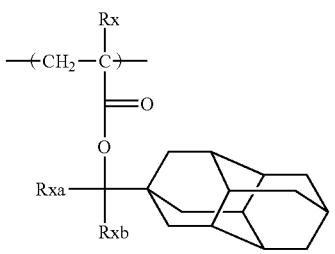
23
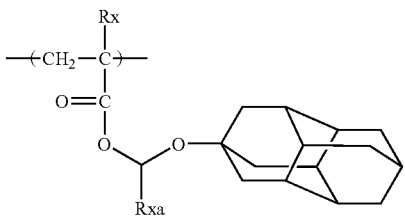
24
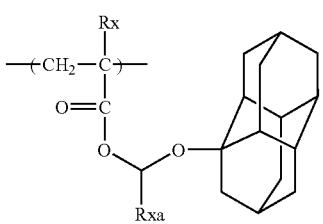
25
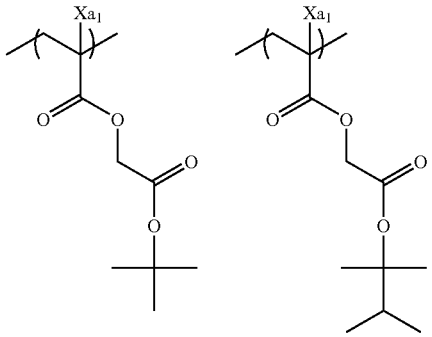
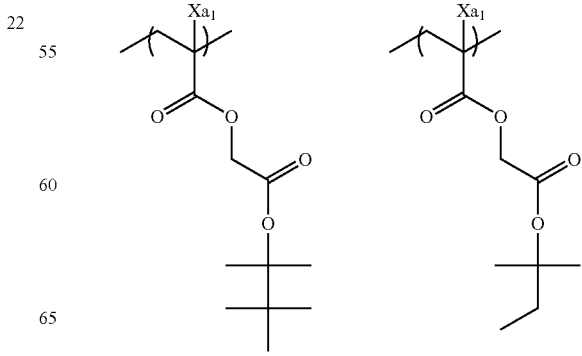

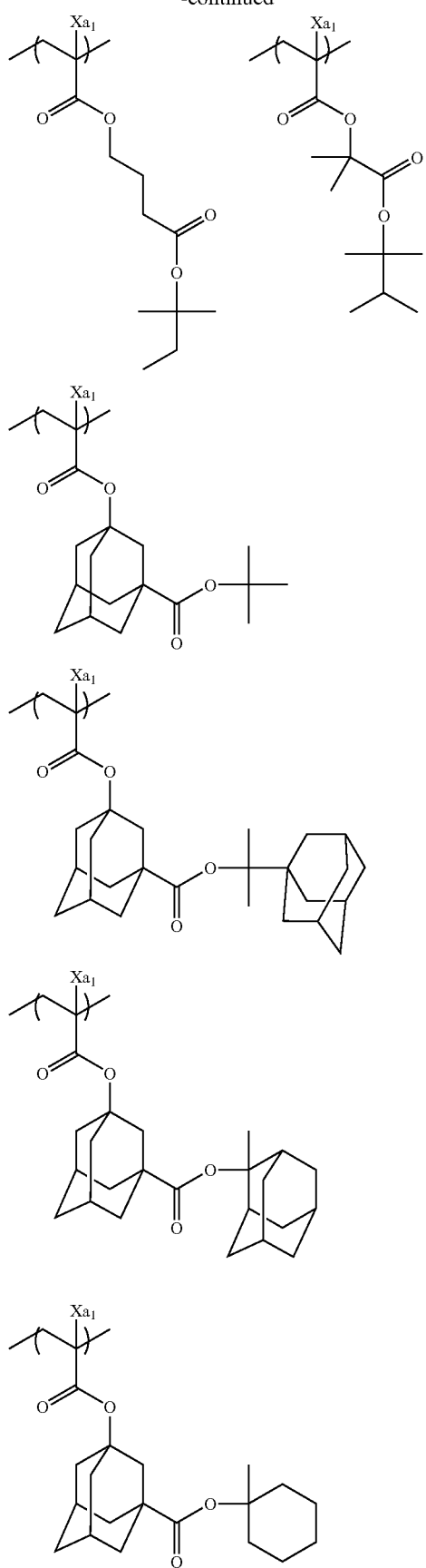
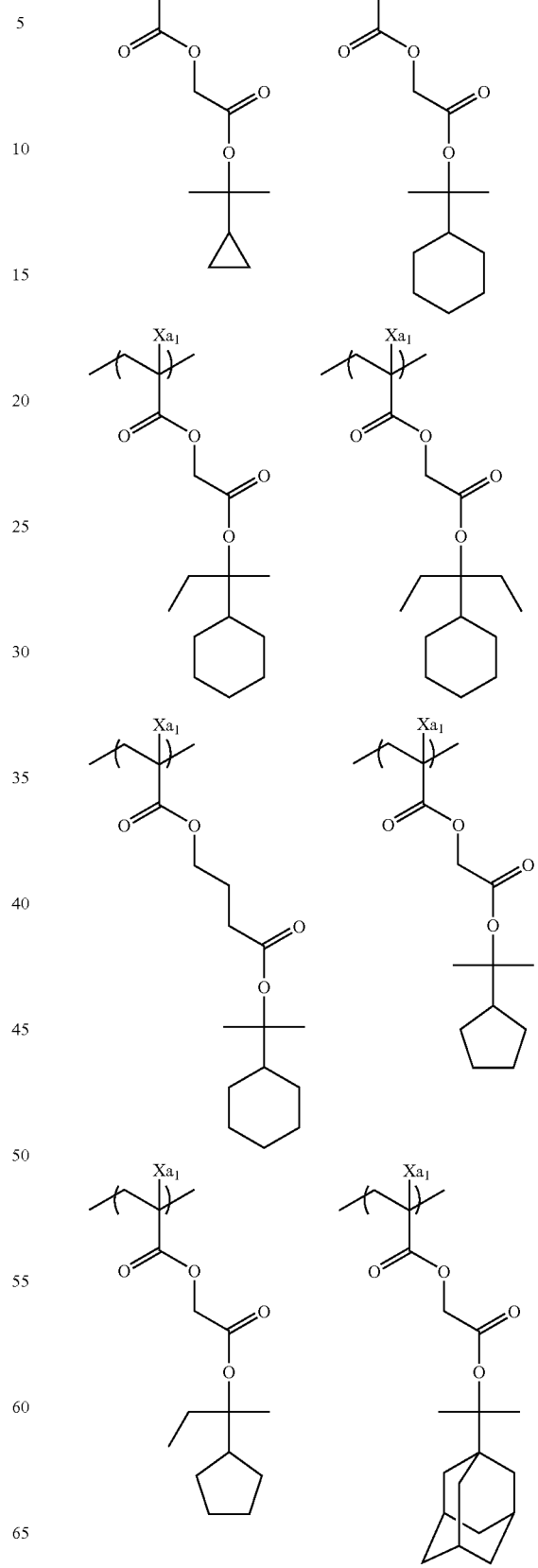

81
-continued
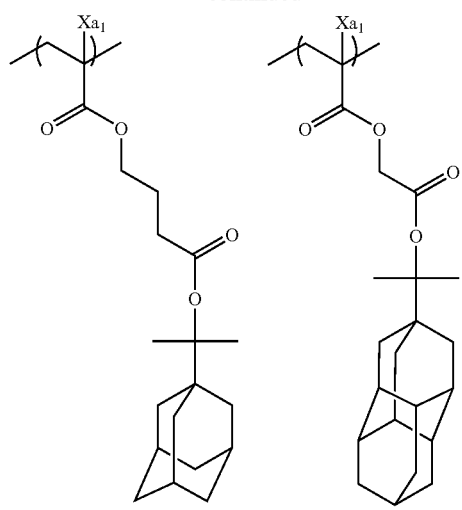
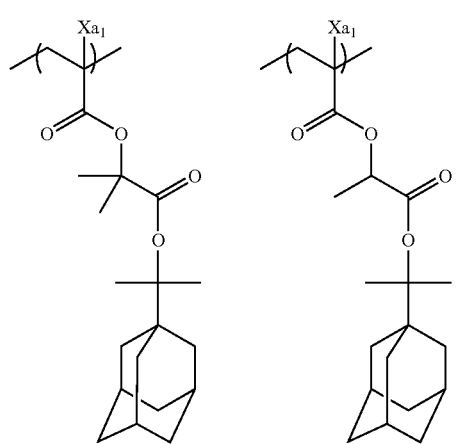
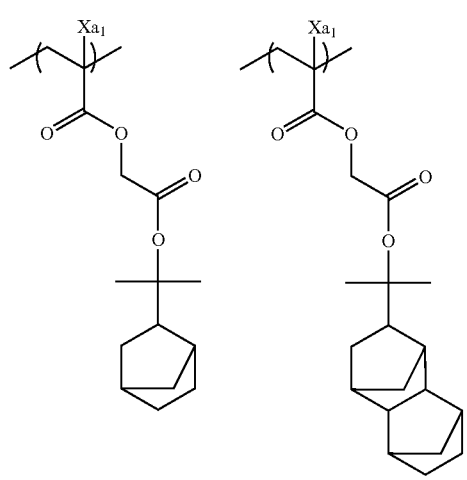
82
-continued
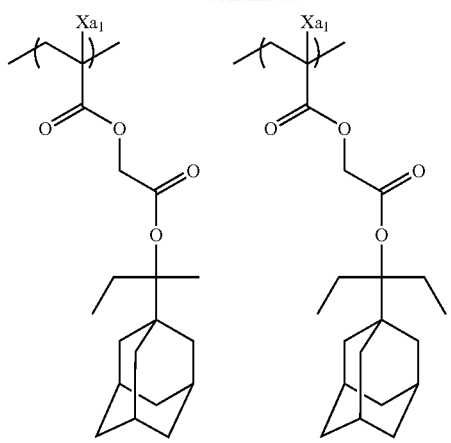
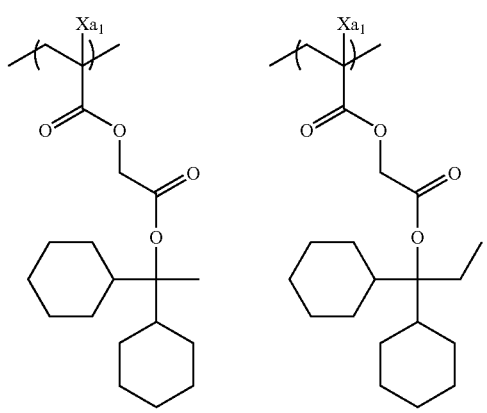
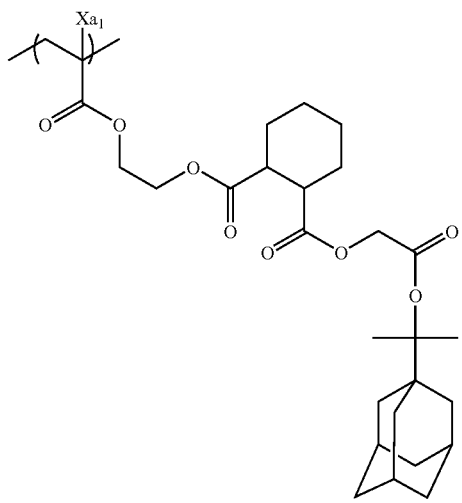

-continued

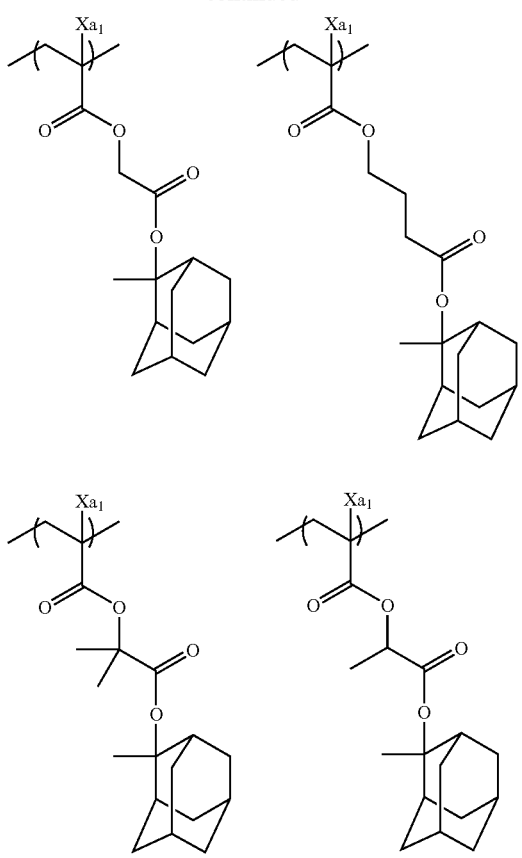
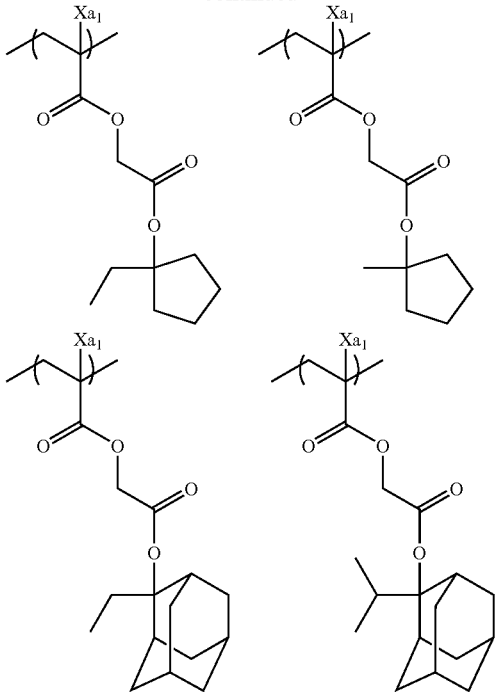

It is more preferred for the resin (B) to contain at least either a repeating unit represented by the following general formula (I) or a repeating unit represented by the following general formula (II) each as the repeating unit represented by the general formula (AI).

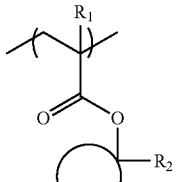

(I)

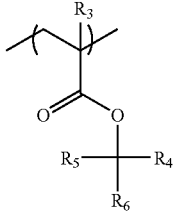

(II)

In the general formulae (I) and (II), each of $R_1$ and $R_3$ independently represents a hydrogen atom, an optionally substituted methyl group or a group represented by —$CH_2$—$R_9$. $R_9$ represents a monovalent organic group.

Each of $R_2$, $R_4$, $R_5$, and $R_6$ independently represents an alkyl group or a cycloalkyl group.

R represents an atomic group for forming an alicyclic structure in cooperation with the carbon atom of the general formula (I).

$R_1$ preferably represents a hydrogen atom, a methyl group, a trifluoromethyl group or a hydroxymethyl group.

The alkyl group represented by $R_2$ includes a linear or branched structure and may have a substituent.

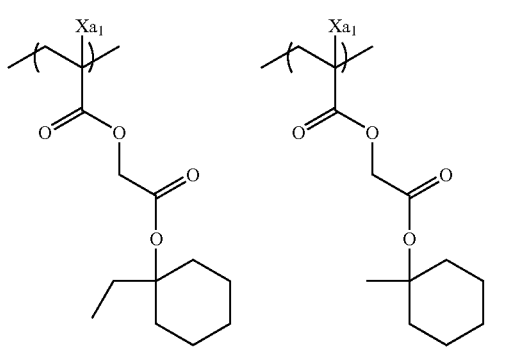

The cycloalkyl group represented by $R_2$ includes a monocyclic or polycyclic structure and may have a substituent.

$R_2$ is preferably an alkyl group, more preferably an alkyl group having 1 to 10 carbon atoms and most preferably an alkyl group having 1 to 5 carbon atoms, for example, a methyl group, an ethyl group or the like.

R represents an atomic group for forming an alicyclic structure in cooperation with the carbon atom of the general formula (I). The alicyclic structure formed by R is preferably a monocyclic structure and the number of carbon atoms thereof is preferably 3 to 7, more preferably 5 or 6.

$R_3$ is preferably a hydrogen atom or a methyl group, more preferably a methyl group.

The alkyl group represented by each of $R_4$, $R_5$ and $R_6$ includes a linear or branched structure and may have a substituent. The alkyl group is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $R_4$, $R_5$ and $R_6$ includes a monocyclic or polycyclic structure and may have a substituent. The cycloalkyl group is preferably a monocyclic structure, such as a cyclopentyl group or a cyclohexyl group, or a polycycic structure, such as a norbornyl group, a tetracyclodecanyl group, a tetracyclododecanyl group or an adamantyl group.

As the repeating unit represented by the general formula (I), there can be mentioned a repeating unit represented by the general formula (1-a) below.

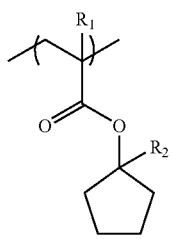

(1-a)

In the general formula (1-a), $R_1$ and $R_2$ are as defined above with respect to the general formula (I).

The repeating unit represented by the general formula (II) is preferably the repeating unit represented by the general formula (II-1) below.

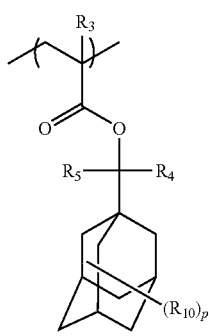

(II-1)

In the general formula (II-1), $R_3$, $R_4$ and $R_5$ are as defined above with respect to the general formula (II).

$R_{10}$, each independently in the presence of two or more groups, represents a substituent containing a polar group. As the substituent containing a polar group, there can be mentioned a linear or branched alkyl group or a cycloalkyl group each containing a hydroxyl group, a cyano group, an amino group, an alkylamido group or a sulfonamido group. An alkyl group containing a hydroxyl group is especially preferred. As a branched alkyl group, an isopropyl group is especially preferred.

p is an integer of 0 to 15. p is preferably 0 to 2, more preferably 0 or 1.

As mentioned above, It is more preferred for the acid-decomposable resin (B) to contain at least either a repeating unit represented by the general formula (I) or a repeating unit represented by the general formula (II) each as a repeating unit represented by the general formula (AI). In another mode, it is more preferred for resin (B) to contain two or more types of repeating units represented by the general formula (I) as repeating units represented by the general formula (AI).

When the resin (B) contains two types of the repeating units of the general formula (AI), for example, the following examples are preferred.

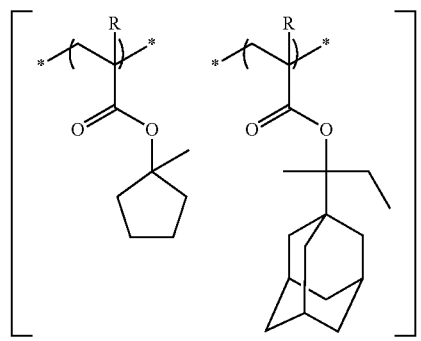

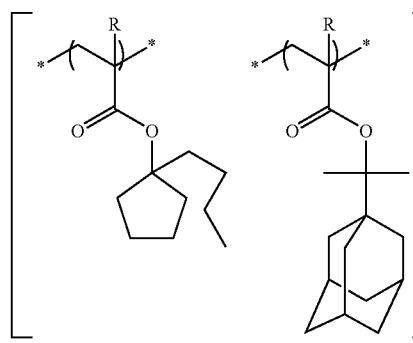

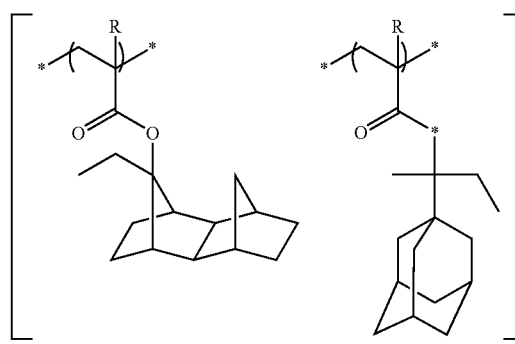

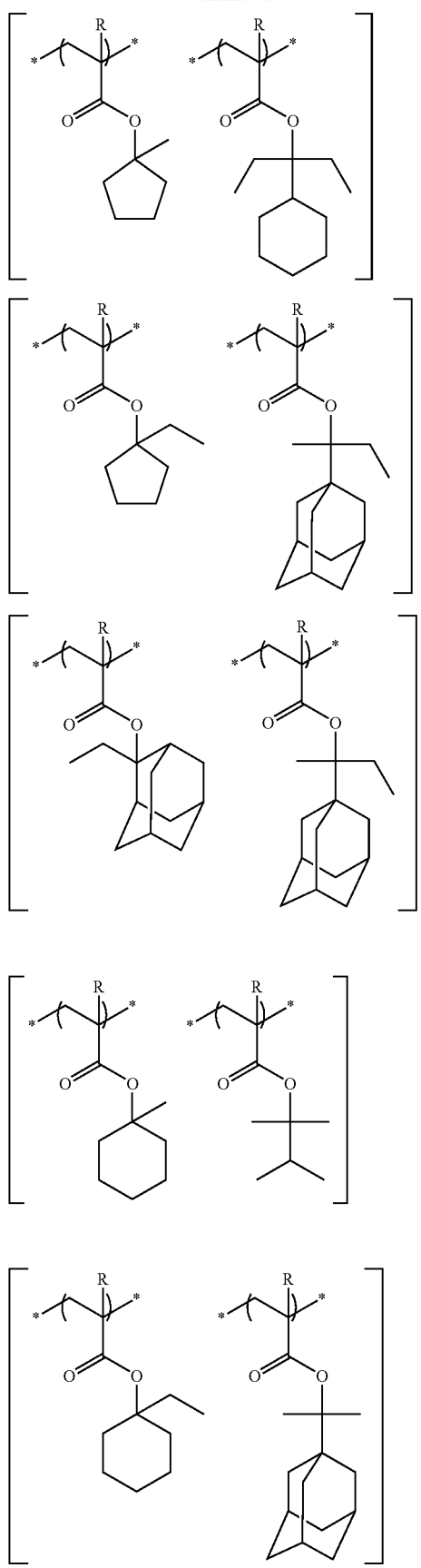
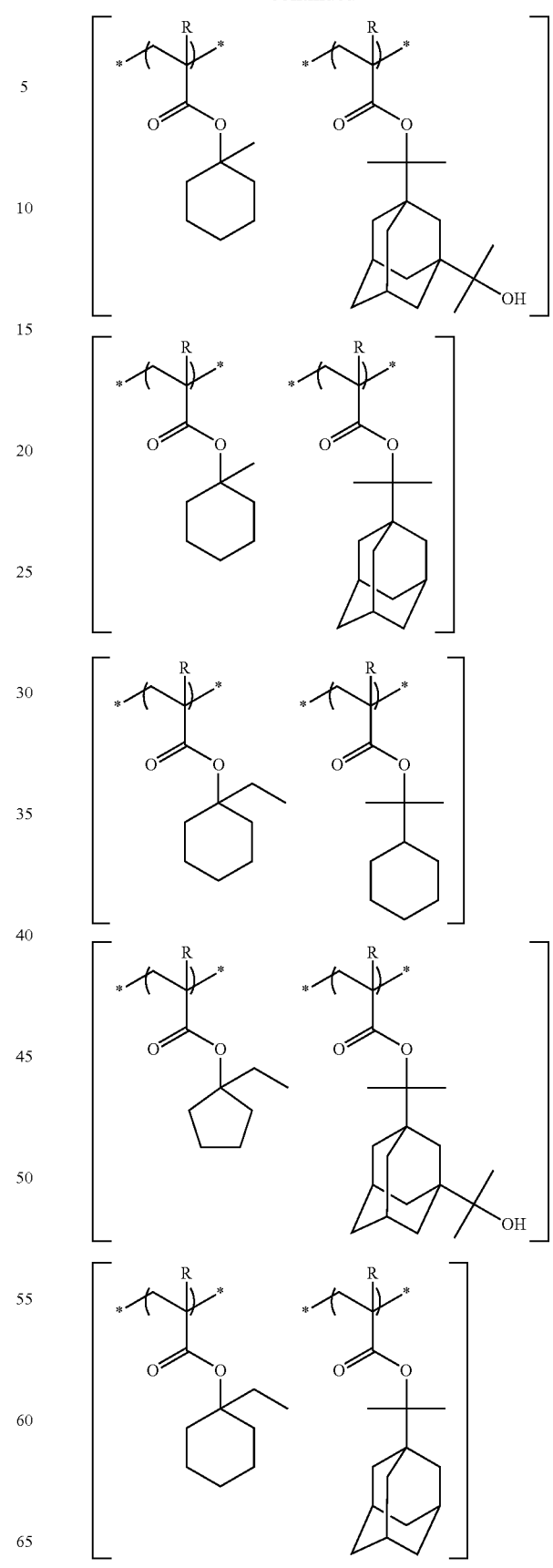

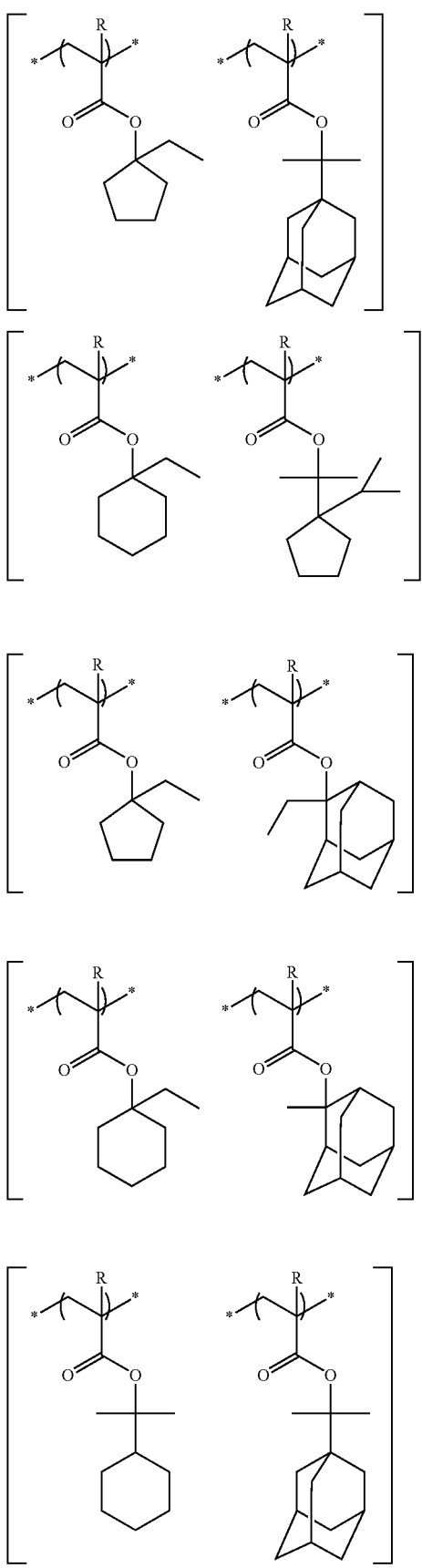
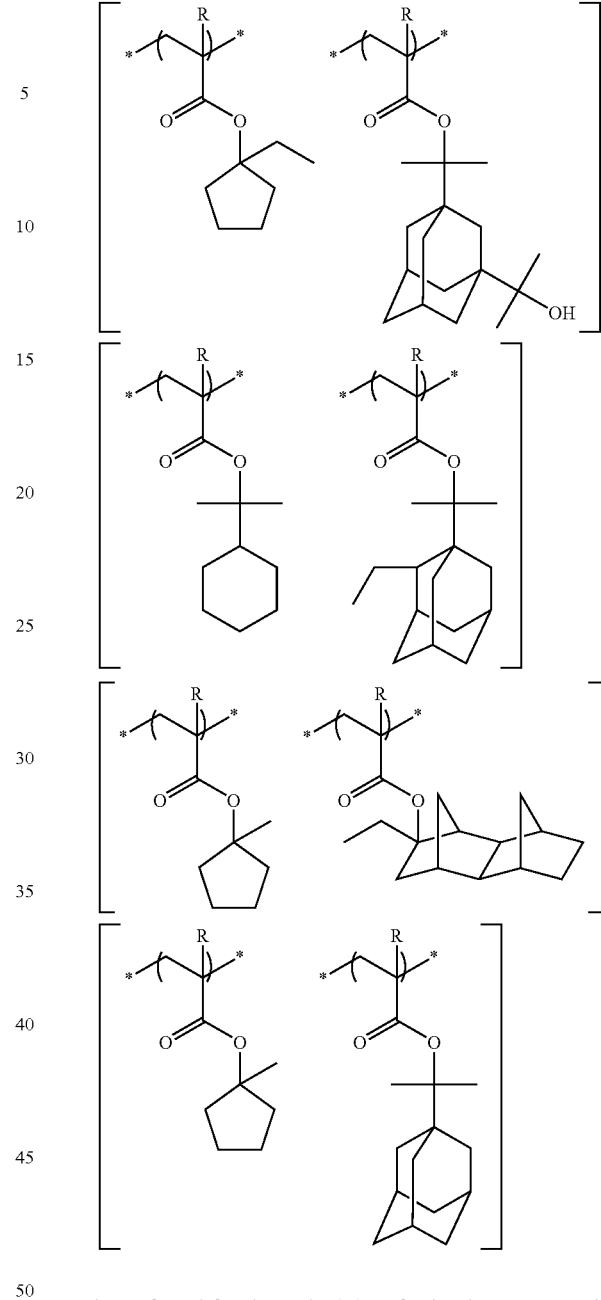

It is preferred for the resin (B) to further have a repeating unit having at least one group selected from among a lactone group, a hydroxyl group, a cyano group and an alkali soluble group.

The repeating unit having a lactone group that may be contained in the resin (B) will now be described.

Any lactone groups can be employed as long as a lactone structure is possessed therein. However, lactone structures of a 5 to 7-membered ring are preferred, and in particular, those resulting from condensation of lactone structures of a 5 to 7-membered ring with other cyclic structures effected in a fashion to form a bicyclo structure or spiro structure are preferred. The possession of repeating units having a lactone structure represented by any of the following general formulae (LC1-1) to (LC1-16) is more preferred. The lactone structures may be directly bonded to the principal chain of the resin. Preferred lactone structures are those of the formulae (LC1-1), (LC1-4), (LC1-5), (LC1-6), (LC1-13) and (LC1-14). The use of these specified lactone structures would ensure improvement in the line edge roughness and development defect.
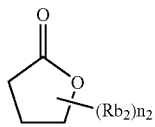
LC1-1
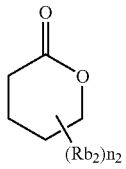
LC1-2
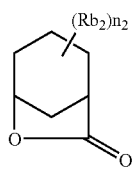
LC1-3
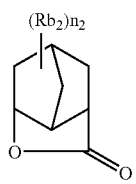
LC1-4
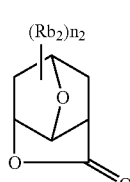
LC1-5
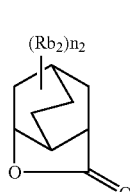
LC1-6
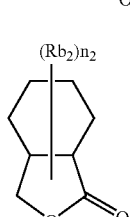
LC1-7
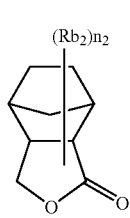
LC1-8
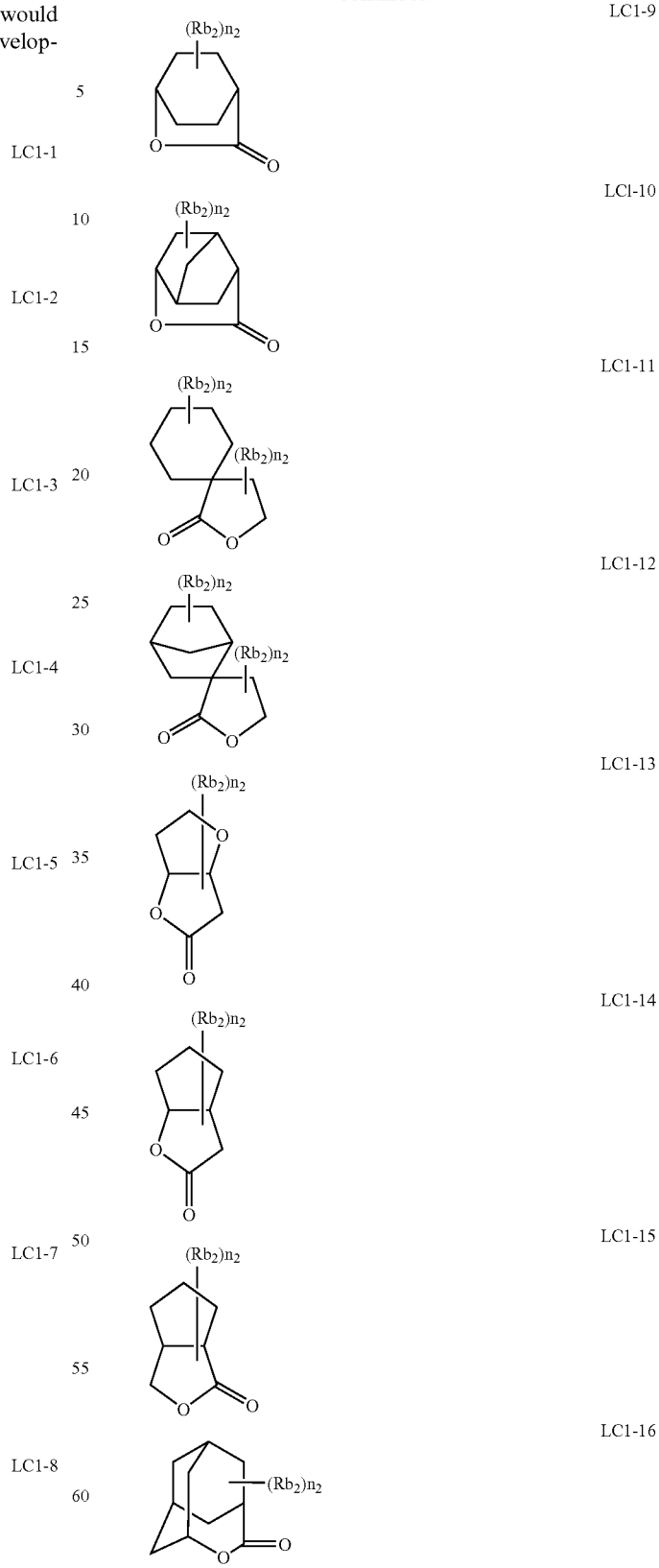
The presence of a substituent ($Rb_2$) on the portion of the lactone structure is optional. As a preferred substituent ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, $n_2$ is an integer of 0 to 4. When $n_2$ is 2 or greater, the plurality of present substituents ($Rb_2$) may be identical to or different from each other. Further, the plurality of present substituents ($Rb_2$) may be bonded with each other to thereby form a ring.

As the repeating units with a lactone structure represented by any of the general formulae (LC1-1) to (LC1-16), there can be mentioned the repeating units represented by the following general formula (AII).

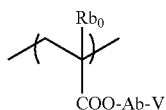

(AII)

In the general formula (AII), $Rb_0$ represents a hydrogen atom, a halogen atom or an optionally substituted alkyl group having 1 to 4 carbon atoms. As a preferred substituent optionally contained in the alkyl group represented by $Rb_0$, there can be mentioned a hydroxyl group or a halogen atom. As the halogen atom represented by $Rb_0$, there can be mentioned a fluorine atom, a chlorine atom, a bromine atom or an iodine atom. The $Rb_0$ is preferably a hydrogen atom, a methyl group, a hydroxymethyl group or a trifluoromethyl group. A hydrogen atom and a methyl group are especially preferred.

Ab represents a single bond, an alkylene group, a bivalent connecting group with an alicyclic hydrocarbon structure of a single ring or multiple rings, an ether group, an ester group, a carbonyl group, or a bivalent connecting group resulting from combination thereof. A single bond and a bivalent connecting group of the formula -$Ab_1$-$CO_2$— are preferred.

$Ab_1$ is a linear or branched alkylene group or a cycloalkylene group of a monocyclic structure or polycyclic structure, being preferably a methylene group, an ethylene group, a cyclohexylene group, an adamantylene group or a norbornylene group, and more preferably a methylene group or an ethylene group.

V represents a group with a structure represented by any of the general formulae (LC1-1) to (LC1-16).

The repeating unit having a lactone group is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity (ee) thereof is preferably 90 or higher, more preferably 95 or higher.

The content of the repeating unit having a lactone group based on all the repeating units of the resin (B) is preferably in the range of 15 to 60 mol %, more preferably 20 to 50 mol % and still more preferably 30 to 50 mol %.

Examples of the repeating units having a lactone group will now be shown, which however in no way limit the scope of the present invention. In the formulae, Rx represents H, CH3, CH2OH or CF3.

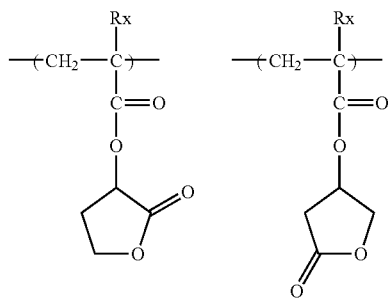

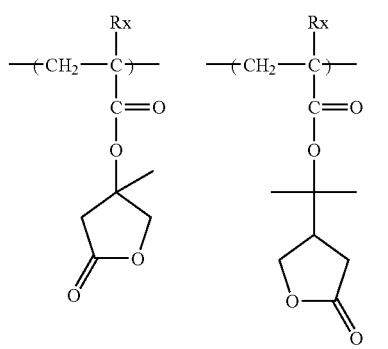

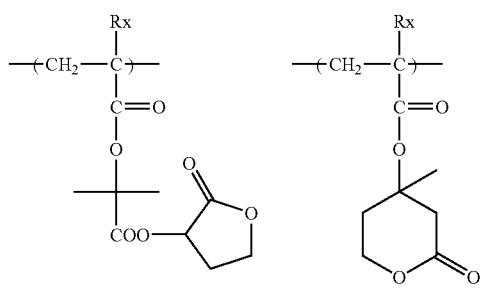

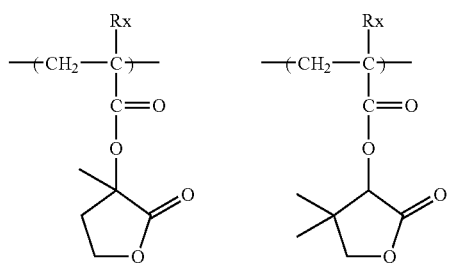

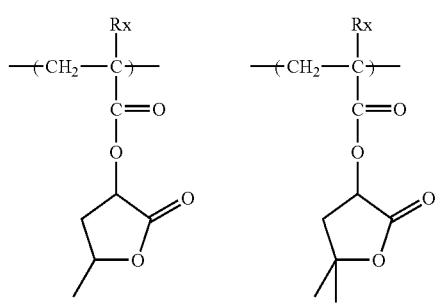

95
-continued
96
-continued
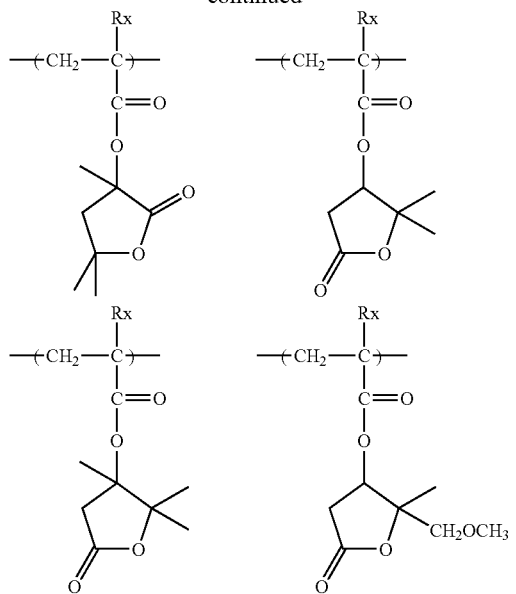
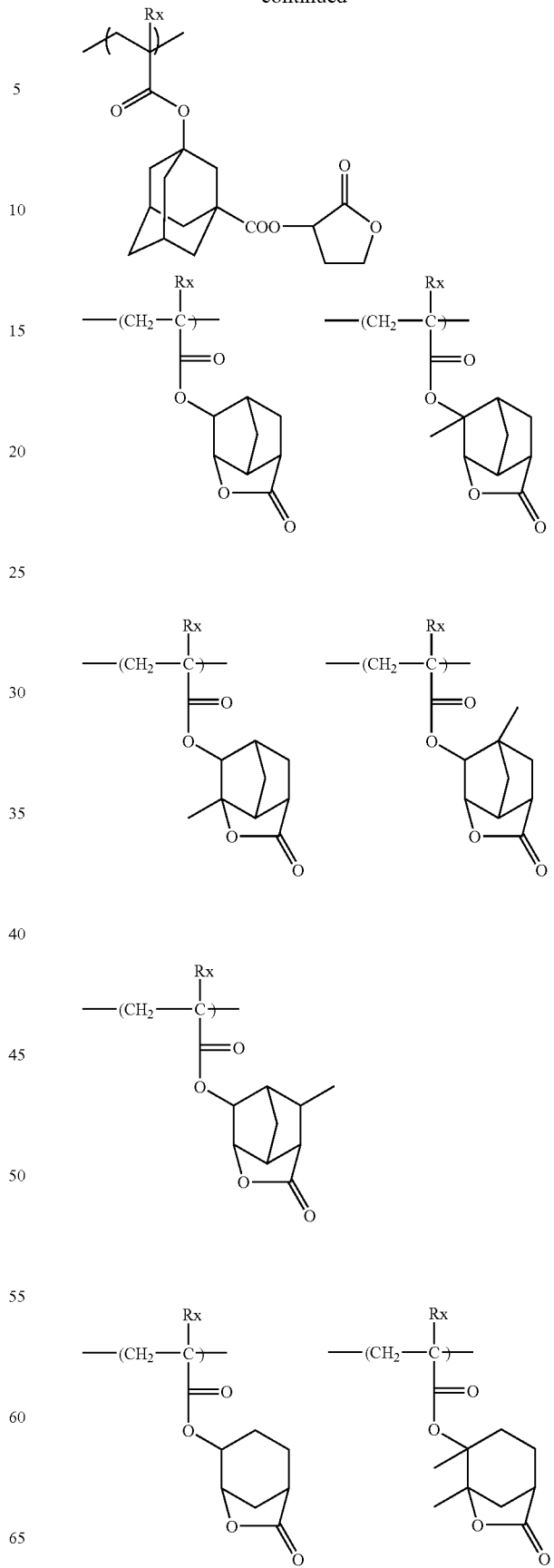

97
-continued
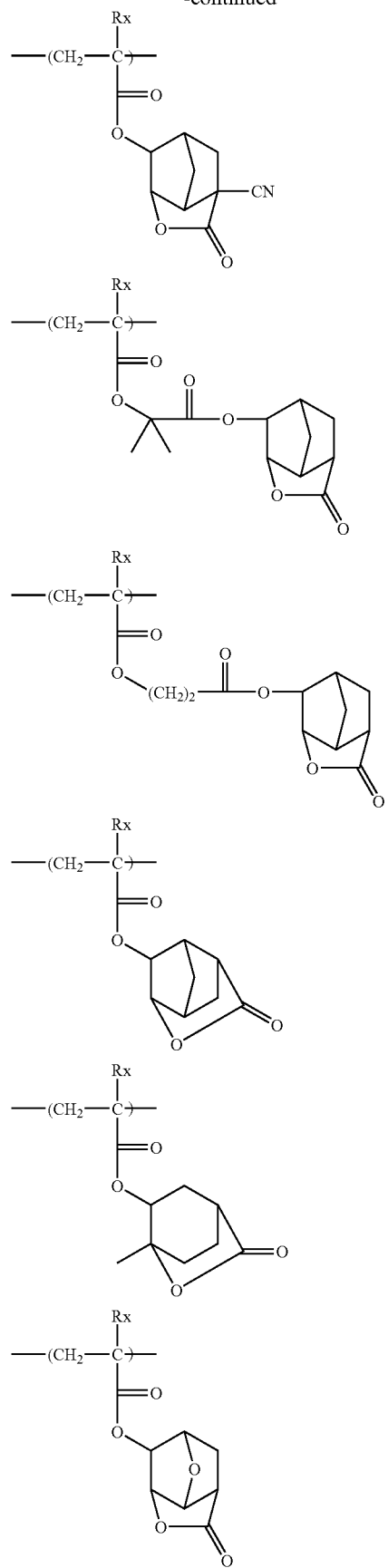
98
-continued
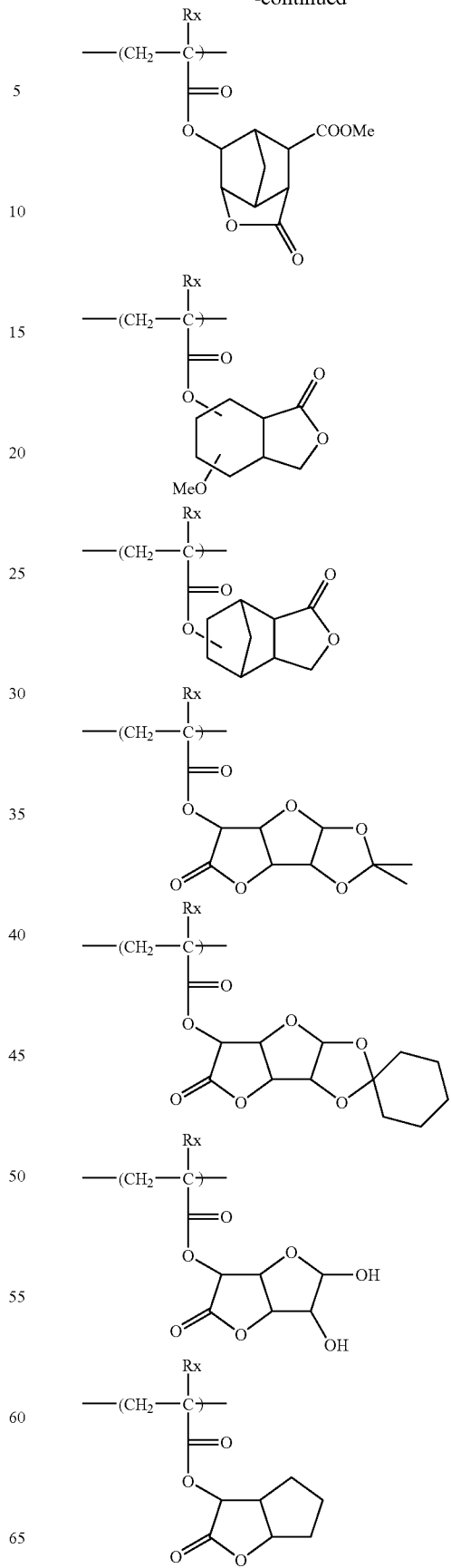

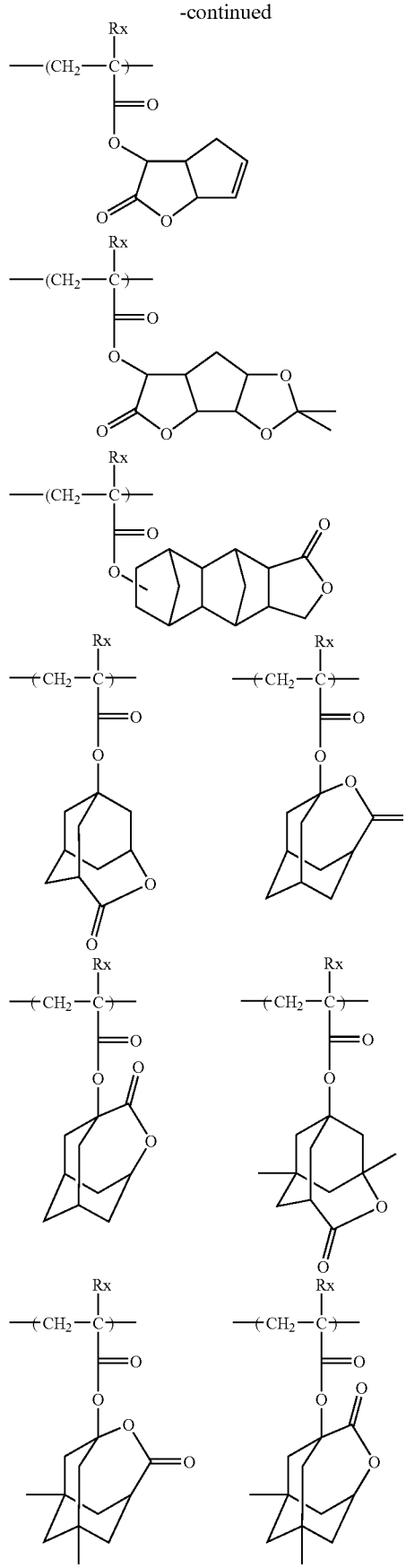
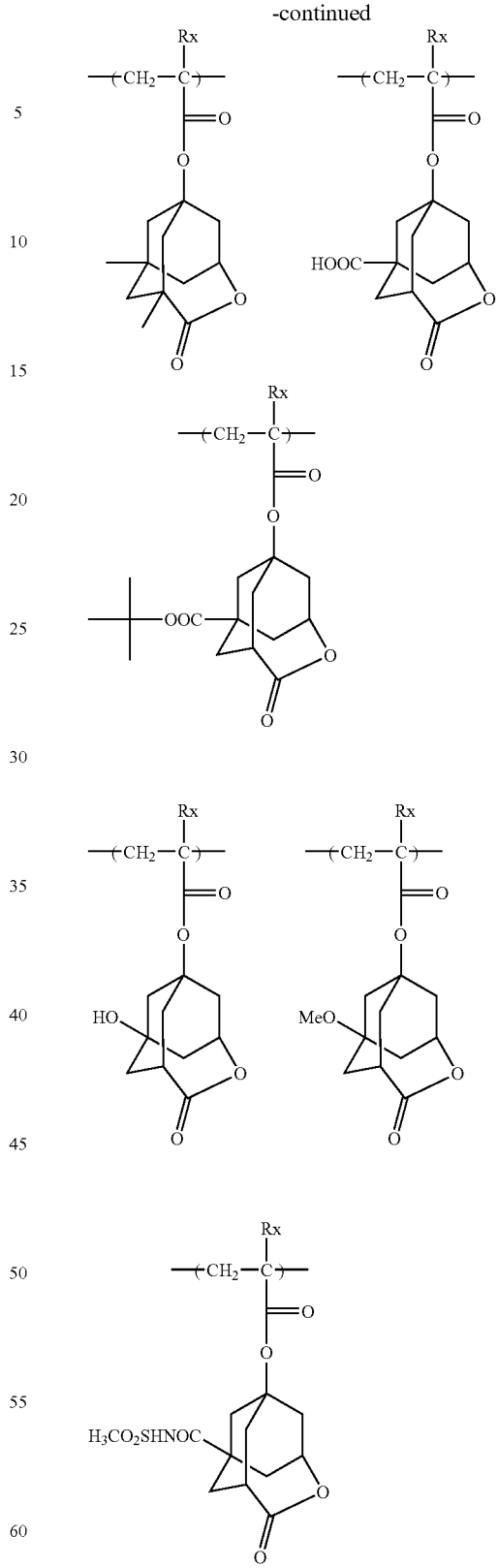
In the following formulae, R represents a hydrogen atom, an optionally substituted alkyl group or a halogen atom. R represents preferably a hydrogen atom, a methyl group, a hydroxymethyl group or an acetyl group.

101
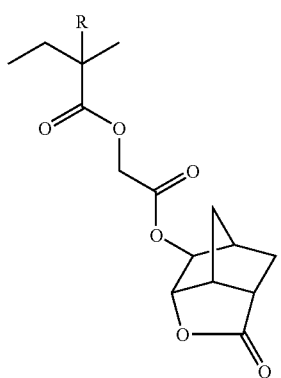
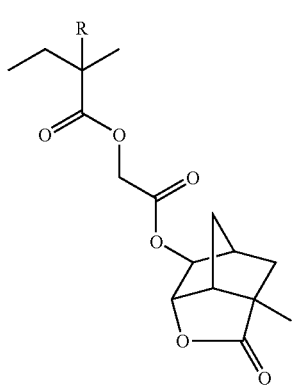
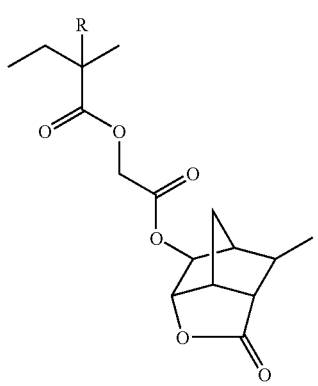
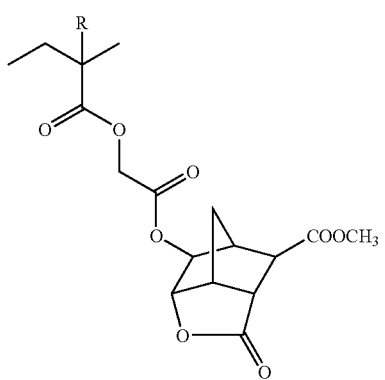
102
-continued
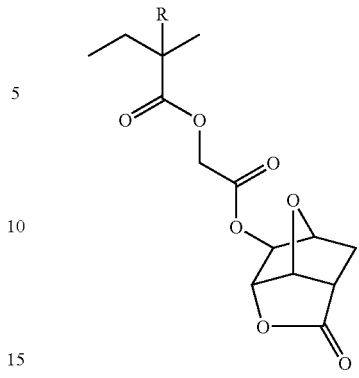
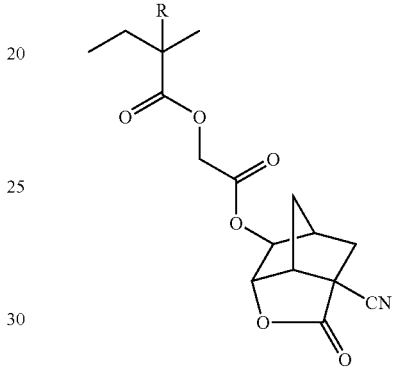
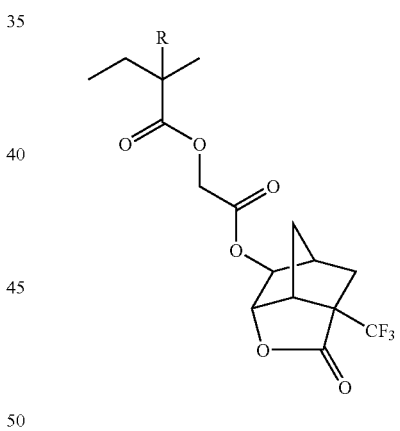
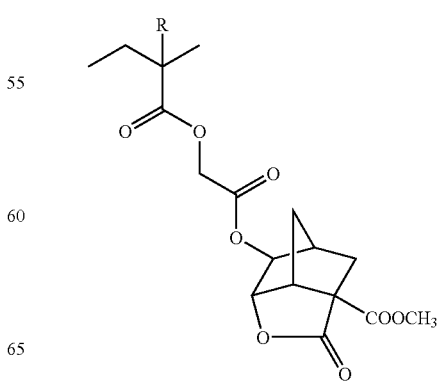

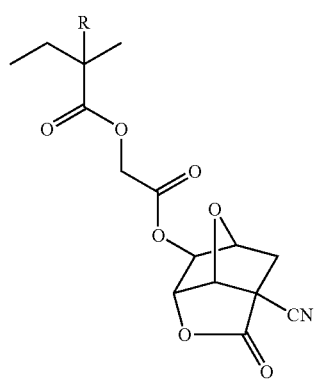
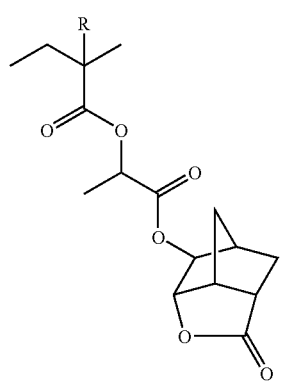
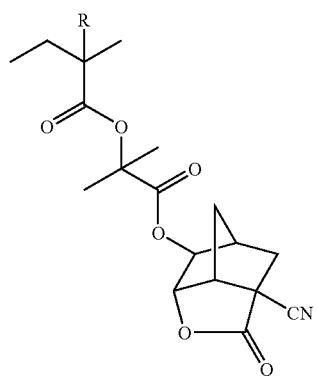
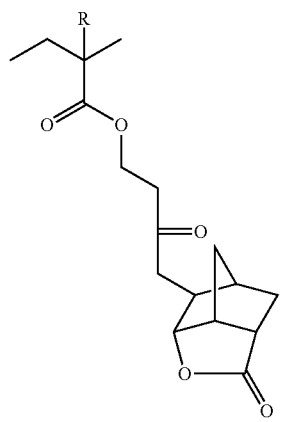
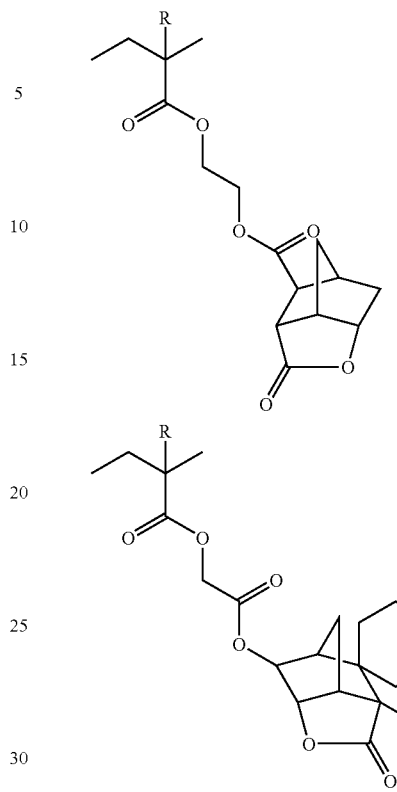
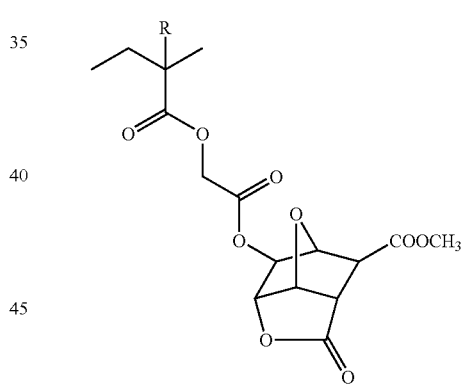
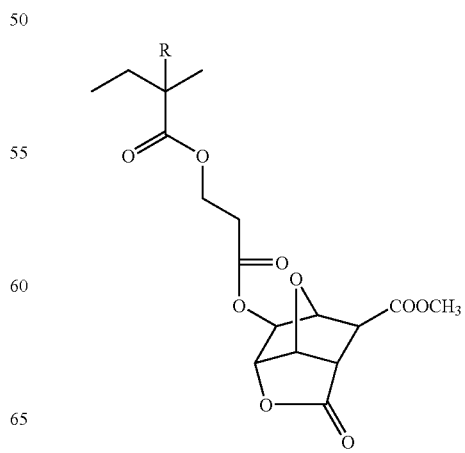

-continued
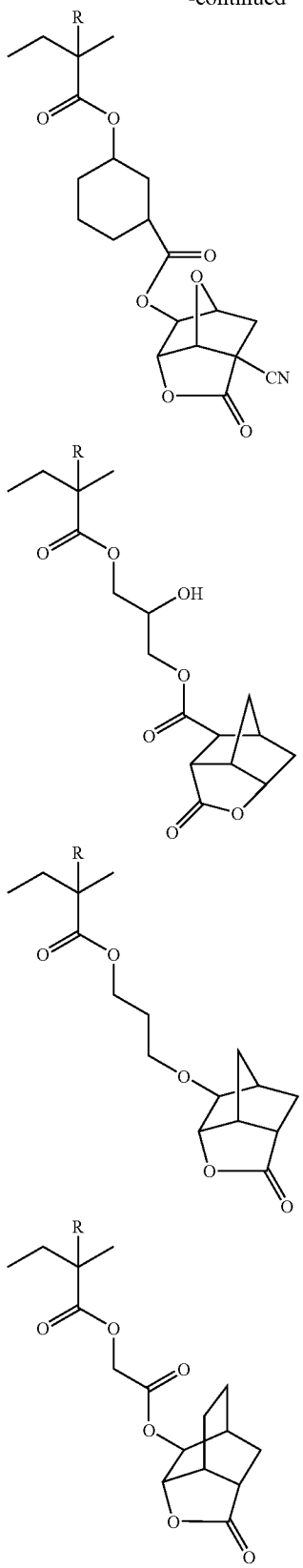
The especially preferred repeating units having a lactone group will be shown below. An improvement in pattern profile and optical density dependence can be attained by selection of the most appropriate lactone group. In the formulae, Rx represents H, $CH_3$, $CH_2OH$ or $CF_3$.
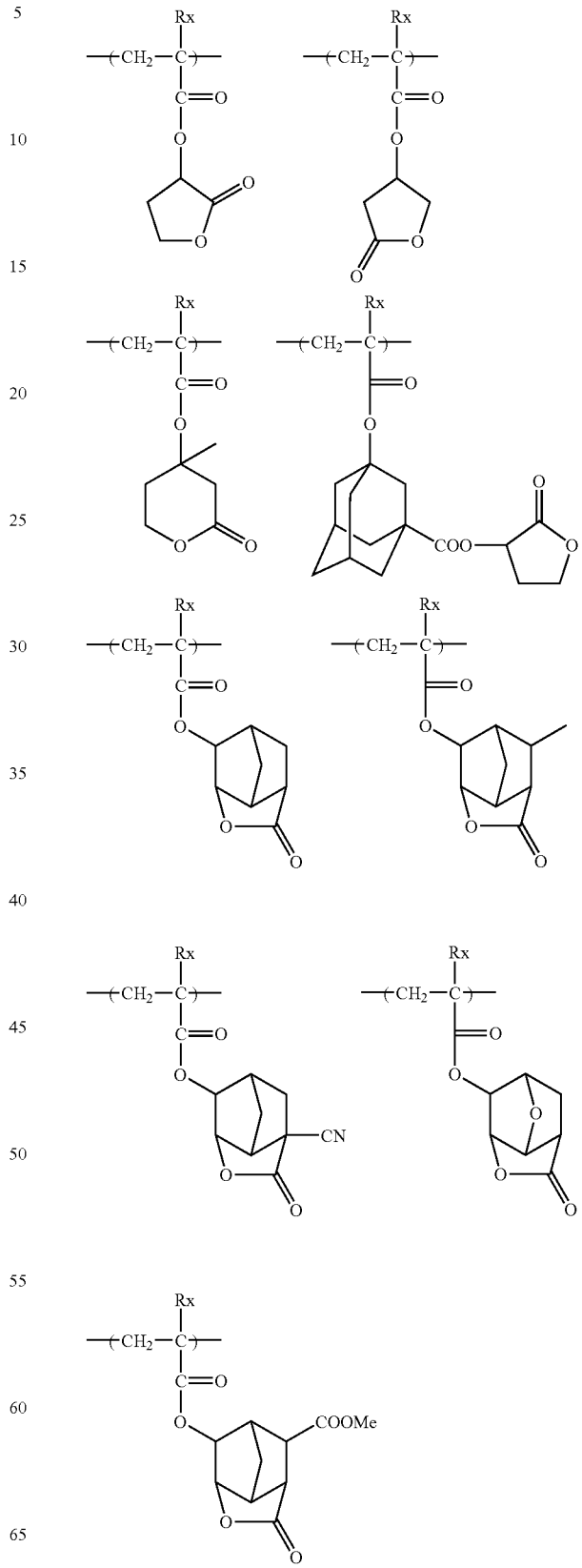

107
-continued
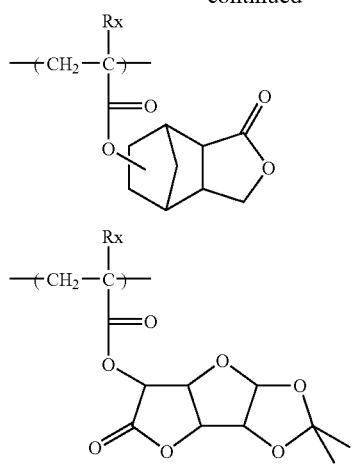
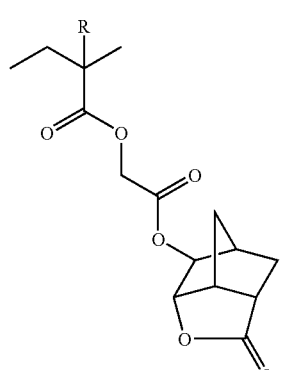
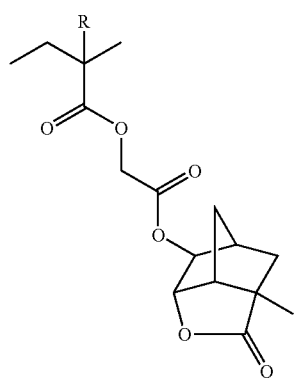
108
-continued
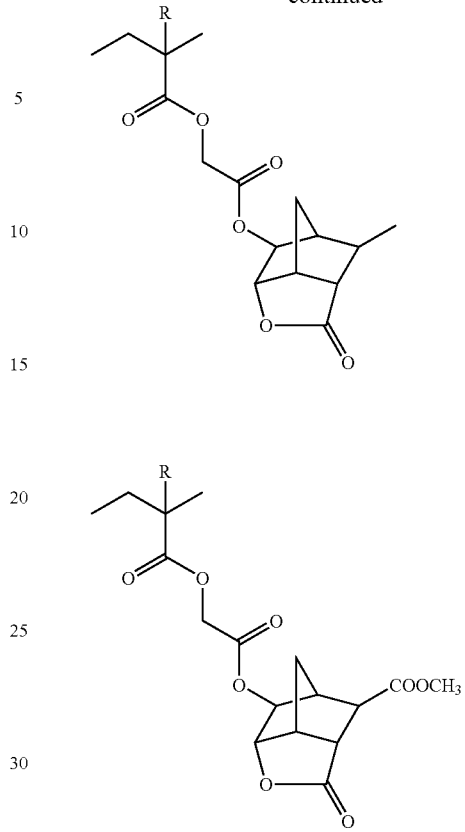
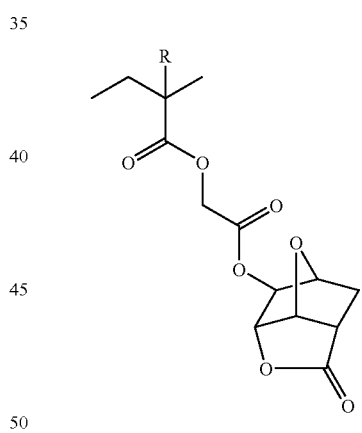
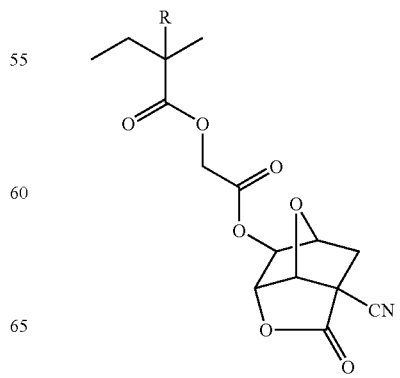

-continued (VIIa shown at top left)

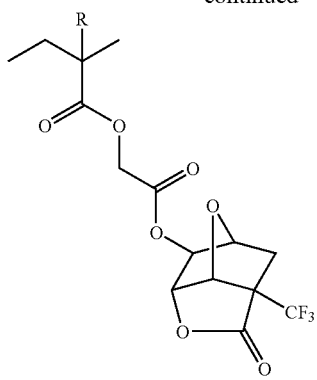

The resin (B) may contain two or more types of repeating units each having a lactone group. In this case, it is preferred to contain at least one of the repeating units of the general formula (AII) above wherein Ab is any of the bivalent connecting groups of the formula -Ab$_1$-CO$_2$—.

It is preferred for the resin (B) to have a repeating unit other than the repeating units of the above general formulae, having a hydroxyl group or a cyano group. The containment of this repeating unit would realize enhancements of adhesion to substrate and developer affinity. The repeating unit having a hydroxyl group or a cyano group is preferably a repeating unit having an alicyclic hydrocarbon structure substituted with a hydroxyl group or a cyano group. In the alicyclic hydrocarbon structure substituted with a hydroxyl group or a cyano group, the alicyclic hydrocarbon structure preferably consists of an adamantyl group, a diamantyl group or a norbornane group. As preferred alicyclic hydrocarbon structures substituted with a hydroxyl group or a cyano group, there can be mentioned the partial structures of the following general formulae (VIIa) to (VIId).

(VIIa)

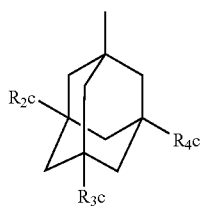

(VIIb)

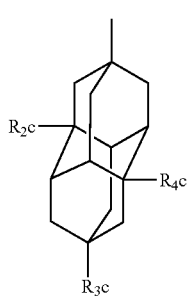

(VIIc)

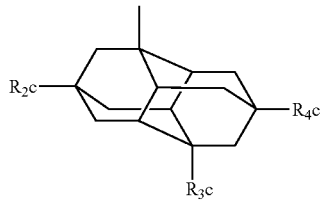

(VIId)

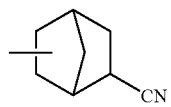

In the general formulae (VIIa) to (VIII), each of R2c to R4c independently represents a hydrogen atom, a hydroxyl group or a cyano group, providing that at least one of the R2c to R4c represents a hydroxyl group or a cyano group.

Preferably, one or two of the R2c to R4c are hydroxyl groups and the remainder is a hydrogen atom. In the general formula (VIIa), more preferably, two of the R2c to R4c are hydroxyl groups and the remainder is a hydrogen atom.

As the repeating units having any of the partial structures of the general formulae (VIIa) to (VIId), there can be mentioned those of the following general formulae (AIIa) to (AIId).

(AIIa)

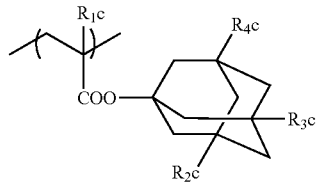

(AIIb)

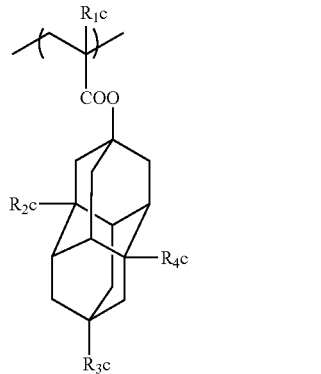

(AIIc)

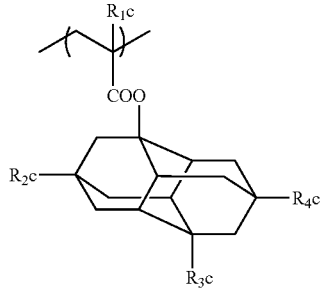

-continued

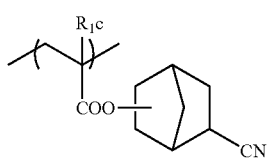
(AIId)

In the general formulae (AIIa) to (AIId),

R1c represents a hydrogen atom, a methyl group, a trifluoromethyl group or a hydroxymethyl group.

R2c to R4c have the same meaning as those of the general formulae (VIIa) to (VIII).

The content of the repeating unit having a hydroxyl group or a cyano group, based on all the repeating units of the resin (B), is preferably in the range of 5 to 40 mol %, more preferably 5 to 30 mol % and still more preferably 10 to 25 mol %.

Specific examples of the repeating units having a hydroxyl group or a cyano group will be shown below, which however in no way limit the scope of the present invention.

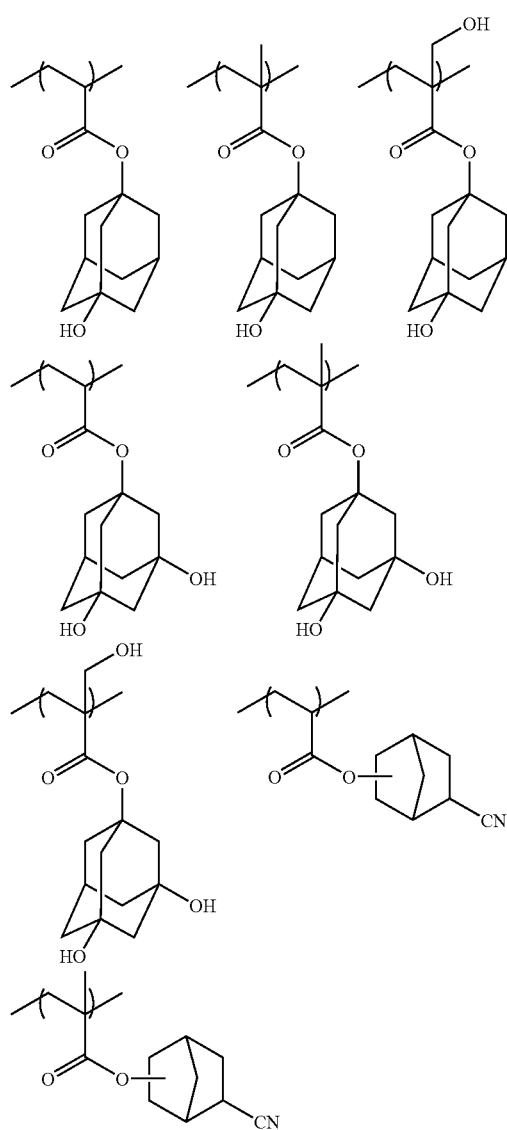

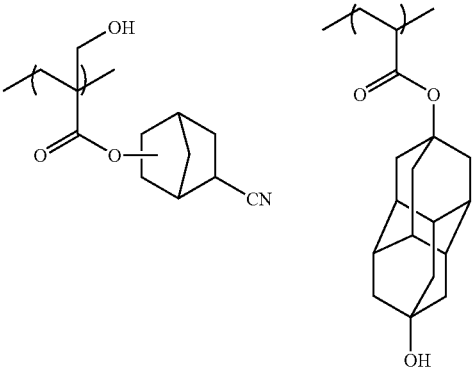

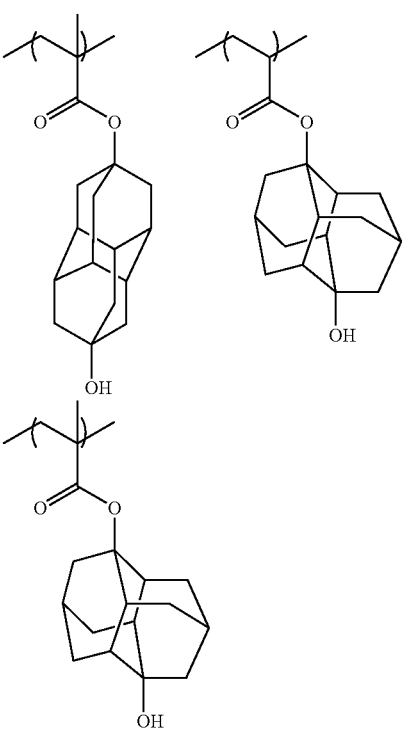

It is preferred for the resin as the component (B) to contain a repeating unit having an alkali-soluble group. As the alkali-soluble group, there can be mentioned a carboxyl group, a sulfonamido group, a sulfonylimido group, a bisulfonylimido group or an aliphatic alcohol substituted at its α-position with an electron-withdrawing group (for example, a hexafluoroisopropanol group). The possession of a repeating unit having a carboxyl group is more preferred. The incorporation of the repeating unit having an alkali-soluble group would increase the resolving power in contact hole usage. The repeating unit having an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a cyclohydrocarbon structure of a single ring or multiple rings. The repeating unit of acrylic acid or methacrylic acid is especially preferred.

The content of the repeating unit having an alkali-soluble group based on all the repeating units of the resin (A) is preferably in the range of 0 to 20 mol %, more preferably 3 to 15 mol % and still more preferably 5 to 10 mol %.

Specific examples of the repeating units having an alkali-soluble group will be shown below, which however in no way limit the scope of the present invention.

In the formulae, Rx represents H, CH$_3$, CF$_3$, or CH$_2$OH.

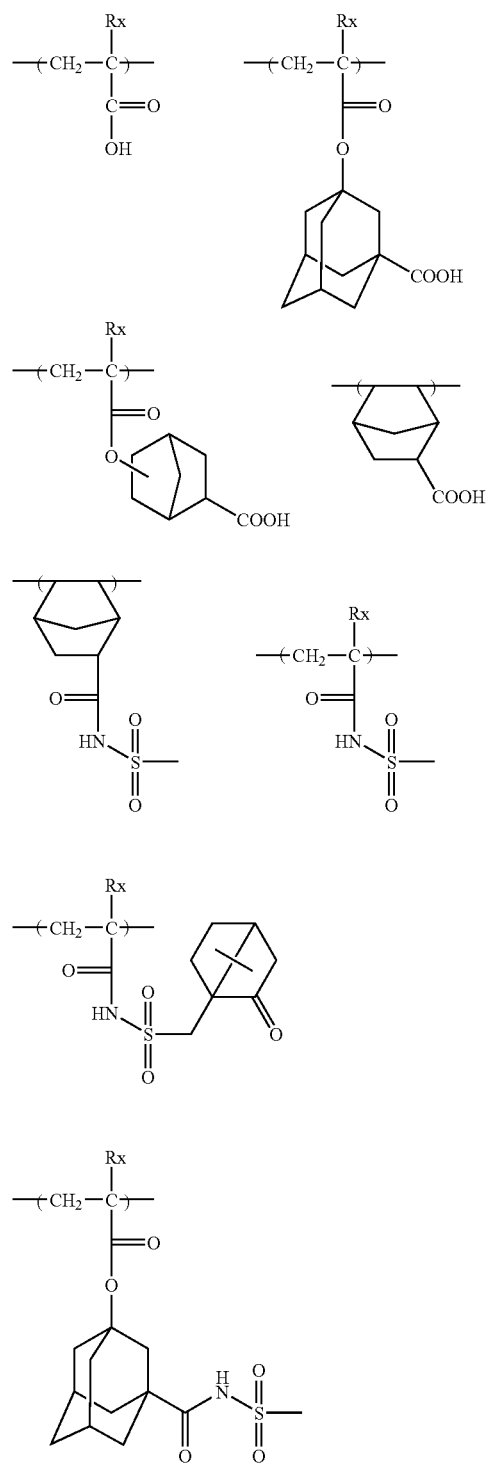
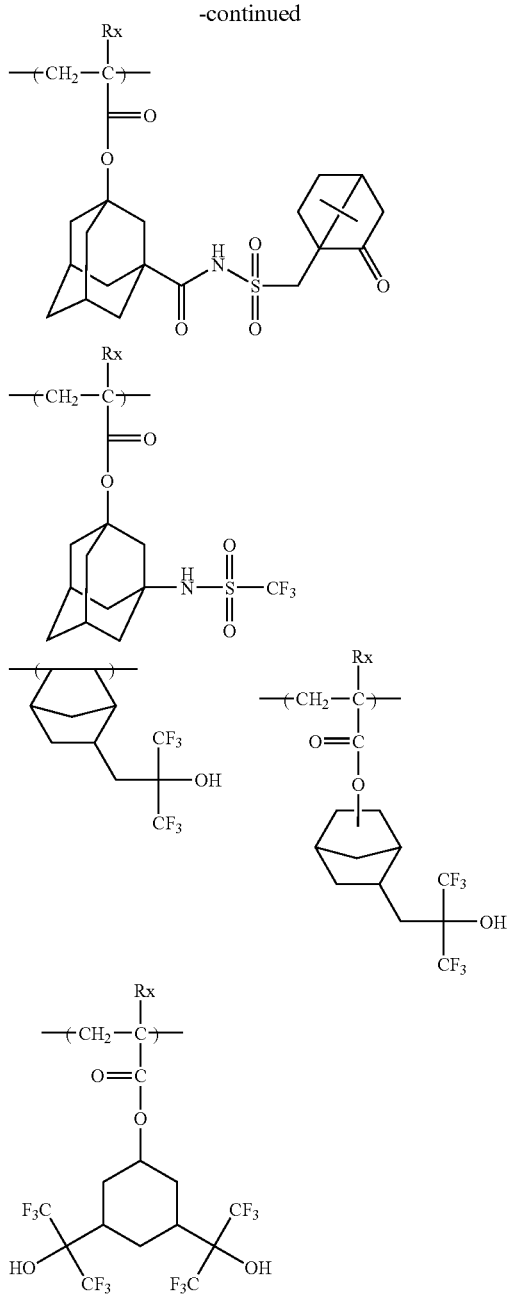

The repeating unit having at least one group selected from among a lactone group, a hydroxyl group, a cyano group and an alkali soluble group is preferably a repeating unit having at least two groups selected from among a lactone group, a hydroxyl group, a cyano group and an alkali soluble group and more preferably a repeating unit having a cyano group and a lactone group. A repeating unit of the structure wherein the above lactone structure (LC1-4) is substituted with a cyano group is especially preferred.

The resin (B) may further have a repeating unit having an alicyclic hydrocarbon structure and not exhibiting any acid decomposability. This would reduce any leaching of low-molecular components from a resist film into a liquid for liquid immersion at the time of liquid immersion exposure. As such a repeating unit, there can be mentioned, for example, 1-adamantyl (meth)acrylate repeating unit, diamantyl (meth)

acrylate repeating unit, tricyclodecanyl (meth)acrylate repeating unit, cyclohexyl (meth)acrylate repeating unit or the like.

The resin (B) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would enable fine regulation of the required properties of the resin (B), especially:

(1) solubility in applied solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in the resin (B) are appropriately determined from the viewpoint of regulation of not only the dry etching resistance of the resist but also the standard developer adaptability, substrate adhesion, resist profile and generally required properties of the resist such as the resolving power, heat resistance and sensitivity.

When the positive photosensitive composition of the present invention is one for ArF exposure, it is preferred for the resin as the component (B) to have no aromatic group from the viewpoint of transparency to ArF beams.

In the resin (B), preferably, all the repeating units consist of (meth)acrylate repeating units. In that instance, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units. It is more preferred to employ a copolymer containing 20 to 50 mol % of (meth)acrylate repeating units having an acid-decomposable group according to the general formula (AI), 20 to 50 mol % of (meth)acrylate repeating units having a lactone group, 5 to 30 mol % of (meth)acrylate repeating units having an alicyclic hydrocarbon structure substituted with a hydroxyl group or a cyano group and 0 to 20 mol % of other (meth)acrylate repeating units.

When the positive photosensitive composition of the present invention is exposed to KrF excimer laser beams, electron beams, X-rays or high-energy light rays of wavelength 50 nm or shorter (EUV, etc.), it is preferred for the resin as component B to have hydroxystyrene repeating units. More preferably, the resin as component B is a copolymer of hydroxystyrene/hydroxystyrene protected by an acid-decomposable group (this protective group is preferably an acetal protective group) or a copolymer of hydroxystyrene/(meth) acrylic acid tertiary alkyl ester.

Moreover, these resins with a hydroxystyrene repeating unit may further contain a repeating unit having in its side chain any of a cycloalkyl group (preferably monocyclic, for example, cyclohexyl), an aryl group (preferably, phenyl, naphthyl or biphenyl) and an aralkyl group (preferably, benzyl), which repeating unit has no acid decomposability. It is preferred for the principal-chain of this repeating unit to consist of (meth)acrylic acid. It can be expected that regulation of dissolution contrast, enhancement of etching resistance, etc. will be attained by the introduction of this repeating unit.

Particular examples of the resins having hydroxystyrene repeating units for use in the present invention will be shown below, which however in no way limit the scope of the present invention.

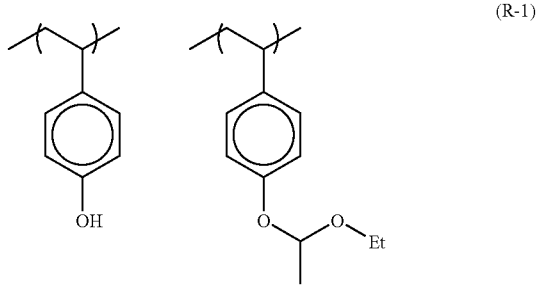

(R-1)

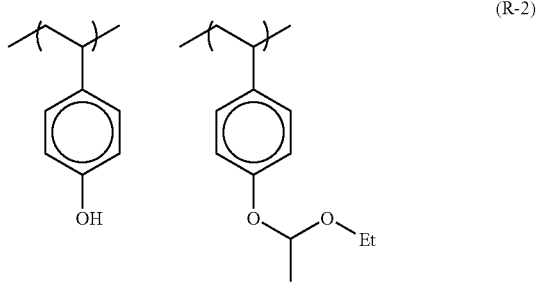

(R-2)

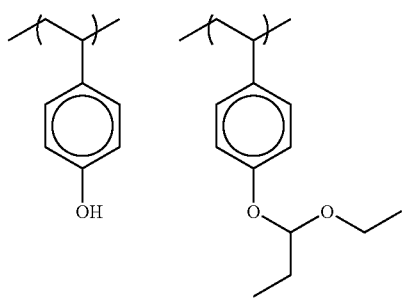

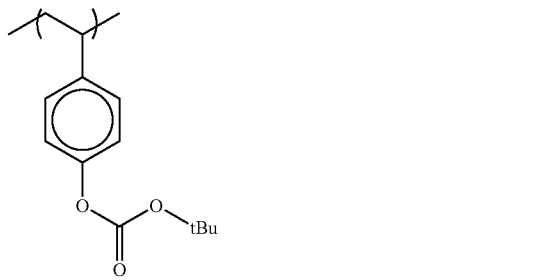

(R-3)

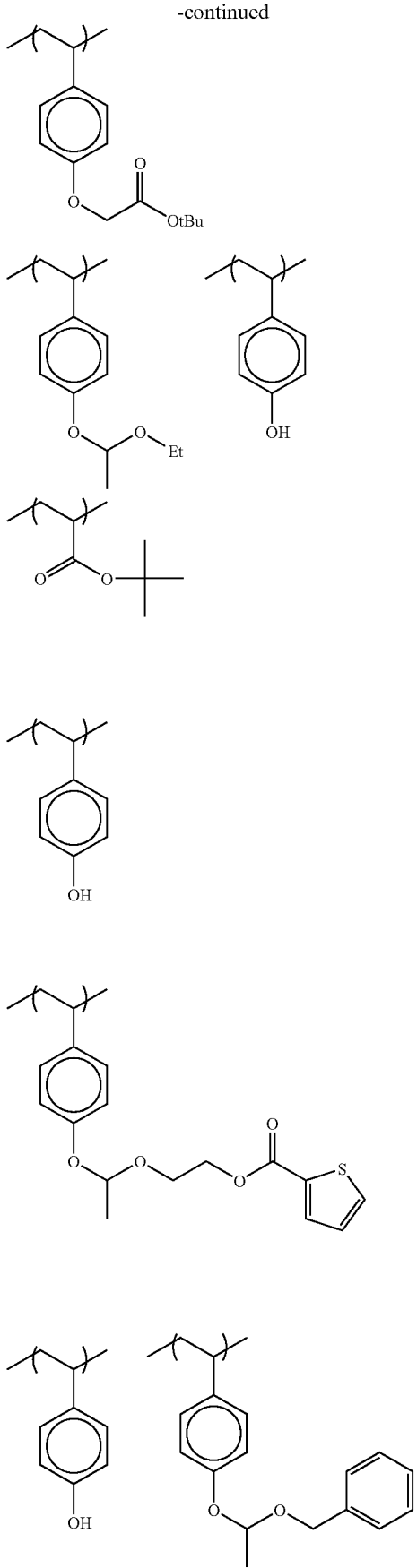
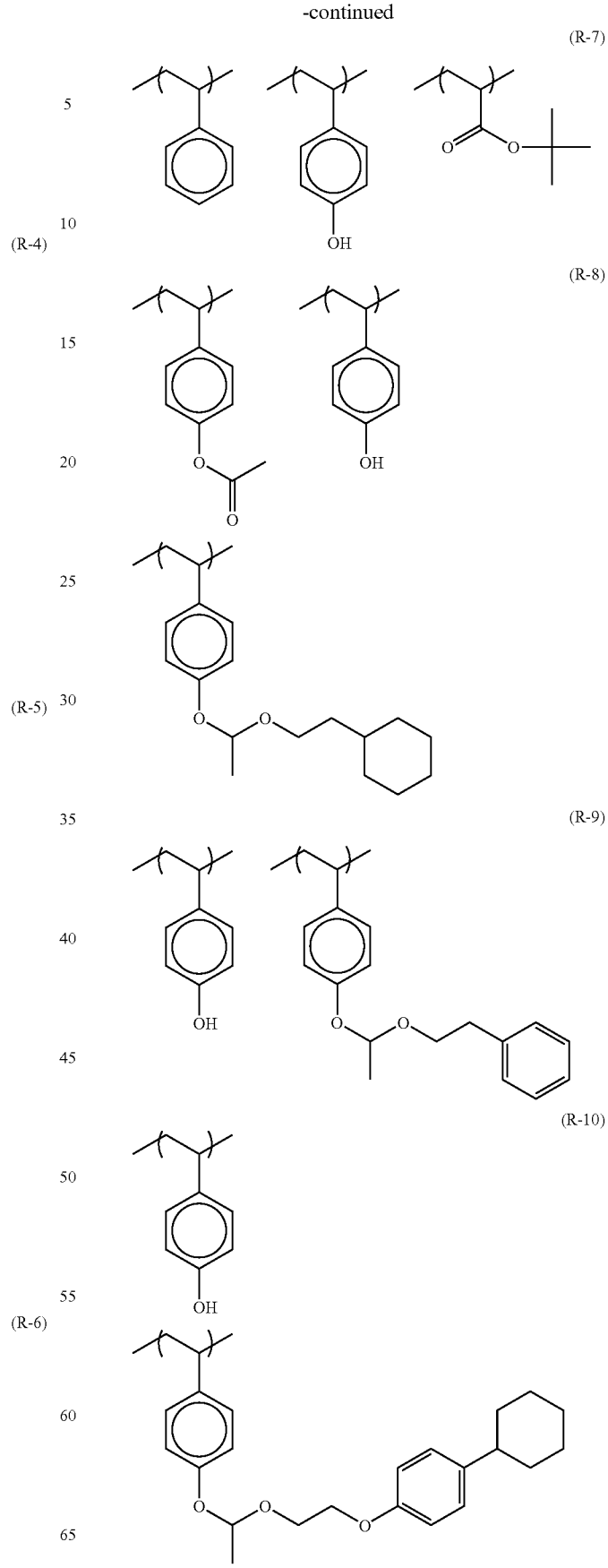

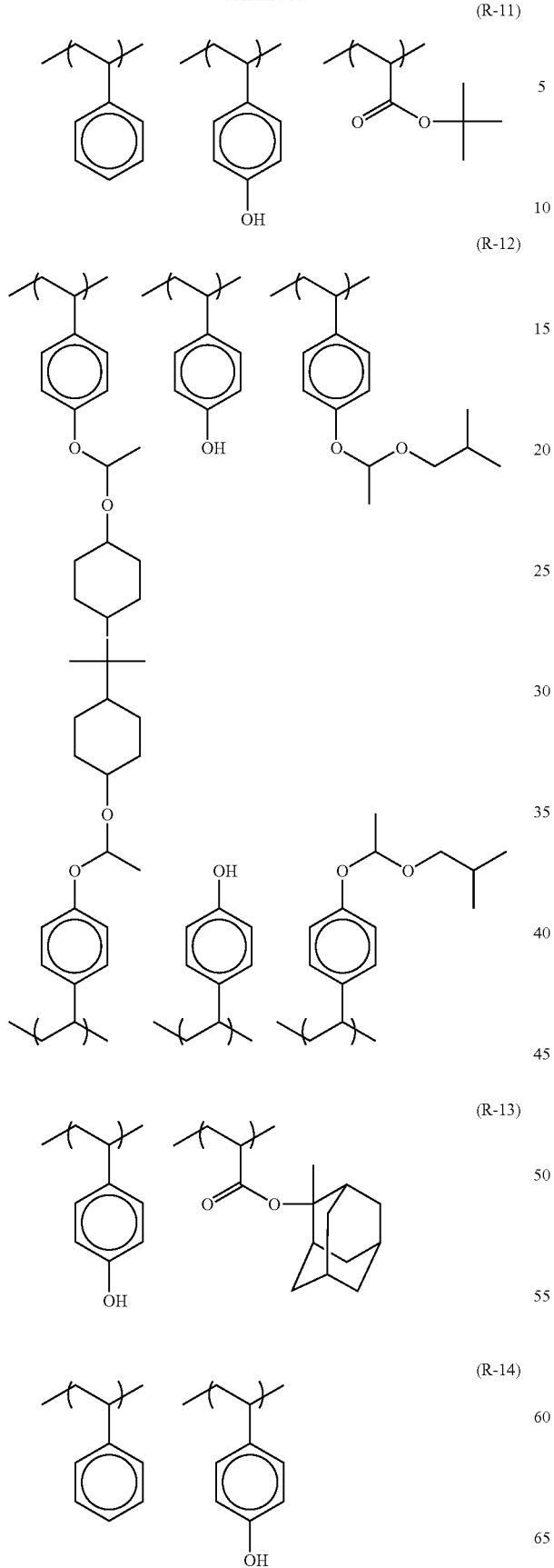
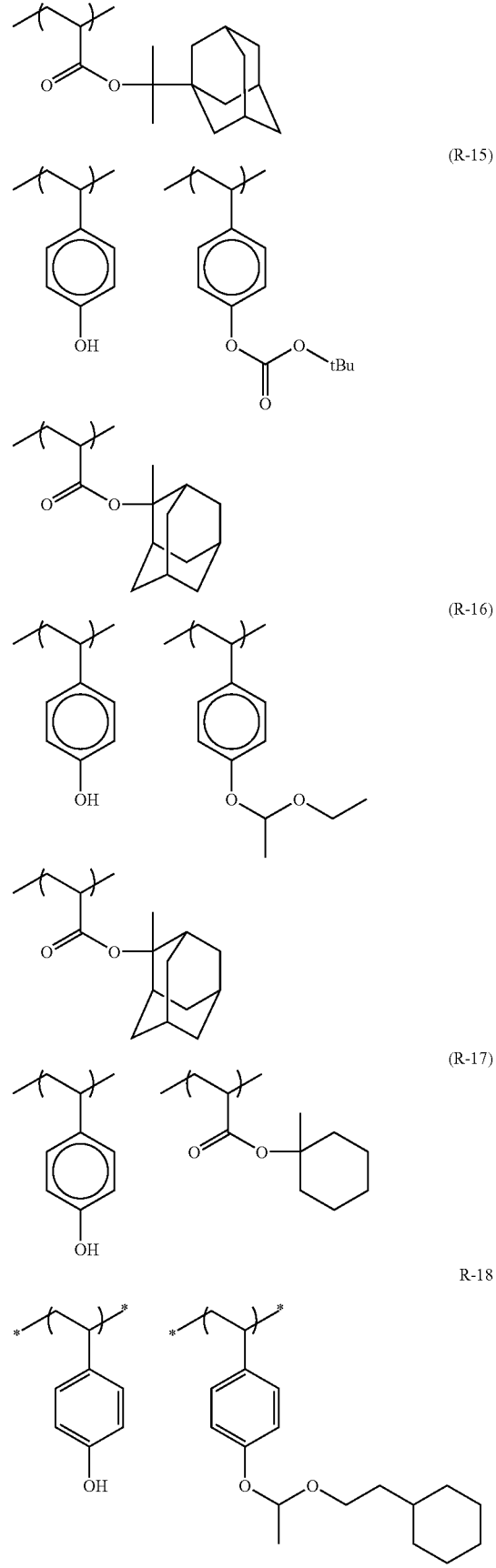

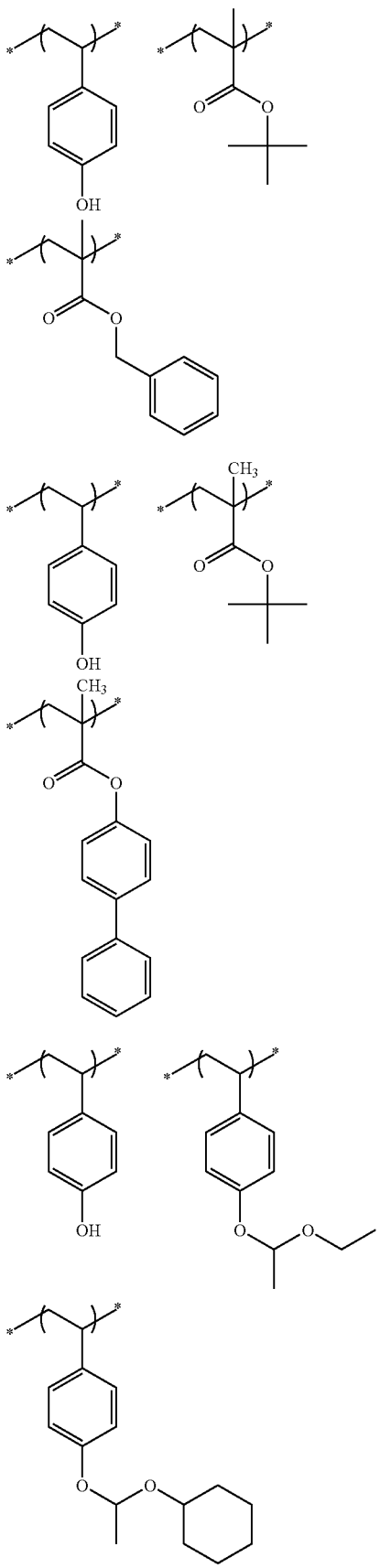

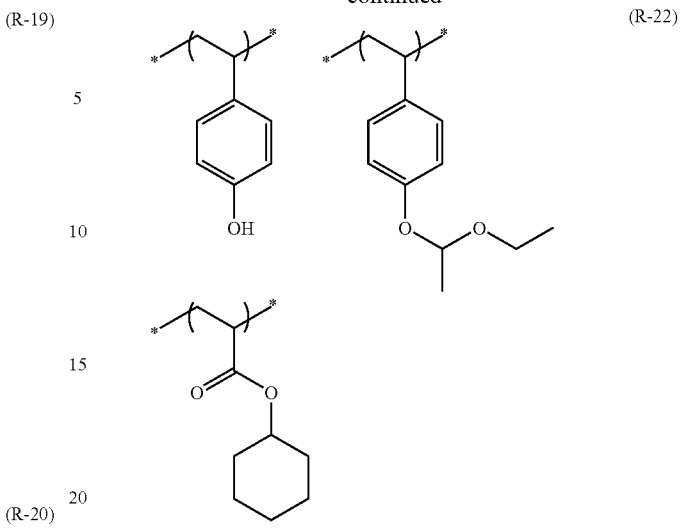

In the above particular examples, tBu represents a t-butyl group.

The content of acid-decomposable group is expressed by the formula B/(B+S) wherein B refers to the number of acid-decomposable groups contained in the resin and S refers to the number of alkali-soluble groups not protected by any acid-eliminable group. The content is preferably in the range of 0.01 to 0.7, more preferably 0.05 to 0.50 and further preferably 0.05 to 0.40.

The resin (B) can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or the latter described solvent capable of dissolving the composition of the present invention, such as propylene glycol monomethyl ether acetate, propylene glycol monomethyl ether or cyclohexanone. It is preferred to perform the polymerization with the use of the same solvent as employed in the photosensitive composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 30° to 120° C. and more preferably 60° to 100° C.

The weight average molecular weight of the resin (A) in terms of polystyrene molecular weight as measured by GPC is preferably in the range of 1000 to 200,000, more preferably 2000 to 20,000, still more preferably 3000 to 15,000 and further preferably 3000 to 10,000. The regulation of the weight average molecular weight to 1000 to 200,000 would prevent deteriorations of heat resistance and dry etching resistance and also prevent deterioration of developability and increase of viscosity leading to poor film forming property.

Use is made of the resin whose degree of dispersal (molecular weight distribution) is generally in the range of 1 to 3, preferably 1 to 2.6, more preferably 1 to 2 and most preferably 1.4 to 1.7. The lower the molecular weight distribution, the more excellent the resolving power and resist profile and the smoother the side wall of the resist pattern to thereby attain an excellence in roughness.

The content of the resin (B) in the positive photosensitive composition of the present invention based on the total solids thereof is preferably in the range of 50 to 99.9 mass %, more preferably 60 to 99.0 mass %.

In the present invention, use may be made of either solely one or two or more of the resins as the component (B).

[Solvent]

The photosensitive composition of the present invention may contain a solvent. The solvent is not limited as long as it can be used in the preparation of a positive resist composition through dissolution of the above-mentioned components. As the solvent, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As preferred alkylene glycol monoalkyl ether carboxylates, there can be mentioned, for example, propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

As preferred alkylene glycol monoalkyl ethers, there can be mentioned, for example, propylene glycol monomethyl ether, propylene glycol monoethyl ether, propylene glycol monopropyl ether, propylene glycol monobutyl ether, ethylene glycol monomethyl ether and ethylene glycol monoethyl ether.

As preferred alkyl lactates, there can be mentioned, for example, methyl lactate, ethyl lactate, propyl lactate and butyl lactate.

As preferred alkyl alkoxypropionates, there can be mentioned, for example, ethyl 3-ethoxypropionate, methyl 3-methoxypropionate, methyl 3-ethoxypropionate and ethyl 3-methoxypropionate.

As preferred cyclolactones, there can be mentioned, for example, β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

As preferred optionally cyclized monoketone compounds, there can be mentioned, for example, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

As preferred alkylene carbonates, there can be mentioned, for example, propylene carbonate, vinylene carbonate, ethylene carbonate and butylene carbonate.

As preferred alkyl alkoxyacetates, there can be mentioned, for example, acetic acid 2-methoxyethyl ester, acetic acid 2-ethoxyethyl ester, acetic acid 2-(2-ethoxyethoxy)ethyl ester, acetic acid 3-methoxy-3-methylbutyl ester and acetic acid 1-methoxy-2-propyl ester.

As preferred alkyl pyruvates, there can be mentioned, for example, methyl pyruvate, ethyl pyruvate and propyl pyruvate.

As a preferably employable solvent, there can be mentioned a solvent having a boiling point of 130° C. or above measured at ordinary temperature under ordinary pressure. For example, there can be mentioned cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, acetic acid 2-ethoxyethyl ester, acetic acid 2-(2-ethoxyethoxy)ethyl ester or propylene carbonate.

In the present invention, these solvents may be used either individually or in combination.

In the present invention, a mixed solvent consisting of a mixture of a solvent having a hydroxyl group in its structure and a solvent having no hydroxyl group may be used as the organic solvent.

As the solvent having a hydroxyl group, there can be mentioned, for example, ethylene glycol, ethylene glycol monomethyl ether, ethylene glycol monoethyl ether, propylene glycol, propylene glycol monomethyl ether, propylene glycol monoethyl ether, ethyl lactate or the like. Of these, propylene glycol monomethyl ether and ethyl lactate are especially preferred.

As the solvent having no hydroxyl group, there can be mentioned, for example, propylene glycol monomethyl ether acetate, ethyl ethoxypropionate, 2-heptanone, γ-butyrolactone, cyclohexanone, butyl acetate, N-methylpyrrolidone, N,N-dimethylacetamide, dimethyl sulfoxide or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent having a hydroxyl group and a solvent having no hydroxyl group is in the range of 1/99 to 99/1, preferably 10/90 to 90/10 and more preferably 20/80 to 60/40. The mixed solvent containing 50 mass % or more of a solvent having no hydroxyl group is especially preferred from the viewpoint of uniform applicability.

It is preferred for the solvent to be a mixed solvent consisting of two or more solvents containing propylene glycol monomethyl ether acetate.

[Basic Compound]

The photosensitive composition of the present invention preferably contains a basic compound so as to decrease any performance alteration over time from exposure to heating.

As preferred basic compounds, there can be mentioned the compounds having the structures of the following formulae (A) to (E).

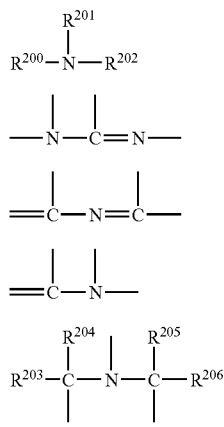

In the general formulae (A) and (E), $R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded with each other to thereby form a ring.

$R^{203}$, $R^{204}$, $R^{205}$ and $R^{206}$ may be identical to or different from each other and each represent an alkyl group having 1 to 20 carbon atoms.

With respect to the above alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

More preferably, in these general formulae (A) and (E) the alkyl group is unsubstituted.

As preferred compounds, there can be mentioned guanidine, aminopyrrolidine, pyrazole, pyrazoline, piperazine, aminomorpholine, aminoalkylmorpholine, piperidine and the like. Further, as preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole, 2-phenylbenzoimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, acetate, adamantane-1-carboxylate, perfluoroalkyl carboxylate and the like. As the compounds with a trialkylamine structure, there can be mentioned tri(n-butyl)amine, tri(n-octyl)amine and the like. As the aniline compounds, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, N-phenyldiethanolamine, tris(methoxyethoxyethyl)amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

As the amine compound, use can be made of primary, secondary and tertiary amine compounds. An amine compound having its at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the amine compounds, it is preferred for the alkyl chain to contain an oxygen atom so as to form an oxyalkylene group. The number of oxyalkylene groups in each molecule is one or more, preferably 3 to 9 and more preferably 4 to 6. The oxyalkylene group is preferably an oxyethylene group ($-CH_2CH_2O-$) or an oxypropylene group ($-CH(CH_3)CH_2O-$ or $-CH_2CH_2CH_2O-$), more preferably an oxyethylene group.

As the ammonium salt compound, use can be made of primary, secondary, tertiary and quaternary ammonium salt compounds. An ammonium salt compound having its at least one alkyl group bonded to the nitrogen atom thereof is preferred. Of the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. Of the ammonium salt compounds, it is preferred for the alkyl chain to contain an oxygen atom so as to form an oxyalkylene group. The number of oxyalkylene groups in each molecule is one or more, preferably 3 to 9 and still more preferably 4 to 6. The oxyalkylene group is preferably an oxyethylene group ($-CH_2CH_2O-$) or an oxypropylene group ($-CH(CH_3)CH_2O-$ or $-CH_2CH_2CH_2O-$), more preferably an oxyethylene group.

As the anion of the ammonium salt compounds, there can be mentioned a halide atom, a sulfonate, a borate, a phosphate or the like. Of these, a halide and a sulfonate are preferred. Among halides, chloride, bromide and iodide are especially preferred. Among sulfonates, an organic sulfonate having 1 to 20 carbon atoms is especially preferred. As the organic sulfonate, there can be mentioned an aryl sulfonate and an alkyl sulfonate having 1 to 20 carbon atoms. The alkyl group of the alkyl sulfonate may have a substituent. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group of the aryl sulfonate, there can be mentioned a benzene ring, a naphthalene ring or an anthracene ring. The benzene ring, naphthalene ring or anthracene ring may have a substituent. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound having a phenoxy group and ammonium salt compound having a phenoxy group are those having a phenoxy group at the end of the alkyl group of the amine compound or ammonium salt compound opposed to the nitrogen atom. The phenoxy group may have a substituent. As the substituent of the phenoxy group, there can be mentioned, for example, an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The substitution position of the substituent may be any of 2- to 6-positions. The number of substituents is optional within the range of 1 to 5.

It is preferred that at least one oxyalkylene group exist between the phenoxy group and the nitrogen atom. The number of oxyalkylene groups in each molecule is one or more, preferably 3 to 9 and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

The sulfonic ester group of the amine compound having a sulfonic ester group or ammonium salt compound having a sulfonic ester group may be any of an alkylsulfonic ester, a cycloalkylsulfonic ester and an arylsulfonic ester. In the alkylsulfonic ester, the alkyl group preferably has 1 to 20 carbon atoms. In the cycloalkylsulfonic ester, the cycloalkyl group preferably has 3 to 20 carbon atoms. In the arylsulfonic ester, the aryl group preferably has 6 to 12 carbon atoms. The alkylsulfonic ester, cycloalkylsulfonic ester and arylsulfonic ester may have substituents. As preferred substituents, there can be mentioned a halogen atom, a cyano group, a nitro group, a carboxyl group, a carboxylic ester group and a sulfonic ester group.

It is preferred that at least one oxyalkylene group exist between the sulfonic ester group and the nitrogen atom. The number of oxyalkylene groups in each molecule is one or more, preferably 3 to 9 and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

These basic compounds are used either individually or in combination.

The amount of basic compound used is generally in the range of 0.001 to 10 mass %, preferably 0.01 to 5 mass % based on the solid contents of the positive photosensitive composition.

With respect to the ratio of the acid generator to basic compound used in the composition, preferably, the acid generator/basic compound (molar ratio)=2.5 to 300. The reason for this is that the molar ratio is preferred to be 2.5 or higher from the viewpoint of sensitivity and resolving power. The molar ratio is preferred to be 300 or below from the viewpoint of the inhibition of any resolving power deterioration due to thickening of resist pattern over time from exposure to heating treatment. The acid generator/basic compound (molar ratio) is more preferably in the range of 5.0 to 200, still more preferably 7.0 to 150.

[Surfactant]

The positive photosensitive composition of the present invention preferably further contains a surfactant, and more preferably contains any one, or two or more members, of fluorinated and/or siliconized surfactants (fluorinated surfactant, siliconized surfactant and surfactant containing both fluorine and silicon atoms).

The positive photosensitive composition of the present invention when containing the above surfactant would, in the use of an exposure light source of 250 nm or below, especially 220 nm or below, realize favorable sensitivity and resolving power and produce a resist pattern with less adhesion and development defects.

As the fluorinated and/or siliconized surfactants, there can be mentioned, for example, those described in JP-A's-62-36663, 61-226746, 61-226745, 62-170950, 63-34540, 7-230165, 8-62834, 9-54432, 9-5988 and 2002-277862 and U.S. Pat. Nos. 5,405,720, 5,360,692, 5,529,881, 5,296,330, 5,436,098, 5,576,143, 5,294,511 and 5,824,451. Any of the following commercially available surfactants can be used as is.

As useful commercially available surfactants, there can be mentioned, for example, fluorinated surfactants/siliconized surfactants, such as Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105 and 106 (produced by Asahi Glass Co., Ltd.), Troy Sol S-366 (produced by Troy Chemical Co., Ltd.), GF-300 and GF-150 (produced by TOAGOSEI CO., LTD.), Sarfron 5-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer having a fluorinated aliphatic group derived from a fluorinated aliphatic compound, produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly(oxyalkylene) methacrylate, which copolymer may have an irregular distribution or may result from block copolymerization. As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation). Moreover, the copolymer from a monomer having a fluorinated aliphatic group and a poly(oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene) acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene) acrylate (or methacrylate), a copolymer from an acrylate (or methacrylate) having a $C_3F_7$ group, poly(oxyethylene) acrylate (or methacrylate) and poly(oxypropylene) acrylate (or methacrylate), or the like.

In the present invention, surfactants other than the fluorinated and/or siliconized surfactants can also be employed. In particular, there can be mentioned, for example, nonionic surfactants including a polyoxyethylene alkyl ether such as polyoxyethylene lauryl ether, polyoxyethylene stearyl ether, polyoxyethylene cetyl ether or polyoxyethylene oleyl ether, a polyoxyethylene alkylaryl ether such as polyoxyethylene octylphenol ether or polyoxyethylene nonylphenol ether, a polyoxyethylene-polyoxypropylene block copolymer, a sorbitan fatty acid ester such as sorbitan monolaurate, sorbitan monopalmitate, sorbitan monostearate, sorbitan monooleate, sorbitan trioleate or sorbitan tristearate, a polyoxyethylene sorbitan fatty acid ester such as polyoxyethylene sorbitan monolaurate, polyoxyethylene sorbitan monopalmitate, polyoxyethylene sorbitan monostearate, polyoxyethylene sorbitan trioleate or polyoxyethylene sorbitan tristearate, or the like.

These surfactants may be used either individually or in combination.

The amount of each surfactant used is preferably in the range of 0.0001 to 2 mass %, more preferably 0.001 to 1 mass % based on the total mass of the photosensitive composition (excluding the solvent).

[Carboxylic Acid Onium Salt]

The positive photosensitive composition of the present invention may contain a carboxylic acid onium salt. As the carboxylic acid onium salt, there can be mentioned, for example, a carboxylic acid sulfonium salt, a carboxylic acid iodonium salt, a carboxylic acid ammonium salt or the like. The especially preferred carboxylic acid onium salts are the iodonium salt and the sulfonium salt. It is preferred for the carboxylate residue of the carboxylic acid onium salt for use in the present invention to be one containing neither an aromatic group nor a carbon-carbon double bond. In particular, the especially preferred anion moiety thereof is a linear or branched cycloalkylcarboxylate anion of a single ring or multiple rings having 1 to 30 carbon atoms. A more preferred anion moiety is an anion of carboxylic acid wherein the alkyl group is partially or wholly fluorinated. The alkyl chain may contain an oxygen atom. Accordingly, there would be achieved securement of the transparency in 220 nm or shorter light, enhancement of the sensitivity and resolving power and improvement of the dependency on density distribution and exposure margin.

As the fluorinated carboxylic acid anion, there can be mentioned any of the anions of fluoroacetic acid, difluoroacetic acid, trifluoroacetic acid, pentafluoropropionic acid, heptafluorobutyric acid, nonafluoropentanoic acid, perfluorododecanoic acid, perfluorotridecanoic acid, perfluorocyclohexanecarboxylic acid and 2,2-bistrifluoromethylpropionic acid, or the like.

These carboxylic acid onium salts can be synthesized by reacting a sulfonium hydroxide, an iodonium hydroxide or an ammonium hydroxide and a carboxylic acid with silver oxide in an appropriate solvent.

The content of each carboxylic acid onium salt in the composition is generally in the range of 0.1 to 20 mass %, preferably 0.5 to 10 mass % and still more preferably 1 to 7 mass % based on the total solids of the composition.

[Dissolution Inhibiting Compound]

The positive photosensitive composition of the present invention may contain a dissolution inhibiting compound of 3000 or less molecular weight that is decomposed by the action of an acid to thereby increase the solubility in an alkali developer (hereinafter referred to as "dissolution inhibiting compound").

From the viewpoint of preventing any lowering of 220 nm or shorter transmission, the dissolution inhibiting compound is preferably an alicyclic or aliphatic compound having an acid-decomposable group, such as any of cholic acid derivatives having an acid-decomposable group described in Proceeding of SPIE, 2724, 355 (1996). The acid-decomposable group and alicyclic structure are the same as described with respect to the resin as the component (B).

When the positive photosensitive composition of the present invention is exposed to a KrF excimer laser or irradiated with electron beams, preferred use is made of one having a structure resulting from substitution of the phenolic hydroxyl group of a phenol compound with an acid-decomposable group. The phenol compound preferably contains 1 to 9 phenol skeletons, more preferably 2 to 6 phenol skeletons.

In the present invention, the molecular weight of each dissolution inhibiting compound is 3000 or less, preferably 300 to 3000 and more preferably 500 to 2500.

The amount of dissolution inhibiting compound added is preferably in the range of 3 to 50 mass %, more preferably 5 to 40 mass % based on the total solids of the positive photosensitive composition.

Specific examples of the dissolution inhibiting compounds will be shown below, which however in no way limit the scope of the present invention.

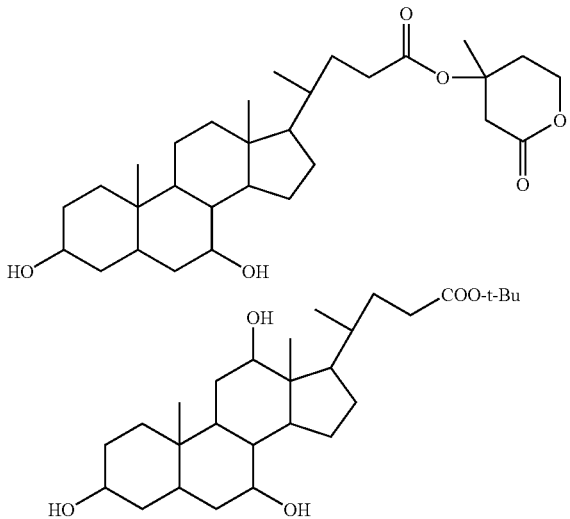

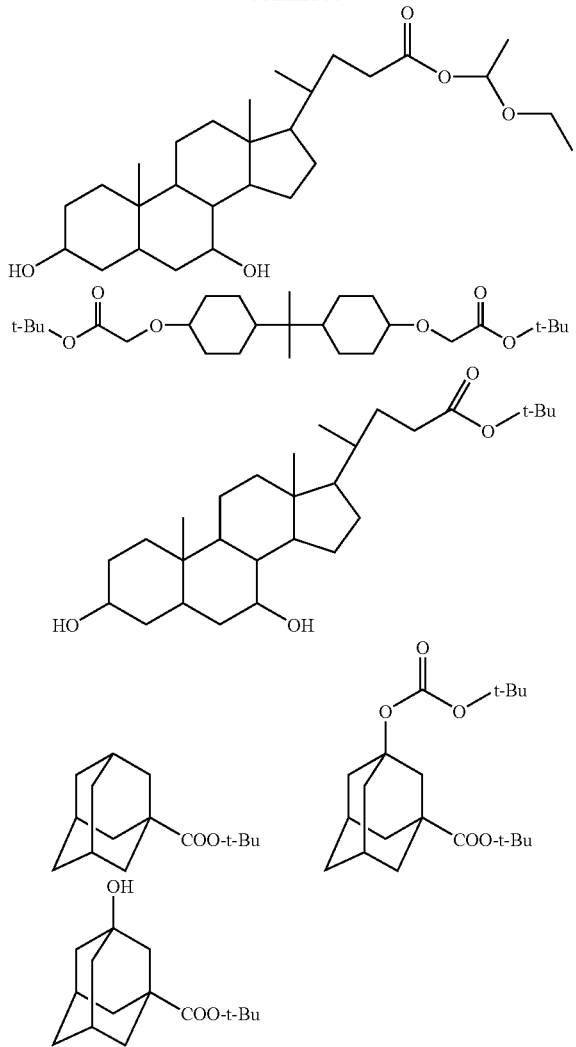

[Other Additives]

The photosensitive composition of the present invention may further according to necessity contain a dye, a plasticizer, a photosensitizer, a light absorber, a compound capable of increasing the solubility in a developer (for example, a phenolic compound of 1000 or less molecular weight or a carboxylated alicyclic or aliphatic compound), etc.

The above phenolic compound of 1000 or less molecular weight can be easily synthesized by persons of ordinary skill in the art to which the present invention pertains while consulting the processes described in, for example, JP-As 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

Method of Forming Pattern

From the viewpoint of enhancement of resolving power, it is preferred for the positive photosensitive composition of the present invention to be used with a coating thickness of 30 to 250 nm. More preferably, the photosensitive composition is used with a coating thickness of 30 to 200 nm. This coating thickness can be attained by setting the solid content of the photosensitive composition within an appropriate range so as to cause the composition to have an appropriate viscosity, thereby improving the applicability and film forming property.

The total solids content of the positive photosensitive composition is generally in the range of 1 to 10 mass %, preferably 1 to 8.0 mass % and more preferably 1.0 to 6.0 mass %.

The positive photosensitive composition of the present invention is used in such a manner that the above components are dissolved in a given organic solvent, preferably the above mixed solvent, and filtered and applied onto a given support in the following manner. The filter medium for the filtration preferably consists of a polytetrafluoroethylene, polyethylene or nylon having a pore size of 0.1 μm or less, especially 0.05 μm or less and more especially 0.03 μm or less.

For example, a positive photosensitive composition is applied onto a substrate, such as one for use in the production of precision integrated circuit elements (e.g., silicon/silicon dioxide coating), by appropriate application means, such as a spinner or coater, and dried to thereby form a resist film.

The resist film is exposed through a given mask to actinic rays or radiation, preferably baked (heated), and developed and rinsed. Accordingly, a desirable pattern can be obtained.

As the actinic rays or radiation, there can be mentioned infrared rays, visible light, ultraviolet rays, far ultraviolet rays, X-rays, electron beams or the like. Among them, preferred use is made of far ultraviolet rays of especially 250 nm or less, more especially 220 nm or less and still more especially 1 to 200 nm wavelength, such as a KrF excimer laser (248 nm), an ArF excimer laser (193 nm) and an $F_2$ excimer laser (157 nm), as well as X-rays, electron beams and the like. More preferred use is made of an ArF excimer laser, an $F_2$ excimer laser, EUV (13 nm) and electron beams.

Prior to the formation of a resist film, the substrate may be coated with an antireflection film.

As the antireflection film, use can be made of not only an inorganic film of titanium, titanium oxide, titanium nitride, chromium oxide, carbon, amorphous silicon or the like but also an organic film composed of a light absorber and a polymer material. Also, as the organic antireflection film, use can be made of commercially available organic antireflection films, such as the DUV30 Series and DUV40 Series produced by Brewer Science Inc. and AR-2, AR-3 and AR-5 produced by Shipley Co., Ltd.

In the development step, an alkali developer is used as follows. As the alkali developer for a positive resist composition, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and a surfactant may be added thereto.

The alkali concentration of the alkali developer is generally in the range of 0.1 to 20 mass %.

The pH value of the alkali developer is generally in the range of 10.0 to 15.0.

Before the use of the above alkaline aqueous solution, appropriate amounts of an alcohol and a surfactant may be added thereto.

Pure water can be used as the rinse liquid. Before the use, an appropriate amount of surfactant may be added thereto.

The development operation or rinse operation may be followed by the operation for removing any developer or rinse liquid adhering onto the pattern by the use of a supercritical fluid.

EXAMPLE

Now, the present invention will be described with reference to Examples, which however in no way limit the scope of the present invention.

Examples 1 to 14 and Comparative Examples 1 to 3

Synthesis of Photoacid Generators
<Synthesis of Compound $X_{10}$>

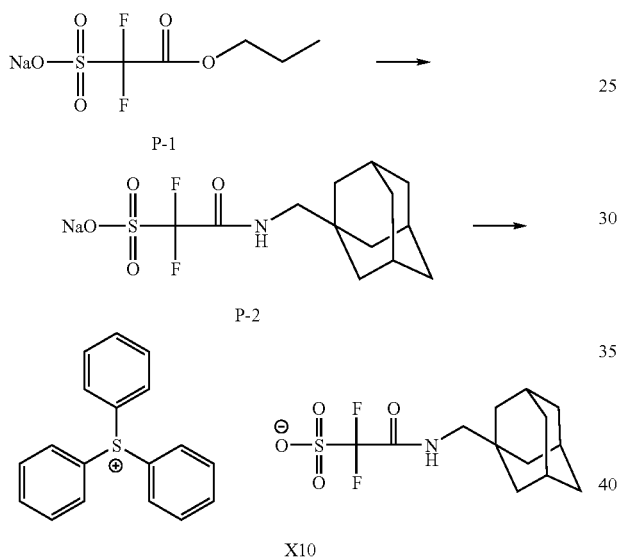

Compound P-1 was synthesized referring to the relevant method described in JP-A-2008-170983. Compound P-1 (3 g, purity 62.5%) was dissolved in THF (20 g), and 1-adamantanemethylamine (2.27 g) was added to the solution and agitated at room temperature for 12 hours. The thus obtained reaction mixture was concentrated by means of an evaporator, thereby obtaining crude product P-2 (white solid). The obtained crude product was dissolved in a liquid consisting of a mixture of 20 g of water and 20 g of acetonitrile, and triphenylsulfonium bromide (4.29 g) was added to the solution and agitated for 15 minutes. The thus obtained reaction mixture was concentrated and acetonitrile was removed by means of an evaporator. Extraction was carried out twice using 50 g of chloroform each time. The thus obtained organic layer was washed thrice using 100 g of deionized water each time. The washed organic layer was concentrated by means of an evaporator, thereby obtaining compound $X_{10}$ as a white solid (4.53 g, yield 62%).

The $^1$HNMR chart of obtained compound $X_{10}$ is shown in FIG. 1.

$^1$HNMR spectrum (DMSO-d6): σ (ppm) 1.429(6H,d), 1.598(6H,dd), 1.900(3H,s), 2.502(2H,m), 7.768-7.887 (15H, m), 7.889-8.000 (1H,M)

The other photoacid generators X11 to X13, X16, X21, X24 and X32 were also synthesized in the same manner as mentioned above.

Synthesis of Resins
<Synthesis of Resin RA-1>

In a nitrogen gas stream, 53.22 g of cyclohexanone was placed in a three-necked flask and heated at 80° C. A solution obtained by dissolving 12.42 g of 2-ethyl-2-adamantyl methacrylate, 8.51 g of γ-butyrolactone methacrylate and 5.91 g of 3-hydroxyadamantyl-1-methacrylate and further 1.43 g of initiator V601 (5.0 mol % based on monomers, produced by Wako Pure Chemical Industries, Ltd.) in 98.84 g of cyclohexanone was dropped thereinto over a period of 6 hours. After the completion of the dropping, reaction was continued at 80° C. for 2 hours. The thus obtained reaction mixture was allowed to stand still to cool and was dropped into a mixed liquid consisting of 900 ml of methanol and 100 ml of water over a period of 20 minutes. The thus precipitated powder was collected by filtration and dried, thereby obtaining 18 g of desired resin RA-1. The weight average molecular weight (Mw) of the obtained resin in terms of standard polystyrene molecular weight was 10,700 and the dispersity (Mw/Mn) thereof was 1.81.

In the same manner, other resins RA-2 to RA-12 were synthesized. The weight average molecular weights thereof were regulated by changing the amount of initiator added.

The repeating units (molar ratios), weight average molecular weight (Mw) and dispersity (Mw/Mn) with respect to each of the obtained resins are given below.

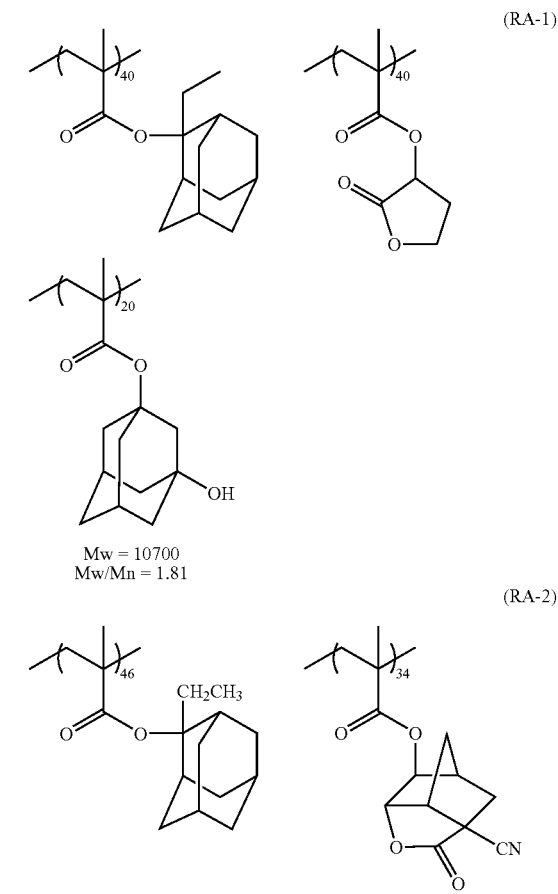

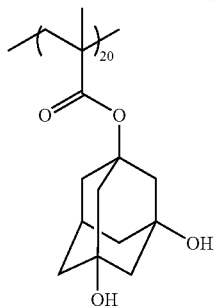
Mw = 9400
Mw/Mn = 1.78
(RA-3)
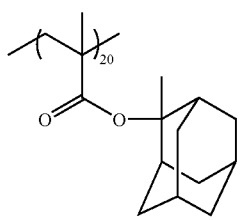
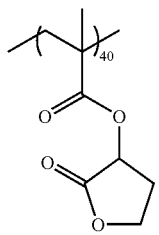
Mw = 13700
Mw/Mn = 1.89
(RA-4)
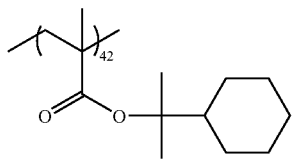
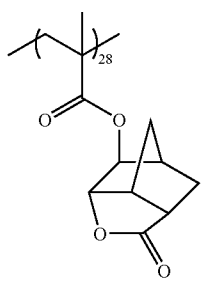
Mw = 10300
Mw/Mn = 1.90
(RA-5)
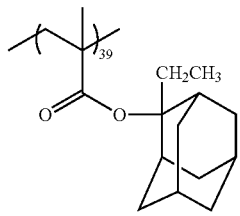
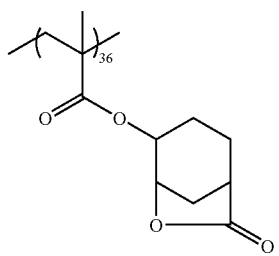
Mw = 8900
Mw/Mn = 1.80
(RA-6)
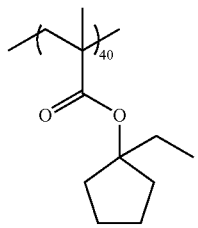
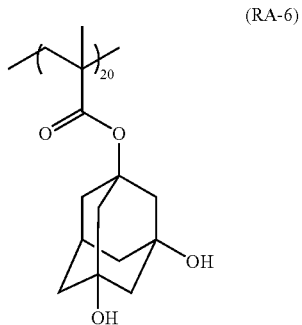
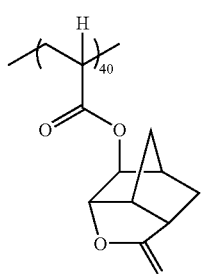
Mw = 7900
Mw/Mn = 1.73
(RA-7)
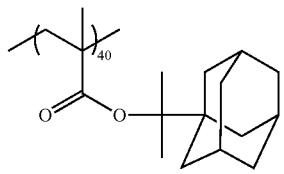

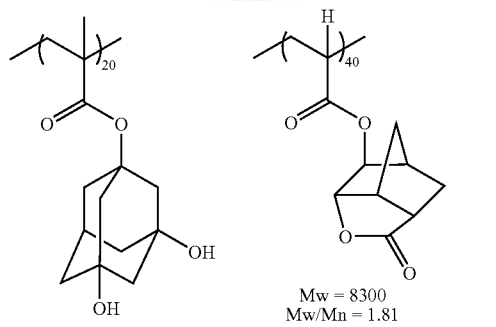
Mw = 8300
Mw/Mn = 1.81
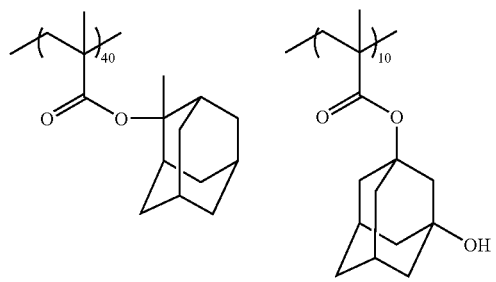
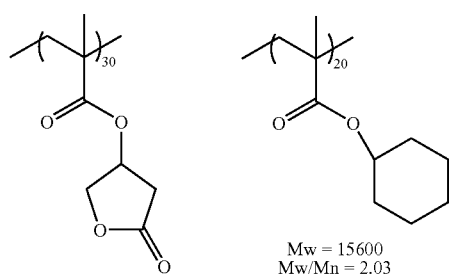
Mw = 15600
Mw/Mn = 2.03
(RA-9)
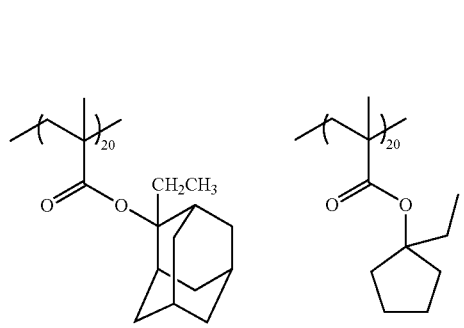
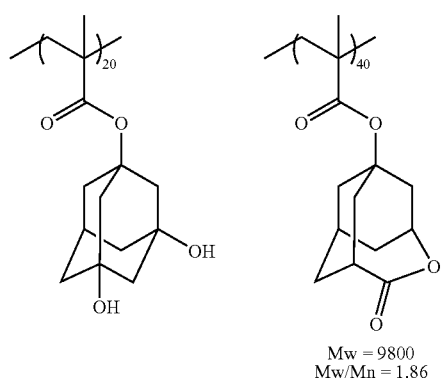
Mw = 9800
Mw/Mn = 1.86
(RA-10)
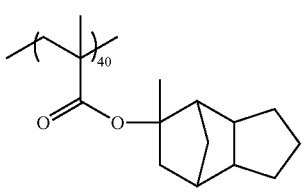
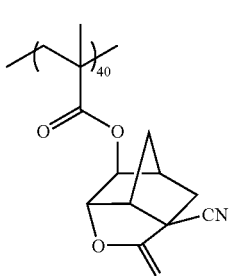
Mw = 18300
Mw/Mn = 2.10
(RA-11)
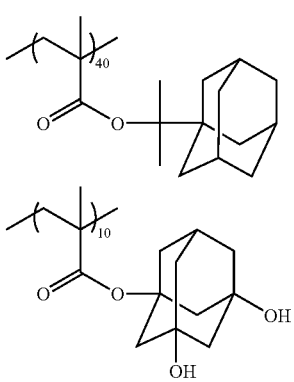
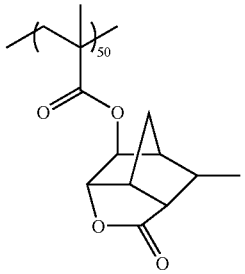
Mw = 6900
Mw/Mn = 1.71
(RA-12)
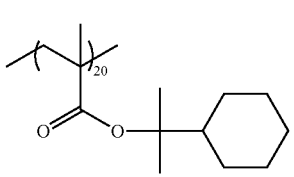

-continued

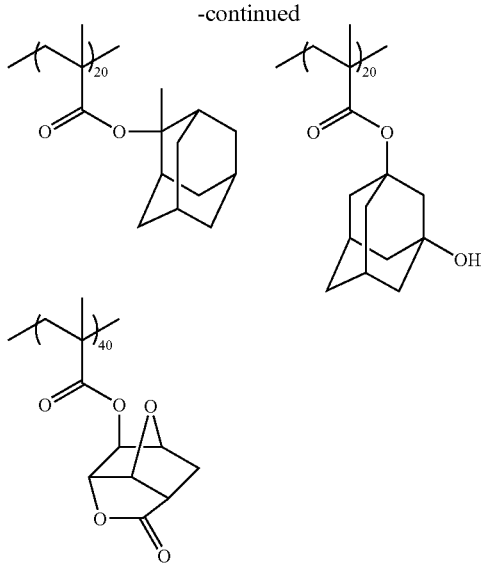

Mw = 8300
Mw/Mn = 1.81

<Preparation of Resists>

Referring to Table 1 given below, appropriate components were dissolved in solvents, thereby obtaining solutions of 5 mass % solid content. These solutions were passed through a polyethylene filter of 0.03 μm pore size, thereby obtaining positive resist solutions. The thus obtained positive resist solutions were evaluated by the following methods. The results are also given in Table 1.

<Evaluation of Resists>

An ARC29A organic antireflection film (produced by Nissan Chemical Industries, Ltd.) was applied onto a silicon wafer and baked at 205° C. for 60 seconds, thereby forming a 78 nm-thick antireflection film.

Each of the prepared positive photosensitive compositions was applied thereunto and baked at 110° C. for 60 seconds, thereby forming a 160 nm-thick resist film. The resultant wafer was patternwise exposed by means of an ArF excimer laser scanner (manufactured by ASML, PAS5500/1100, NA0.75, Annular σo/σi=0.89/0.65). Thereafter, the exposed wafer was heated at 110° C. for 60 seconds, developed with an aqueous solution of tetramethylammonium hydroxide (2.38 mass %) for 30 seconds, rinsed with pure water and spin dried, thereby obtaining a resist pattern.

[Exposure Latitude]

The optimum exposure intensity is defined as the exposure intensity that reproduces an 85 nm 1:1 line and space mask pattern. The exposure intensity width in which when the exposure intensity is varied, the pattern size allows 85 nm ±10% is measured. The exposure latitude is the quotient of the value of the exposure intensity width divided by the optimum exposure intensity, the quotient expressed by a percentage. The greater the value of the exposure latitude, the less the change of performance by exposure intensity changes and the more favorable the exposure latitude.

[Line Edge Roughness]

In the measurement of line edge roughness, a 120 nm isolated pattern produced at the optimum exposure intensity was observed by means of a critical dimension SEM (model S-9260 manufactured by Hitachi, Ltd.). With respect to a 5 μm range of the longitudinal edge of a line pattern, the distance from a reference line on which edges were to be present was measured on 50 points. The standard deviation of measurements was determined, and 3c was computed. The smaller the value thereof, the higher the performance exhibited.

[Scum]

○: no scum observed at all,

Δ: scum found at a line width of around a limiting resolution, and

×: scum found at a line width greater than that of a limiting resolution.

[Sensitivity]

The optimum exposure intensity was defined as the exposure intensity that reproduced an 85 nm line and space mask pattern. This was evaluated as representing the sensitivity.

TABLE 1

| | Photoacid generator(A) [add. amt (g)] | Photoacid generator used in comb. [0.1 g] | Resin(B) [10 g] | Basic compound [add. amt (g)] | Surfactant [100 ppm] | Solvent [mass ratio] |
|---|---|---|---|---|---|---|
| Ex. 1 | X10 [0.2] | — | RA-1 | TPSA [0.03] | W-2 | S1/S3 [60/40] |
| Ex. 2 | X10 [0.2] | z66 | RA-2 | DBA [0.02] | W-1 | S1/S5 [70/30] |
| Ex. 3 | X10 [0.1] | z2 | RA-3 | PEA [0.03] | W-1 | S1/S5 [80/20] |
| Ex. 4 | X15 [0.2] | — | RA-4 | TPSA [0.04] | W-1 | S1/S2 [80/20] |
| Ex. 5 | X11 [0.2] | — | RA-5 | PBMA [0.03] | W-2 | S1/S4 [95/5] |
| Ex. 6 | X13 [0.1] | — | RA-6 | PBI [0.02] | W-4 | S1/S3 [60/40] |
| Ex. 7 | X12 [0.2] | Y-33 | RA-7 | PEA [0.02] | W-1 | S1/S3 [70/30] |
| Ex. 8 | X20 [0.2] | — | RA-8 | PBI [0.02] | W-1 | S1/S3 [60/40] |
| Ex. 9 | X16 [0.1] | — | RA-9 | PBMA [0.02] | W-3 | S1/S3 [60/40] |
| Ex. 10 | X24 [0.2] | — | RA-10 | TMEA [0.02] | W-1 | S1/S3 [60/40] |
| Ex. 11 | X32 [0.2] | Y-76 | RA-11 | DIA [0.02] | W-1 | S1/S3 [60/40] |
| Ex. 12 | X10 [0.1] X21 [0.1] | — | RA-12 [5 g] RA-1 [5 g] | TMEA [0.02] | W-2 | S3 [100] |
| Ex. 13 | X50 [0.2] | — | RA-2 | PBI [0.02] | W-2 | S1/S3 [60/40] |
| Ex. 14 | X52 [0.2] | — | RA-1 | DBA [0.02] | W-1 | S1/S3 [60/40] |
| Comp. 1 | Y-1 [0.3] | — | RA-1 | TPSA [0.03] | W-2 | S1/S3 [60/40] |
| Comp. 2 | Y-3 [0.3] | — | RA-1 | TPSA [0.03] | W-2 | S1/S3 [60/40] |
| Comp. 3 | A-56 [0.3] | — | RA-1 | TPSA [0.03] | W-2 | S1/S3 [60/40] |

| | Exposure latitude [%] | LER [nm] | Scum | Sensitivity [mJ/cm$^2$] |
|---|---|---|---|---|
| Ex. 1 | 16.3 | 6.9 | ○ | 35.0 |
| Ex. 2 | 14.7 | 6.5 | ○ | 36.0 |

TABLE 1-continued

| | | | | |
|---|---|---|---|---|
| Ex. 3 | 16.8 | 6.2 | ○ | 36.2 |
| Ex. 4 | 16.0 | 6.4 | ○ | 35.4 |
| Ex. 5 | 15.9 | 6.8 | ○ | 35.8 |
| Ex. 6 | 16.9 | 6.2 | ○ | 35.6 |
| Ex. 7 | 16.5 | 6.8 | ○ | 35.7 |
| Ex. 8 | 16.9 | 6.8 | ○ | 35.9 |
| Ex. 9 | 14.6 | 6.2 | ○ | 36 |
| Ex. 10 | 16.8 | 6.4 | ○ | 36.2 |
| Ex. 11 | 14.3 | 6.8 | ○ | 35.9 |
| Ex. 12 | 14.7 | 6.2 | ○ | 35 |
| Ex. 13 | 15.8 | 6.6 | ○ | 35.5 |
| Ex. 14 | 16.5 | 6.9 | ○ | 36.9 |
| Comp. 1 | 10.9 | 8.5 | Δ | 45.5 |
| Comp. 2 | 9.1 | 8.2 | x | 44.3 |
| Comp. 3 | 11.1 | 7.9 | Δ | 43.4 |

The employed components are as follows. [Acid Generators]

Acid generators A: acid generators $X_{10}$ to $X_{12}$, $X_{13}$, $X_{15}$, $X_{16}$, $X_{20}$, $X_{21}$, $X_{24}$ and X32 given as examples hereinbefore.

Companion acid generators: acid generators Y-1 and Y-3 given as examples hereinbefore, and acid generator A-56 given below.

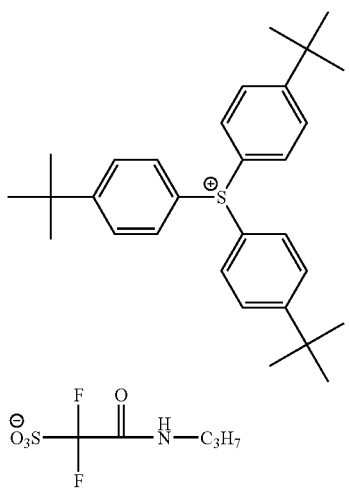

(A-56)

[Resins B]
Resins RA-1 to RA-12 were those prepared above.
[Basic Compounds]
TPSA: triphenylsulfonium acetate,
DIA: 2,6-diisopropylaniline,
DBA: N,N-dibutylaniline,
PBI: 2-phenylbenzimidazole,
TMEA: tris(methoxyethoxyethyl)amine,
PEA: N-phenyldiethanolamine, and
PBMA: 2-[2-{2-(2,2-dimethoxy-phenoxyethoxy)ethyl}-bis(2-methoxyethyl)]-amine.
[Surfactants]
W-1: Megafac F176 (produced by Dainippon Ink & Chemicals, Inc.) (fluorinated),
W-2: Megafac R08 (produced by Dainippon Ink & Chemicals, Inc.) (fluorinated and siliconized),
W-3: polysiloxane polymer KP-341 (produced by Shin-Etsu Chemical Co., Ltd.) (siliconized), and
W-4: Troy Sol S-366 (produced by Troy Chemical Co., Ltd.).

[Solvents]
S1: propylene glycol methyl ether acetate,
S2: 2-heptanone,
S3: cyclohexanone,
S4: γ-butyrolactone, and
S5: propylene glycol methyl ether.

It is apparent from the results of Table 1 that in the performance evaluation having employed an ArF beam exposure, the compositions of the present invention are superior to the compositions of the Comparative Examples in the sensitivity, resolving power and exposure margin.

Example 15 and Comparative Example 4

Referring to Table 2, below, appropriate components were dissolved in solvents, and passed through a polytetrafluoroethylene filter of 0.1 μm pore size, thereby obtaining positive resist solutions of 8 mass % solid content. The thus obtained positive resist solutions were evaluated by the following methods.

<Evaluation of Resists>

Each of the obtained positive resist solutions was uniformly applied onto a silicon substrate having undergone a hexamethyldisilazane treatment by use of a spin coater, and dried by heating on a hot plate at 120° C. for 60 seconds, thereby forming a 0.15 μm-thick resist film.

[Sensitivity and γ-Value]

Onto each of the obtained resist films, surface exposure was carried out by use of EUV rays (wavelength 13 nm) while changing the exposure intensity by 0.5 mJ/cm² at a time within the range of 0 to 10.0 mJ/cm², and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

The sensitivity was defined as the exposure intensity at which the dissolution rate of the resist was saturated on the sensitivity curve. Dissolution contrast (γ value) was calculated from the gradient of the straight line portion of the sensitivity curve. The larger the γ value, the greater the excellence in dissolution contrast. [Line Edge Roughness]

On arbitrary 30 points in a 50 μm region in the longitudinal direction of a 50 nm line pattern at the exposure intensity realizing the above sensitivity, the distance from a reference line on which edges were to be present was measured by means of a scanning electron microscope (model S-9220, manufactured by Hitachi, Ltd.). The standard deviation of measurements was determined, and 3σ was computed. The smaller the value thereof, the higher the performance exhibited.

TABLE 2

| | Photoacid generator(A) [add. amt (g)] | Resin(B) [10 g] | Basic compound [add. amt (g)] | Surfactant [100 ppm] | Solvent [mass ratio] | LER [nm] | Resolving power γ-value |
|---|---|---|---|---|---|---|---|
| Ex. 15 | X10 [0.2] | RA-13 | TEA [0.03] | W-2 | S1/S3 [60/40] | 5.0 | 6.3 |
| Comp. 4 | Y-1 [0.2] | RA-13 | TEA [0.03] | W-2 | S1/S3 [60/40] | 8.0 | 3.2 |

Among the employed components, those not recited in Table 1 are as follows.

[Resin B]

<Synthesis of p-(1-(cyclohexylethoxy)ethoxy)styrene/p-hydroxystyrene (40/60) (resin RA-13)>

While heating, 70 g of p-hydroxystyrene (VP-8000, produced by Nippon Soda Co., Ltd.) was dissolved in 320 g of propylene glycol monomethyl ether acetate (PGMEA). The solution was dehydrated by vacuum distillation, and cooled to 20° C. Subsequently, 41.4 g of cyclohexyl vinyl ether was added and agitated. Then, 100 mg of p-toluenesulfonic acid was added to the mixture, and reaction was performed for 3 hours. Thereafter, 0.28 g of triethylamine and 320 ml of ethyl acetate were added to the reaction mixture, and washed with 150 ml of distilled water three times. The washed mixture was concentrated by distilling off the solvent. The thus obtained oil was dissolved in 100 ml of acetone, and the solution was slowly poured into 2 liters of distilled water. The thus precipitated powder was collected by filtration and dried, thereby obtaining 54 g of desired resin RA-13 (weight average molecular weight 10,000 and dispersity 1.30).

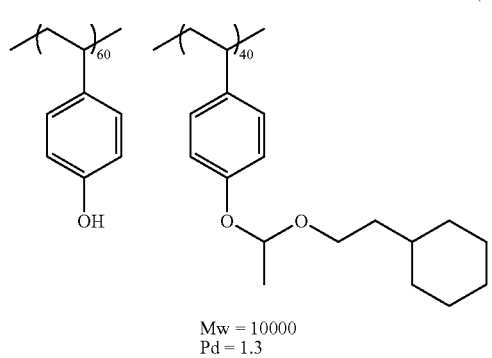

(RA-13)

Mw = 10000
Pd = 1.3

[Basic Compound]

TEA: triethanolamine.

It is apparent from the results of Table 2 that in the performance evaluation having employed an EUV ray exposure, the resist composition of the present invention is superior to the composition of the Comparative Example in the resolving power.

What is claimed is:

1. A positive photosensitive composition comprising at least one compound that when exposed to actinic rays or radiation, generates any of the sulfonic acids of general formula (I) and a resin whose solubility in an alkali developer is increased by the action of an acid,

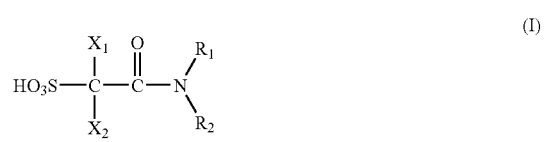

(I)

wherein each of $X_1$ and $X_2$ independently represents a fluorine atom or a fluoroalkyl group; $R_1$ represents a group with a polycyclic structure, provided that the polycyclic structure may have a substituent; and $R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent, and provided that $R_1$ and $R_2$ may be bonded to each other to thereby form a polycyclic structure.

2. The positive photosensitive composition according to claim 1, wherein the compound that when exposed to actinic rays or radiation, generates any of the sulfonic acids of general formula (I) is any of the compounds of general formula (II):

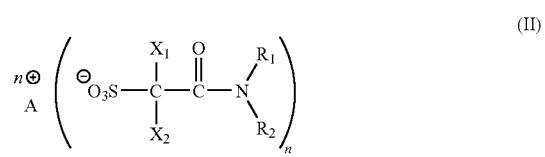

(II)

wherein $A^+$ represents an organic counter ion; n is 1 or 2; and $X_1$, $X_2$, $R_1$ and $R_2$ are as defined above with respect to general formula (I).

3. The positive photosensitive composition according to claim 2, wherein in general formula (II), $A^+$ is any of the cations of any of formulae (IIIa), (IIIb), (IIIc) and (IIId):

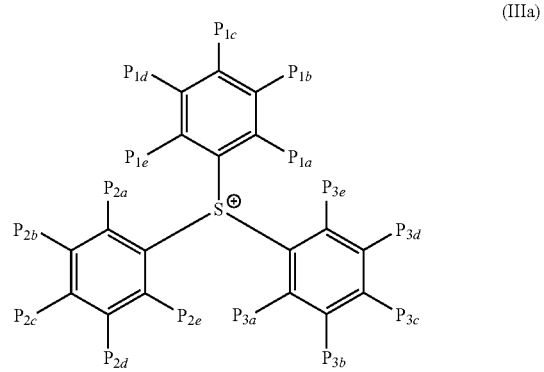

(IIIa)

wherein each of $P_{1a}$ to $P_{1e}$, each of $P_{2a}$ to $P_{2e}$, and each of $P_{3a}$ to $P_{3e}$ independently represents a hydrogen atom, a hydroxyl group, an alkyl group having 1 to 12 carbon atoms, a cycloalkyl group having 3 to 12 carbon atoms or a chain or alicyclic alkoxy group having 1 to 12 carbon atoms, provided that each of the alkyl group, cycloalkyl group and alkoxy group may have a substituent, and provided that $P_{1a}$ and $P_{3e}$, $P_{1e}$ and $P_{2a}$, and $P_{2e}$ and $P_{3a}$ may be bonded to each other through a single bond, methylene group, an ether bond or a sulfide bond,

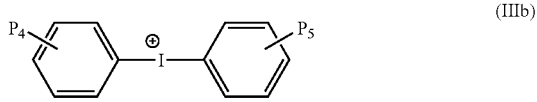

(IIIb)

wherein each of $P_4$ and $P_5$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent,

(IIIc)

wherein each of $P_6$ and $P_7$ independently represents an alkyl group having 1 to 12 carbon atoms or a cycloalkyl group having 3 to 12 carbon atoms, provided that each of the alkyl group and cycloalkyl group may have a substituent, and provided that $P_6$ and $P_7$ may be bonded to each other so as to represent a bivalent hydrocarbon group having 3 to 12 carbon atoms, and wherein $P_8$ represents a hydrogen atom, and $P_9$ represents an alkyl group having 1 to 12 carbon atoms, a cycloalkyl group having 3 to 12 carbon atoms or an aromatic ring group, provided that each of the alkyl group, cycloalkyl group and aromatic ring group may have a substituent, and provided that $P_8$ and $P_9$ may be bonded to each other so as to represent a bivalent hydrocarbon group having 3 to 12 carbon atoms, and wherein any of the carbon atoms contained in the bivalent hydrocarbon group may be substituted by a carbonyl group, an oxygen atom or a sulfur atom, and

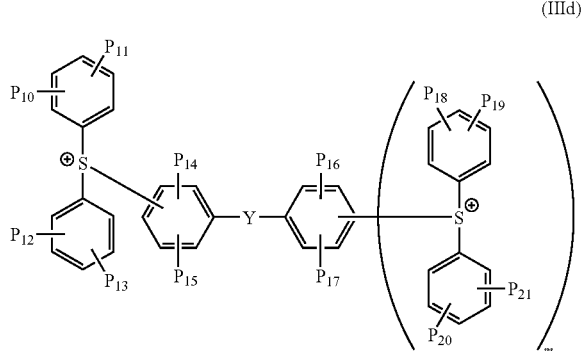

(IIId)

wherein each of $P_{10}$ to $P_{21}$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent, and wherein Y represents a sulfur atom or an oxygen atom, and m is 0 or 1.

4. The positive photosensitive composition according to claim 2, wherein in general formula (II), $A^+$ is any of the cations of formula (IIIe):

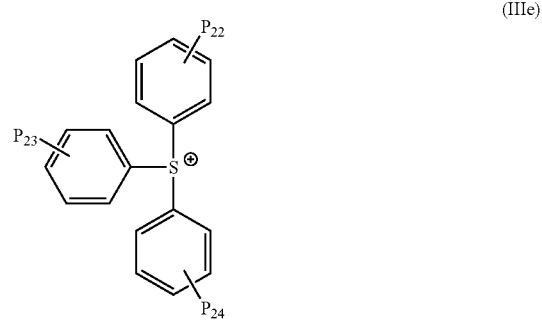

(IIIe)

wherein each of $P_{22}$ to $P_{24}$ independently represents a hydrogen atom or an alkyl group having 1 to 4 carbon atoms, provided that the alkyl group may have a substituent.

5. The positive photosensitive composition according to claim 1, wherein in general formula (I), both of $X_1$ and $X_2$ represent a fluorine atom.

6. The positive photosensitive composition according to claim 1, wherein the resin has a lactone structure.

7. A method of forming a pattern, comprising forming the positive photosensitive composition according to claim 1 into a coating film, exposing the coating film to actinic rays or radiation and developing the exposed coating film by use of an alkali developer.

8. A compound capable of, when exposed to actinic rays or radiation, generating any of the sulfonic acids of general formula (I),

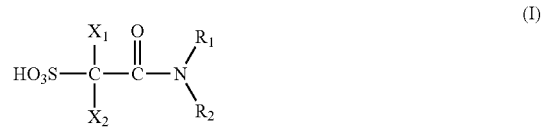

(I)

wherein each of $X_1$ and $X_2$ independently represents a fluorine atom or a fluoroalkyl group; $R_1$ represents a group with a polycyclic structure, provided that the polycyclic structure may have a substituent; and $R_2$ represents a hydrogen atom, a chain alkyl group, a monocyclic alkyl group, a group with a polycyclic structure or a monocyclic aryl group, provided that each of the chain alkyl group, monocyclic alkyl group, polycyclic structure and monocyclic aryl group may have a substituent, and provided that $R_1$ and $R_2$ may be bonded to each other to thereby form a polycyclic structure.

9. The compound capable of, when exposed to actinic rays or radiation, generating any of the sulfonic acids of general formula (I) according to claim 8, which compound is any of the compounds of general formula (II):

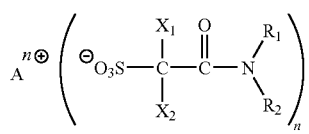

wherein A⁺ represents an organic counter ion; n is 1 or 2; and $X_1$, $X_2$, $R_1$ and $R_2$ are as defined above with respect to general formula (I).

10. The compound according to claim 9, wherein in general formula (II), A⁺ is any of the cations of any of formulae (IIIa), (IIIb), (IIIc) and (IIId):

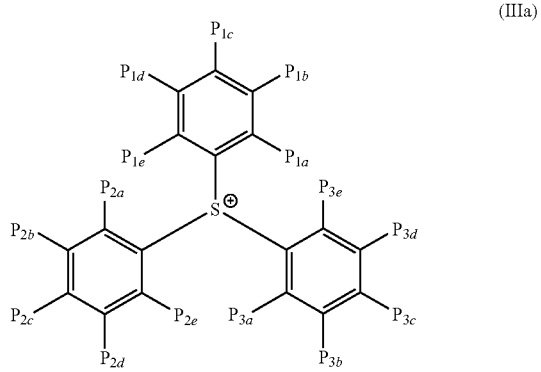

wherein each of $P_{1a}$ to $P_{1e}$, each of $P_{2a}$ to $P_{2e}$, and each of $P_{3a}$ to $P_{3e}$ independently represents a hydrogen atom, a hydroxyl group, an alkyl group having 1 to 12 carbon atoms, a cycloalkyl group having 3 to 12 carbon atoms or a chain or alicyclic alkoxy group having 1 to 12 carbon atoms, provided that each of the alkyl group, cycloalkyl group and alkoxy group may have a substituent, and provided that $P_{1a}$ and $P_{3e}$, $P_{1e}$ and $P_{2a}$, and $P_{2e}$ and $P_{3a}$ may be bonded to each other through a single bond, methylene, an ether bond or a sulfide bond,

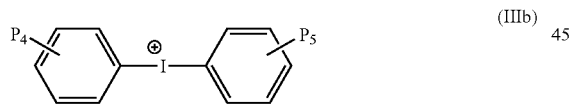

wherein each of $P_4$ and $P_5$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent,

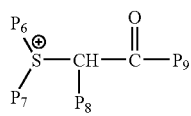

wherein each of $P_6$ and $P_7$ independently represents an alkyl group having 1 to 12 carbon atoms or a cycloalkyl group having 3 to 12 carbon atoms, provided that each of the alkyl group and cycloalkyl group may have a substituent, and provided that $P_6$ and $P_7$ may be bonded to each other so as to represent a bivalent hydrocarbon group having 3 to 12 carbon atoms, and wherein $P_8$ represents a hydrogen atom, and $P_9$ represents an alkyl group having 1 to 12 carbon atoms, a cycloalkyl group having 3 to 12 carbon atoms or an aromatic ring group, provided that each of the alkyl group, cycloalkyl group and aromatic ring group may have a substituent, and provided that $P_8$ and $P_9$ may be bonded to each other so as to represent a bivalent hydrocarbon group having 3 to 12 carbon atoms, and wherein any of the carbon atoms contained in the bivalent hydrocarbon group may be substituted by a carbonyl group, an oxygen atom or a sulfur atom, and

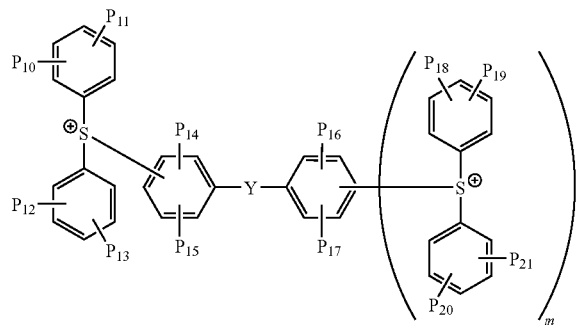

wherein each of $P_{10}$ to $P_{21}$ independently represents a hydrogen atom, a hydroxyl group, an alkyl group having 1 to 12 carbon atoms, a cycloalkyl group having 3 to 12 carbon atoms, a chain or alicyclic alkoxy group having 1 to 12 carbon atoms or a halogen atom, provided that each of the alkyl group, cycloalkyl group and alkoxy group may have a substituent, and wherein Y represents a sulfur atom or an oxygen atom, and m is 0 or 1.

11. The compound according to claim 9, wherein in general formula (II), A⁺ is any of the cations of formula (IIIe):

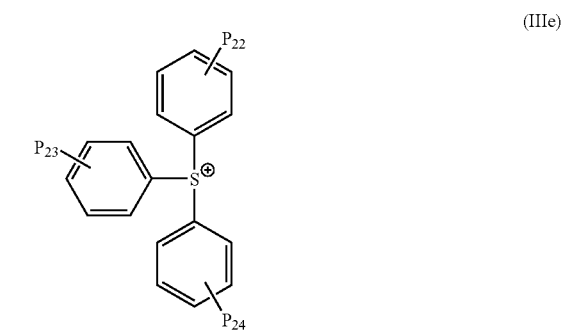

wherein each of $P_{22}$ to $P_{24}$ independently represents a hydrogen atom or an alkyl group having 1 to 4 carbon atoms, provided that the alkyl group may have a substituent.

12. A process for producing the compound of general formula (II) according to claim 9, comprising reacting any of the amines of general formula (V) with any of the ester compounds of general formula (VII),

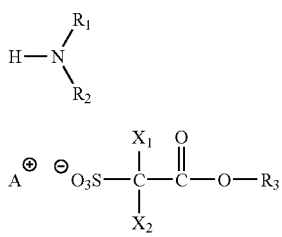

wherein in general formula (V), $R_1$ and $R_2$ are as defined above with respect to general formula (II), and wherein in general formula (VII), $A^+$, $X_1$ and $X_2$ are as defined above with respect to general formula (II), and $R_3$ represents a chain alkyl group, a cycloalkyl group or a group with a polycyclic structure, provided that each of the chain alkyl group and cycloalkyl group may have a substituent.

13. The compound according to claim 8, wherein in general formula (I), both of $X_1$ and $X_2$ represent a fluorine atom.

14. A photoacid generator comprised of any of the compounds of claim 8.

15. A compound of general formula (IV),

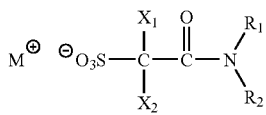

wherein $M^+$ represents a metal ion; each of $X_1$ and $X_2$ independently represents a fluorine atom or a fluoroalkyl group; $R_1$ represents a group with a polycyclic structure; and $R_2$ represents a hydrogen atom, a chain alkyl group, a monocyclic alkyl group, a group with a polycyclic structure or a monocyclic aryl group, provided that each of the chain alkyl group, monocyclic alkyl group and monocyclic aryl group may have a substituent, and provided that $R_1$ and $R_2$ may be bonded to each other to thereby form a polycyclic structure.

16. The compound according to claim 15, wherein in general formula (IV), both of $X_1$ and $X_2$ represent a fluorine atom.

17. A process for producing the compound of general formula (IV) according to claim 15, comprising reacting any of the amines of general formula (V) with any of the ester compounds of general formula (VI),

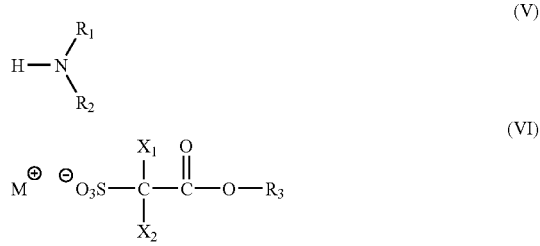

wherein in general formula (V), $R_1$ and $R_2$ are as defined above with respect to general formula (IV), and wherein in general formula (VI), $M^+$, $X_1$ and $X_2$ are as defined above with respect to general formula (IV), and $R_3$ represents a chain alkyl group, a cycloalkyl group or a group with a polycyclic structure, provided that each of the chain alkyl group and cycloalkyl group may have a substituent.

* * * * *